US 11,723,747 B2

(12) United States Patent
Boutoussov et al.

(10) Patent No.: US 11,723,747 B2
(45) Date of Patent: *Aug. 15, 2023

(54) DENTAL SYSTEM AND METHOD

(71) Applicant: Biolase, Inc., Irvine, CA (US)

(72) Inventors: Dmitri Boutoussov, Dana Point, CA (US); Doug Patton, Costa Mesa, CA (US); Richard Jackson, Trabuco Canyon, CA (US); Channing Shattuck, Bonsall, CA (US)

(73) Assignee: Biolase, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/492,827

(22) Filed: Oct. 4, 2021

(65) Prior Publication Data
US 2022/0202525 A1    Jun. 30, 2022

Related U.S. Application Data

(63) Continuation of application No. 15/851,452, filed on Dec. 21, 2017, now Pat. No. 11,202,687.
(Continued)

(51) Int. Cl.
*A61C 1/00* (2006.01)
*G06F 3/04817* (2022.01)
(Continued)

(52) U.S. Cl.
CPC .......... *A61C 1/0015* (2013.01); *A61C 1/0046* (2013.01); *G06F 3/0482* (2013.01); *G06F 3/04817* (2013.01); *G06F 3/04847* (2013.01)

(58) Field of Classification Search
CPC . A61C 1/0015; A61C 1/0046; G06F 3/04817; G06F 3/0482; G06F 3/04847
See application file for complete search history.

(56) References Cited

U.S. PATENT DOCUMENTS

| 6,463,343 B1 | 10/2002 | Emens et al. |
| 6,847,336 B1 | 1/2005 | Lemelson et al. |

(Continued)

FOREIGN PATENT DOCUMENTS

| AU | 2015101183 A4 * | 10/2015 | ....... G06F 17/30905 |
| CA | 2993310 A1 * | 3/2018 | .......... G06F 11/3006 |
| WO | 2004016182 A1 | 2/2004 | |

OTHER PUBLICATIONS

International Search Report and Written Opinion for International Application No. PCT/US2017/068009, dated May 14, 2018, 19 pages.
(Continued)

*Primary Examiner* — Pinalben Patel
(74) *Attorney, Agent, or Firm* — Greenberg Traurig, LLP

(57) ABSTRACT

Embodiments of the invention provide a laser system including a laser station including at least one laser, at least one processor, and at least one non-transitory computer-readable storage medium in data communication with the at least one processor. The at least one non-transitory computer-readable storage medium includes program instructions executable by the at least one processor, and enabling or operating an exchange of data between the at least one laser station and at least one remote network. The laser system includes at least one GUI display configured and arranged to display operating parameters or functions of the at least one laser and/or any of the data exchanged between the laser station and at least one remote network. The program instructions include instructions that direct the processor to update the at least one GUI display with a plurality of user-selectable graphics arranged around the periphery or circumference of a central display.

19 Claims, 33 Drawing Sheets

Related U.S. Application Data

(60) Provisional application No. 62/438,741, filed on Dec. 23, 2016.

(51) Int. Cl.
    *G06F 3/04847*     (2022.01)
    *G06F 3/0482*     (2013.01)

(56) References Cited

U.S. PATENT DOCUMENTS

| | | |
|---|---|---|
| 7,199,790 B2 | 4/2007 | Rosenberg et al. |
| 9,652,590 B2 | 5/2017 | Yeager |
| 11,202,687 B2 * | 12/2021 | Boutoussov ........... G16H 40/63 |
| 2009/0225060 A1 | 9/2009 | Rizoiu et al. |
| 2013/0104071 A1 | 4/2013 | Boutoussov et al. |
| 2013/0330684 A1 | 12/2013 | Dillon et al. |
| 2015/0268803 A1 | 9/2015 | Patton et al. |
| 2016/0019352 A1 | 1/2016 | Cohen et al. |
| 2016/0321404 A1 | 11/2016 | Ginsburg |

OTHER PUBLICATIONS

Lin, Yuan-Hsiang, et al. "A wireless PDA-based physiological monitoring system for patient transport." IEEE Transactions on information technology in biomedicine 8.4 (2004): 439-447. (Year: 2004).

Samei, Ehsan, et al. "AAPM/RSNA tutorial on equipment selection: PACS equipment overview: general guidelines for purchasing and acceptance testing of PACS equipment." Radiographies 24.1 (2004): 313-334 (Year: 2004).

Extended European Search Report dated Aug. 3, 2020 for European Application No. 17884350.4, 10 pages.

* cited by examiner

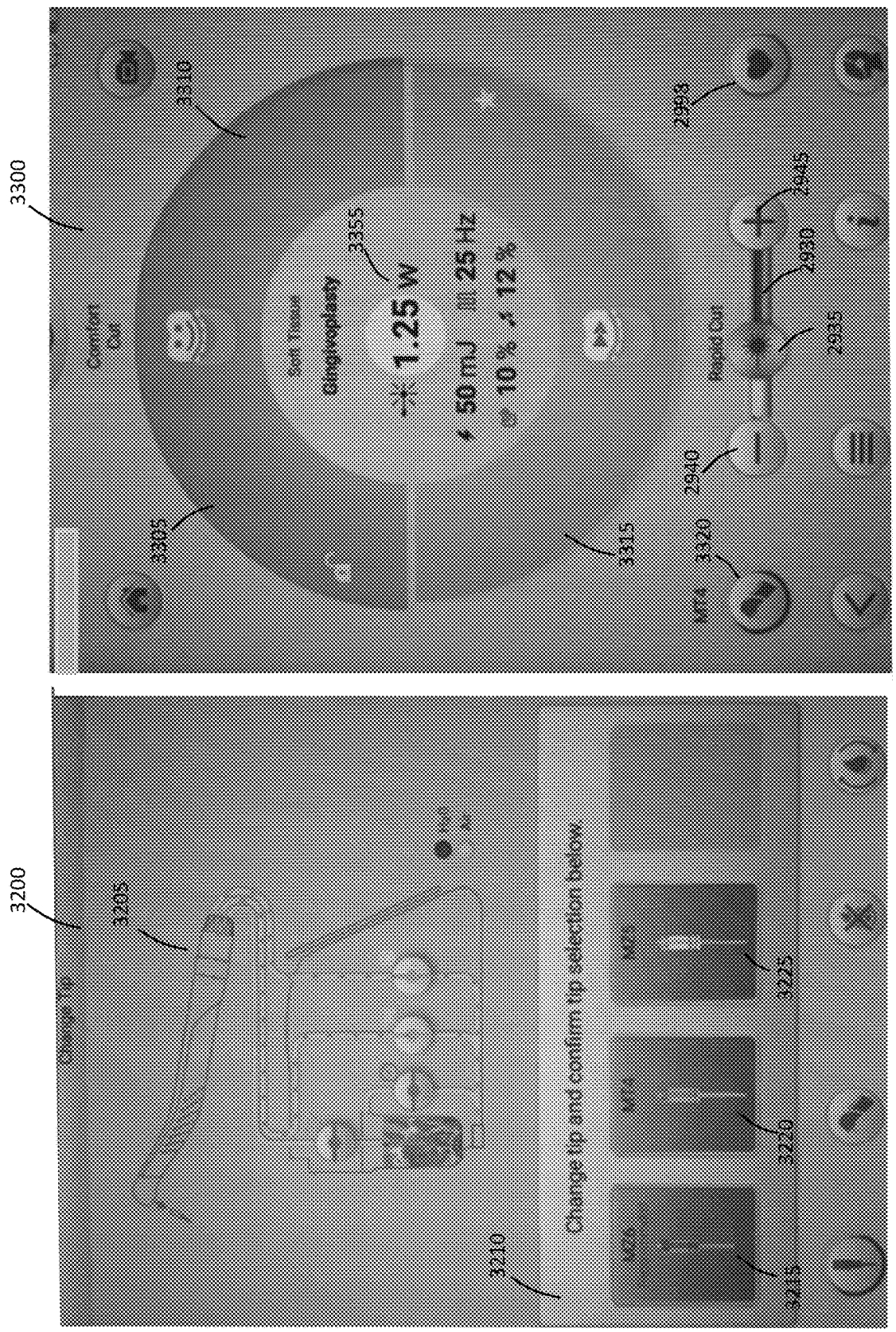

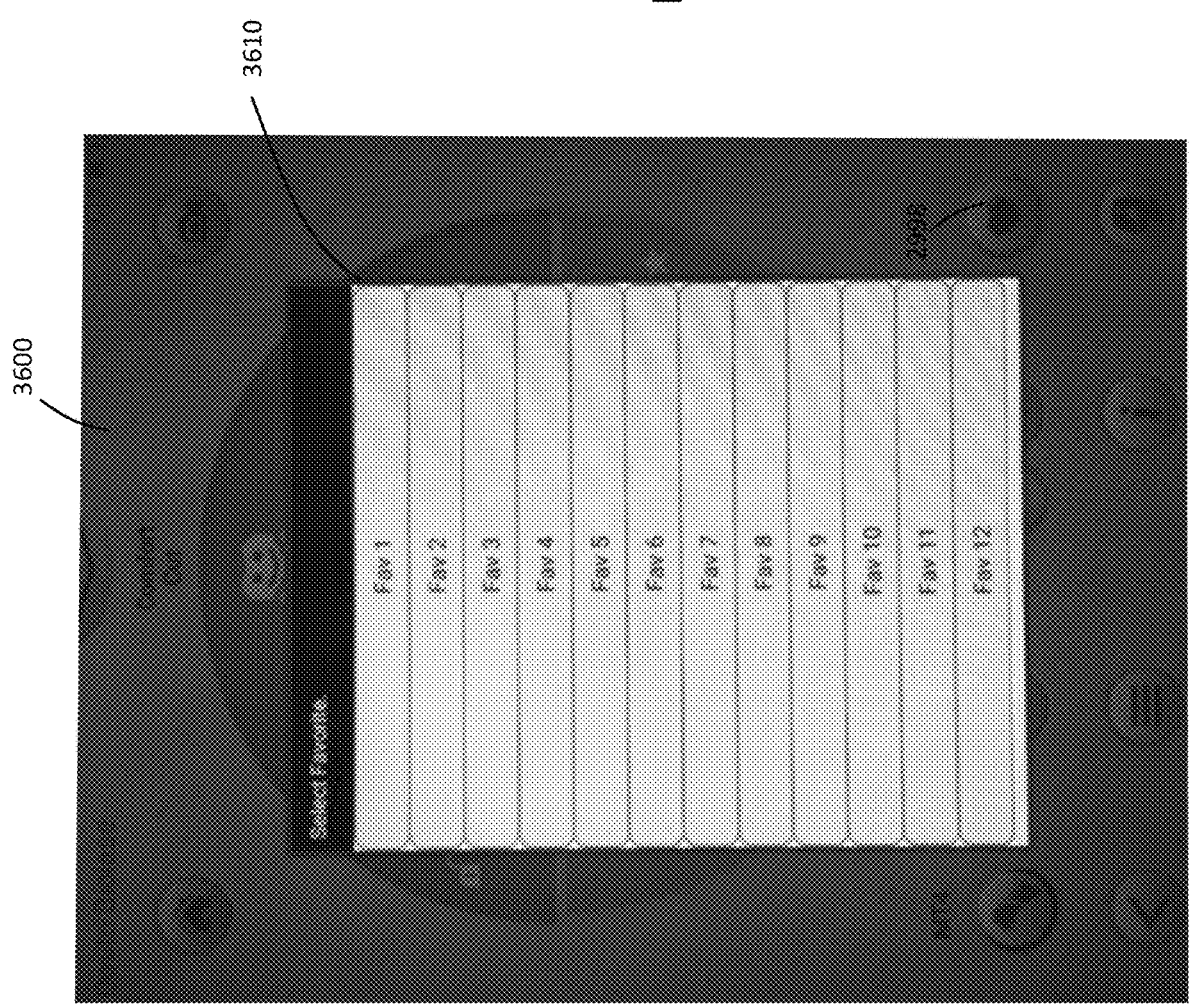

| Level 0 | Level 1 | Level 2 | | Pre-set | | | | BASIC | | | | | | | | ADVANCED | | |
|---|---|---|---|---|---|---|---|---|---|---|---|---|---|---|---|---|---|---|
| Categories | Procedures | Options / Steps | | | | | | MIN | | | | MAX | | | | RANGES | | |
| | | | tip | Energy | PPS | W | A...H₂energy | PPS | W | A...H₂energy | PPS | W | A...H₂OMode | energy | PPS | mode | Air | H₂O |
| Open Flap For Perio Pathology (A) | Gingivae | | M26 | 15 | 30 | 0.45 | 10...10 | 10 | 30 | 0.30 | 10...10 | 25 | 30 | 0.75 | 10...10 | H | 10-30 | 30 | H | 0-20 | 0-20 |
| | Incisions | | M25, M23, M14 | 50 | 30 | 1.50 | 40...50 | 40 | 30 | 1.20 | 40...50 | 60 | 30 | 1.80 | 40...50 | H | 40-60 | 30 | H | 20-50 | 30-70 |
| | Coarse De-epithelialization | | M25, M23, M14 | 25 | 30 | 0.75 | 40...50 | 15 | 30 | 0.45 | 40...50 | 35 | 30 | 1.05 | 40...50 | H | 15-35 | 30 | H | 20-50 | 30-70 |
| | Laser Assisted Flap Reflection | | M25, M23, M14 | 50 | 30 | 1.50 | 40...50 | 40 | 30 | 1.20 | 40...50 | 60 | 30 | 1.80 | 40...50 | H | 40-60 | 30 | H | 20-50 | 30-70 |
| | Secondary Incision | | M25, M23, M14 | 50 | 30 | 1.50 | 40...50 | 40 | 30 | 1.20 | 40...50 | 60 | 30 | 1.80 | 40...50 | H | 40-60 | 30 | H | 20-50 | 30-70 |
| | Degranulation and Collar Removal | | M25, M23, M14 | 80 | 25 | 2.00 | 40...50 | 70 | 25 | 1.75 | 40...50 | 90 | 25 | 2.25 | 40...50 | H | 70-100 | 15-30 | H | 30-70 | 30-70 |
| | Root Surface Modification | | RFPT5 | 25 | 30 | 0.75 | 70...80 | 15 | 30 | 0.45 | 70...80 | 35 | 30 | 1.05 | 70...80 | H | 15-35 | 30 | H | 20-50 | 30-70 |
| | Osteotomy | | M25, M23, M14 | 120 | 25 | 3.00 | 70...80 | 100 | 25 | 2.50 | 70...80 | 130 | 25 | 3.50 | 70...80 | H | 80-140 | 20-30 | H | 60-80 | 50-90 |
| | Osteoplasty | | M25, M23, M14 | 45 | 50 | 2.25 | 70...80 | 40 | 50 | 2.00 | 70...80 | 50 | 50 | 2.50 | 70...80 | H | 40-50 | 50 | H | 60-80 | 70-90 |

FIG. 44

DENTAL SYSTEM AND METHOD

RELATED APPLICATIONS

This application is a Continuation Application of U.S. patent application Ser. No. 15/851,452, filed Dec. 21, 2017, which claims priority to U.S. provisional application Ser. No. 62/438,741, entitled 'DENTAL SYSTEM AND METHOD' filed on Dec. 23, 2016, the entire contents of which are incorporated herein by reference.

BACKGROUND

The increasing range and sophistication of dental laser tools has broadened their appeal within the dental community. Many dental practices will currently have at least one complex dental laser station that can include various control systems, displays, and one or more user interfaces of various forms that are used to control the tool, and/or monitor and communicate some function or operational characteristic of the tool. The laser station may include different electromagnetic energy sources that output different wavelengths of light that can be used together in performing various procedures. The dentist or other practitioner may be presented with options for adjusting one or more operating parameters of one or more of the electromagnetic energy sources using an interface of the laser station. However, the interface is generally not able to be coupled and decoupled from the station, and does not enable freedom of movement and mobile access, update, and control of any of the system parameters in an undocked or docked position.

SUMMARY

A laser system comprising at least one laser station including at least one laser, at least one processor, and at least one non-transitory computer-readable storage medium in data communication with the at least one processor. The at least one non-transitory computer-readable storage medium includes program instructions executable by the at least one processor and enabling or operating an exchange of data between the at least one laser station and at least one remote network. In some embodiments, the laser systems includes at least one GUI display configured and arranged to display at least one operating parameter or function of the at least one laser and/or any of the data exchanged between the at least one laser station and at least one remote network, where the program instructions include instructions sufficient to direct the processor to update the at least one GUI display with a plurality of user-selectable graphics arranged around the periphery or circumference of a central display.

In some embodiments, the at least one laser station comprises at least one dental laser station. Some embodiments further comprise a handpiece assembly coupled to or including the at least one laser. Further, the at least one GUI is enabled to monitor and/or enable adjustment of operational characteristics of the handpiece assembly.

In some embodiments, the at least one GUI display comprises a touchscreen display of a computer tablet or smartphone. In some embodiments, the GUI display is configured and arranged to enable monitoring and/or adjustment of operational characteristics of the at least one laser. In some embodiments, the program instructions enable download of training materials, videos, software, and firmware updates over remote network to the at least one laser station.

In some embodiments of the invention, the program instructions include instructions sufficient to direct the processor to update the at least one GUI display with a plurality of user-selectable graphics representing or including at least one medical or dental procedure. In some further embodiments, the program instructions include instructions sufficient to direct the processor to record or direct feedback from at least one patient from at least one clinical procedure.

In some embodiments, the program instructions include instructions sufficient to direct the processor to display interactive training, image-based clinical recommendations, and record at least one patient's outcome. In some further embodiments, the program instructions include instructions sufficient to direct the processor to enable alteration, uploading or deletion of at least one procedure by a user directly interacting with the laser station or remotely by a user or manufacturer.

In some embodiments, the program instructions include instructions sufficient to direct the processor to image compare or pattern recognize one or more clinical images loaded in its memory with one or more images from any procedure of the laser station. Some embodiments further comprise program instructions sufficient to direct the processor to provide clinical recommendations based at least in part on image comparison or pattern recognition.

In some embodiments, the at least one GUI includes a control and information display including the plurality of user-selectable graphics positioned as a control wheel. In some other embodiments, the plurality of user-selectable graphics include icons or segments representing selectable categories of procedures, where a user-selection of icons or segments is represented by color, shape, size, and animation of at least one selected icon or segment.

In some embodiments, the plurality of user-selectable graphics includes at least one icon selectable by a user to enable access of one or more favorites. In some embodiments, the plurality of user-selectable graphics includes category segments or buttons, configured and arranged to enable the at least one processor to modify attribute values, and/or to allow personification of a specific doctor's preference system.

In some further embodiments, the plurality of user-selectable graphics includes at least one controller configured and arranged to enable the at least one processor to update or modify at least one of the laser pulse peak power, laser pulse repetition rate, laser pulse duration, laser average output power, and volume and quality of the cooling water spray, and air flow. In some embodiments, the at least one controller comprises a slider.

In some embodiments, the program instructions are sufficient to direct the processor to display a schematic view of at least a portion of the at least one laser station. Further, some embodiments include program instructions sufficient to direct the processor to display at least one icon displayed to enable user selection of at least one laser tip.

In some embodiments, the at least one controller is a master controller configured and arranged to enable a user to substantially simultaneously set or alter more than one parameter selected from laser pulse peak power, laser pulse repetition rate, laser pulse duration, laser average output power, and volume and quality of the cooling water spray, and air flow.

DESCRIPTION OF THE DRAWINGS

FIG. 32 illustrates a tip change and confirm GUI display in accordance with some embodiments of the invention.

FIGS. 33-35 illustrate soft tissue "Gingivoplasty" control GUI displays in accordance with some embodiments of the invention.

FIG. 36 illustrates favorites selection column GUI display in accordance with some embodiments of the invention.

Figures 38, 39:
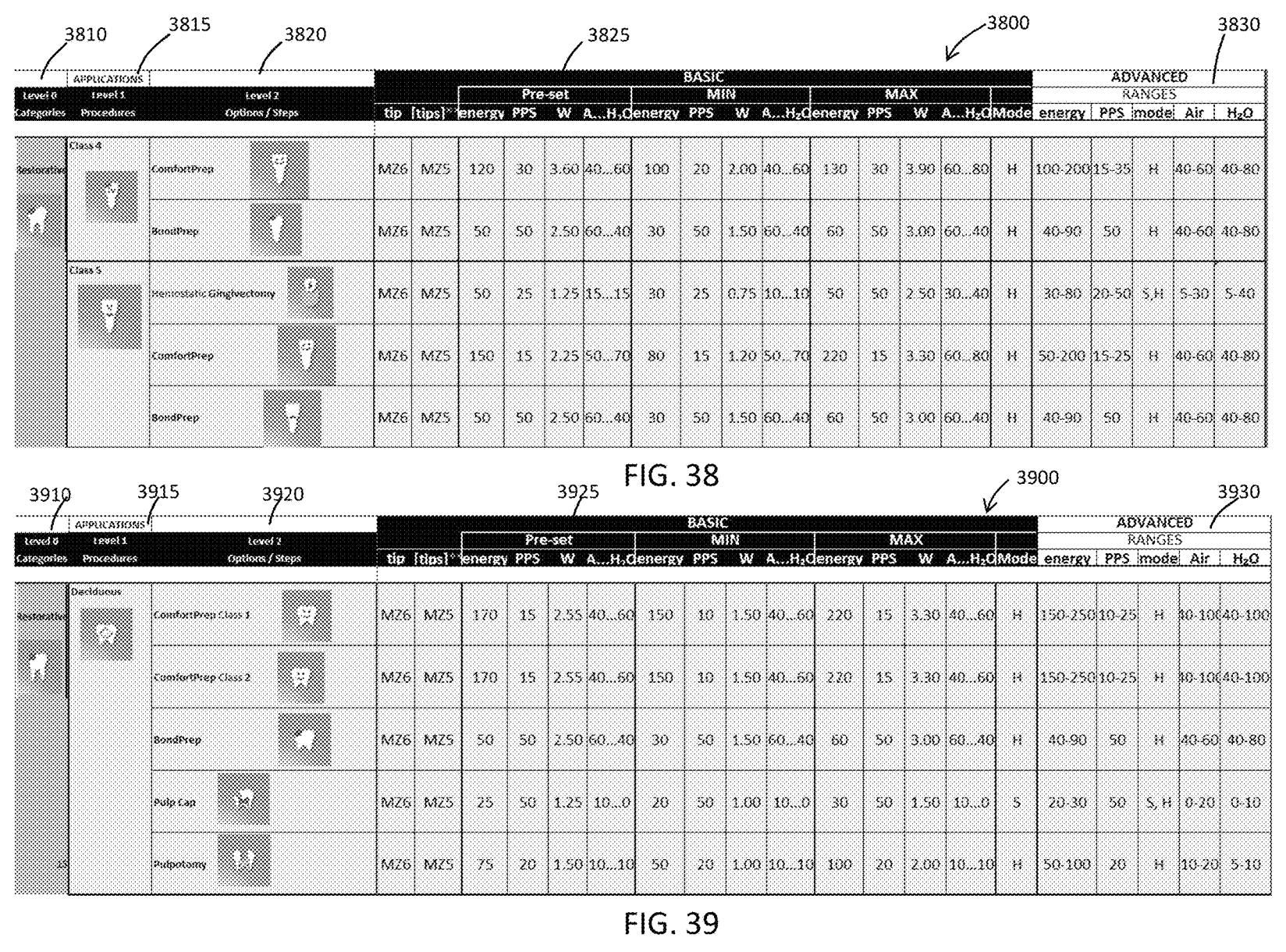

FIG. 38 shows a display of system settings and parameters for procedures, options, and steps for restorative categories and Class 4, and Class 5 procedures in accordance with some embodiments of the invention.

FIG. 39 shows a display of system settings and parameters for procedures, options, and steps for restorative categories and deciduous procedures in accordance with some embodiments of the invention.

Figures 40, 41:
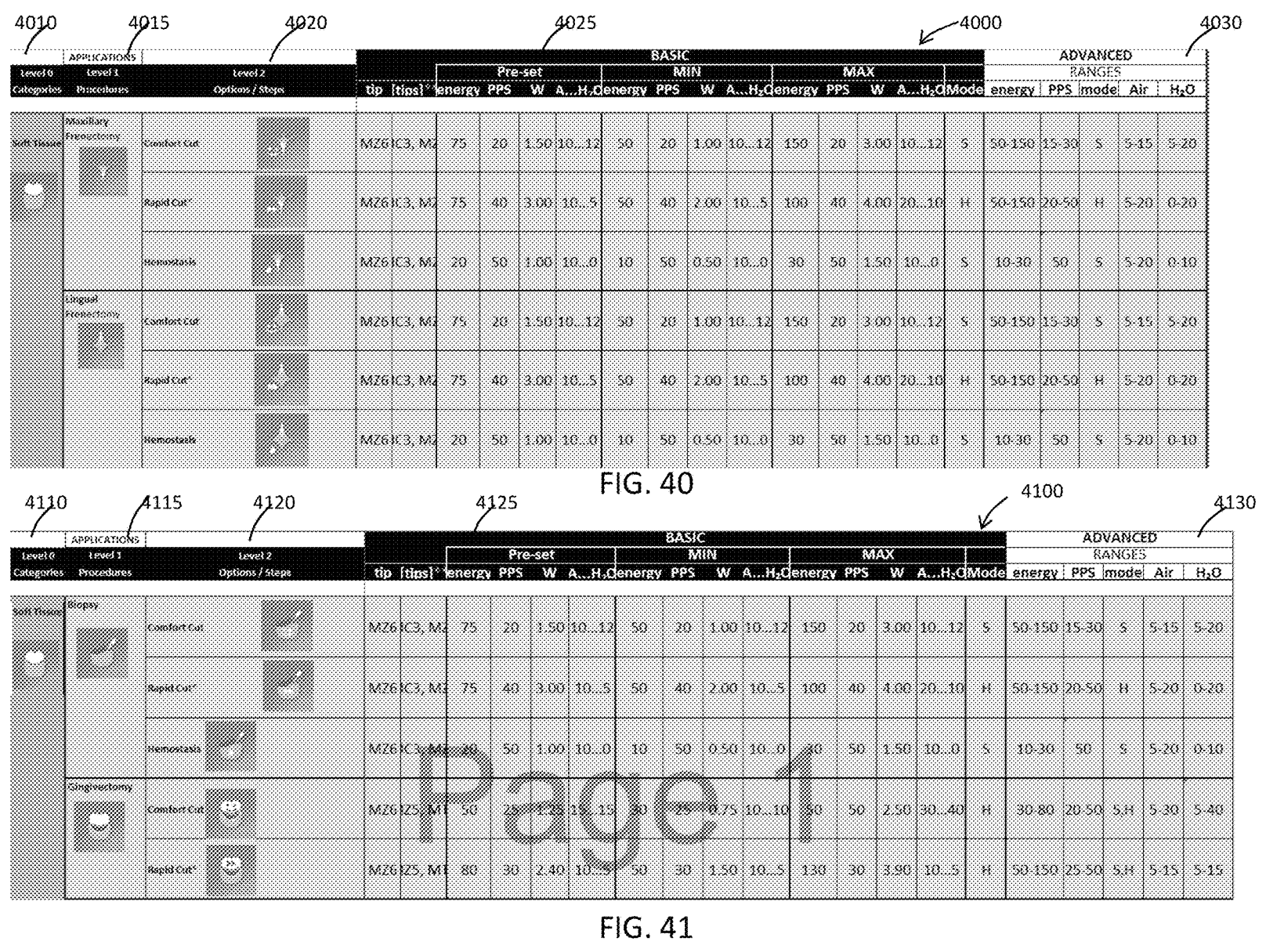

FIG. 40 shows a display of system settings and parameters for procedures, options, and steps for soft tissue categories and maxillary frenectomy, and lingual frenectomy procedures in accordance with some embodiments of the invention.

FIG. 41 shows system settings and parameters for procedures, options, and steps for soft tissue categories and biopsy, and gingivectomy procedures in accordance with some embodiments of the invention.

FIG. 44 shows a display of system settings and parameters for procedures, options, and steps for Periodontal categories and open flap procedures in accordance with some embodiments of the invention.

DETAILED DESCRIPTION

Figure 1A:
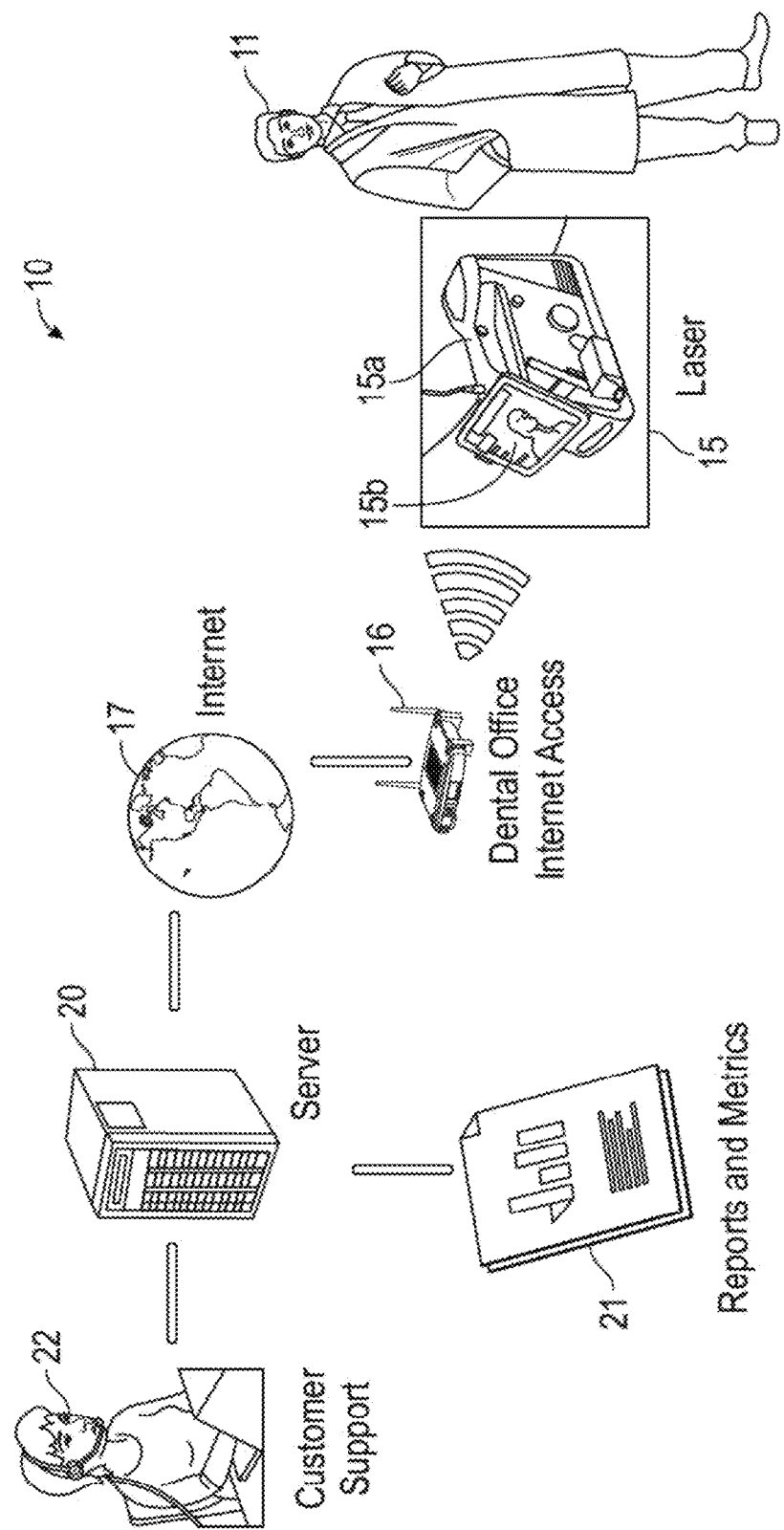
FIG. 1A is a perspective view of remote access system according to some embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. As used herein, abbreviations can include an automatic update server ("AUS"), system provider laser database ("BLD"), session and log information parser ("SLIP"), tablet software component ("TSC"), web query interface ("WQI"), and web portal server ("WPS").

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Some embodiments of the invention include a dental laser system or network configured with remote access functionality. Some embodiments include dental laser system that can be configured, accessed, and/or updated from a remote network. For example, FIG. 1A is a perspective view of remote access system 10 according to some embodiments of the invention. Some embodiments include a remote access system 10 that can include several components that interact together to acquire data from one or more system provider laser systems, and in some embodiments, can allow users faster and easier access to support and updated content. Some embodiments include a remote access system 10 that can enable trend analysis of field usage. In some embodiments, the system 10 works with all network capable dental and medical laser systems such as a dental laser station 15. In some embodiments, the remote access system 10 can include a coupled dental laser that includes wireless communication circuitry. For example, in some embodiments, a power supply and control module of the coupled dental laser can include the wireless communication circuitry to receive a signal to communicate with a network. While many embodiments of the invention are described as dental laser systems, it should be understood that such descriptions are for the sake of brevity and should not limit any claim scope to exclude other laser systems including a wide array of medical laser systems useful in, without limitation, ophthalmology, aesthetic procedures, general surgery and the like.

In some embodiments of the invention, the dental laser station 15 can include a dental laser 15a that includes at least one display 15b. In some embodiments of the invention, the display 15b can include a graphical user interface (hereafter "GUI") configured to display information related to the operation and function of the dental laser station 15 and any peripheral or component coupled to the dental laser station 15. For example, in some embodiments, the dental laser station 15 can display one or more menus that can include operational parameters of one or more functions of a dental laser station 15 including that of a coupled laser handpiece. Further, in some embodiments, the dental laser station 15 can display one or more menus that can be navigated by one or more users 11 to control or monitor one or more functions of a dental laser station 15.

In some embodiments of the invention, the display 15b can comprise a touchscreen display. In some embodiments, the display 15b can comprise a touchscreen display configured to enable users 11 to interact with the displayed GUI. In some embodiments, user interactions with the GUI can include contact of at least a portion of the display 15b to initiate or represent an input to the display 15b and/or an input or selection of any information within the display or GUI. For example, in some embodiments, one or more users 11, using single, multiple, or repeated physical contact with the display 15b can initiate one or more functions of the dental laser station 15. In some embodiments, using one or more portions of the GUI, users 11 can enter, select, and/or modify one or more system or operational variables or attributes of the dental laser station 15. For example, using at least one displayed feature, users 11 can use the GUI to control a plurality of system or operational variables or attributes of the dental laser 15a. In some embodiments, these parameters can be modified interactively to adjust and optimize the operational characteristics of a dental laser 15a prior to starting a dental procedure, during a dental procedure, and/or after a dental procedure has been performed.

In some embodiments of the invention, the dental laser station 15 can comprise at least one gesture sensor. In some embodiments, the dental laser station 15 can comprise at least one gesture sensor configured to enable users 11 to interact with the at least one gesture sensor and/or the displayed GUI. In some embodiments, user interactions with the at least one gesture sensor can correlate to an update or change to least a portion of the display 15b and/or function of the dental laser station 15, and can initiate or represent an input to the display 15b and/or an input or selection of any information within the display or GUI. For example, in some embodiments, one or more users 11, using single, multiple, or repeated gestures can initiate one or more functions of the dental laser station 15. In some embodiments, using one or more gestures, users 11 can enter, select, and/or modify one or more system or operational variables or attributes of the dental laser station 15. For example, using at least one displayed feature, users 11 can use one or more gestures to control a plurality of system or operational variables or attributes of the dental laser 15a. In some embodiments, these parameters can be modified interactively to adjust and optimize the operational characteristics of a dental laser 15a prior to starting a dental procedure, during a dental procedure, and/or after a dental procedure has been performed.

In some embodiments of the invention, one or more displayed menus of a GUI displayed on the display 15b can include category functions or buttons, any one of which can have one or more control system attributes. In some embodiments, these category buttons can be defined as, but not limited to, dentin, enamel, anterior deciduous, hemostasis, perio (periodontal), endo (endodontic), incision/excision, de-sensitization and osseous. In some embodiments, the display 15b can comprise buttons that can be graphically rendered in a GUI, and/or can be physical buttons located adjacent the displays on a dental tool or associated control equipment, and/or a remote control or a WiFi linked system (e.g., such as a network 17 coupled to one or more servers 20 through internet access point 16). Some further embodiments include other physical buttons or controls that can be used to control one or more functions of the dental laser station 15 including aforementioned gesture controls.

In some embodiments of the invention, the aforementioned power supply and/or control module of the dental laser station 15 can include wireless communication circuitry that is configured to receive at least one signal to communicate with a wireless remote control. In some embodiments, the wireless remote control can be used to actuate a laser output of a handpiece assembly of the dental laser station 15 (e.g., such as the handpiece assembly 29 shown in FIG. 1B). Further, in some embodiments, the wireless remote control can be used to send various control signals from the power supply and control module to the handpiece assembly, or otherwise control one or more operations of the handpiece assembly (e.g., such as handpiece assembly 29). In some embodiments, the wireless remote control can be, in a non-limiting example, a smartphone or a tablet computer (e.g., that is able to communicate wirelessly with the wireless communication circuitry.

In some embodiments, the dental laser station 15 can be supported, mounted and/or coupled to a cart and/or a table (not shown). In some embodiments of the invention, the cart and/or table can comprise a cabinet and/or drawer assembly including drawers and/or cabinet space for storage of miscellaneous supplies, tools, and/or accessories. In some embodiments, using a vertical adjustment, the height of the cart can be adjusted to enable the table to be raised and lowered with respect the cabinet or drawer assembly. Some embodiments include an adjustment column that can be used to facilitate changing the distance of the table with respect to the top end of the cabinet or drawer assembly. In some embodiments, the table can be fixed to the adjustment column, and the column can be configured to slide into and out of the cabinet or drawer assembly. In some other embodiments, the column can be configured in a fixed position with respect to the assembly, and the table can be raised and lowered relative to the column with respect to the assembly to raise or lower the dental laser station 15. In some embodiments, the length of the column or the travel distance of the table can be extended or reduced to enable the distance between the table and the assembly to vary depending on requirements or preferences of the users 11 requirements. In some embodiments of the invention, the cart and/or table can include one or more conventional batteries or other power supply modules. In some embodiments, any mounted or coupled conventional batteries or other power supply modules can provide a sustained, intermittent or on-demand power for the dental laser station 15, or any device or component coupled to or associated with the dental laser station 15. In some other embodiments, the cart and/or table can include at least one conventional compressor and/or at least one source of conventional compressed gas. In some other embodiments, the cart and/or table can include at least one conventional water cleaning and sterilization module. Further, in some embodiments, the cart and/or table can include a source of sterile water or other conventional dental aspiration fluid and/or at least one disinfecting fluid, or combinations thereof.

In some embodiments, the dental laser station 15 can include a removable conventional tablet computer. In some embodiments, the dental laser station 15 can include a mounting or docking point for a conventional tablet computer. In some embodiments, the display 15b can comprise a display of the tablet computer. In some embodiments, the display 15b can be used as a communication tool. In some embodiments, users 11 can communicate to and/or from another user, a trainer, a doctor or dentist, and/or one or more patients using the tablet. For example, in some embodiments of the invention, the dental laser station 15 can comprise the dental laser station 25 shown in FIG. 1B. In some embodiments, the dental laser station 25 can include a removable custom or conventional computing device 26, and a wired and/or wirelessly coupled handpiece assembly 29. In some embodiments, the computing device 26 can comprise the aforementioned tablet computer. In some embodiments, the dental laser station 25 can comprise a tablet display 250 of the computing device 26. In some embodiments, the tablet display 250 comprises a touchscreen display. For example, in some embodiments, the tablet display 250 can comprise a touchscreen display configured to enable one or more users 11 to interact with the displayed GUI.

In some embodiments of the invention, the tablet display 250 can include a GUI comprising at least one displayed menu that can be accessed by users 11 to control or monitor one or more functions of dental laser station 25. In some embodiments, the menus can include category buttons, any one of which can have one or more control system attributes, and can be defined as, but not limited to, dentin, enamel, anterior deciduous, hemostasis, periodontal, endodontic, incision/excision, de-sensitization and osseous. In some embodiments, the display can include various virtual buttons or icons and/or the dental laser station 25 can include physical buttons that can be used to control or access one or more functions of the dental laser station 25.

In some embodiments, the computing device 26 can be used as a training and/or educational tool (e.g., for use as a display for educational videos and/or training materials including text, images, and/or video). In some embodiments, any of the educational videos and/or training materials can include accompanying sound that can be played through the computing device 26 or other audio-capable component coupled to the dental laser station 25. In some embodiments, the audio and video content can automatically be selected based on the context of the any information displayed on the display 250, and can provide highly relevant content to the situation faced by users 11. In some further embodiments, the computing device 26 can be used as a communication tool. In some embodiments, users 11 can communicate to and/or from another user, a trainer, a doctor or dentist, and/or one or more patients using the computing device 26.

In some embodiments, user interactions with the display 250 can include contact of at least a portion of the display 250 to initiate or represent an input to the display 250 and/or an input or selection of any information within a GUI of the display 250. For example, in some embodiments, using single, multiple, or ongoing physical contacts with the display 250, users 11 can initiate one or more functions of the dental laser station 25. In some embodiments, using one or more portions of the display 250, users 11 can enter, select, and/or modify one or more system or operational variables or attributes of the dental laser station 25. For example, using at least one displayed feature, users 11 can use the display 250 to control a plurality of system or operational variables or attributes of the dental laser station 25. In some embodiments, these parameters can be modified interactively to adjust and optimize the operational characteristics of a dental laser station 25 prior to starting a dental procedure, during a dental procedure, and/or after a dental procedure has been performed.

In some embodiments, the dental laser station 25 can include a variety of different lasers, laser diodes, or other sources of light. In some embodiments, the laser sources can include an erbium, yttrium, aluminum garnet (Er:YAG) solid state laser; a chromium, thulium, erbium, yttrium, aluminum garnet (CTE:YAG) solid state laser; an erbium, yttrium orthoaluminate (Er:YAL03) solid state laser; a holmium, yttrium, aluminum garnet (Ho:YAG) solid state laser; a quadrupled neodymium, yttrium, aluminum garnet (quadrupled Nd:YAG) solid state laser; an excimer laser; or a carbon dioxide ($CO_2$) laser. In some further embodiments of the invention, the dental laser can include one or more erbium, chromium, yttrium, scandium, gallium garnet lasers (Er:Cr:YSGG).

In some embodiments, the power supply and/or control module of the dental laser station 25 can include the wireless communication circuitry to receive a signal to communicate with a wireless remote control. For example, in some embodiments, the wireless remote control can be used to actuate a laser output of the handpiece assembly 29 of the dental laser station 25. In some embodiments, the wireless remote control can be used to send various control signals from the power supply and control module to the handpiece assembly 29, or otherwise control one or more operations of the handpiece assembly 29. In some embodiments, the wireless remote control can be, in a non-limiting example, a smartphone or a tablet computer that is able to communicate in a wirelessly with the wireless communication circuitry. In some embodiments of the invention, the wireless remote control can be embodied in the computing device 26.

Figure 1B:
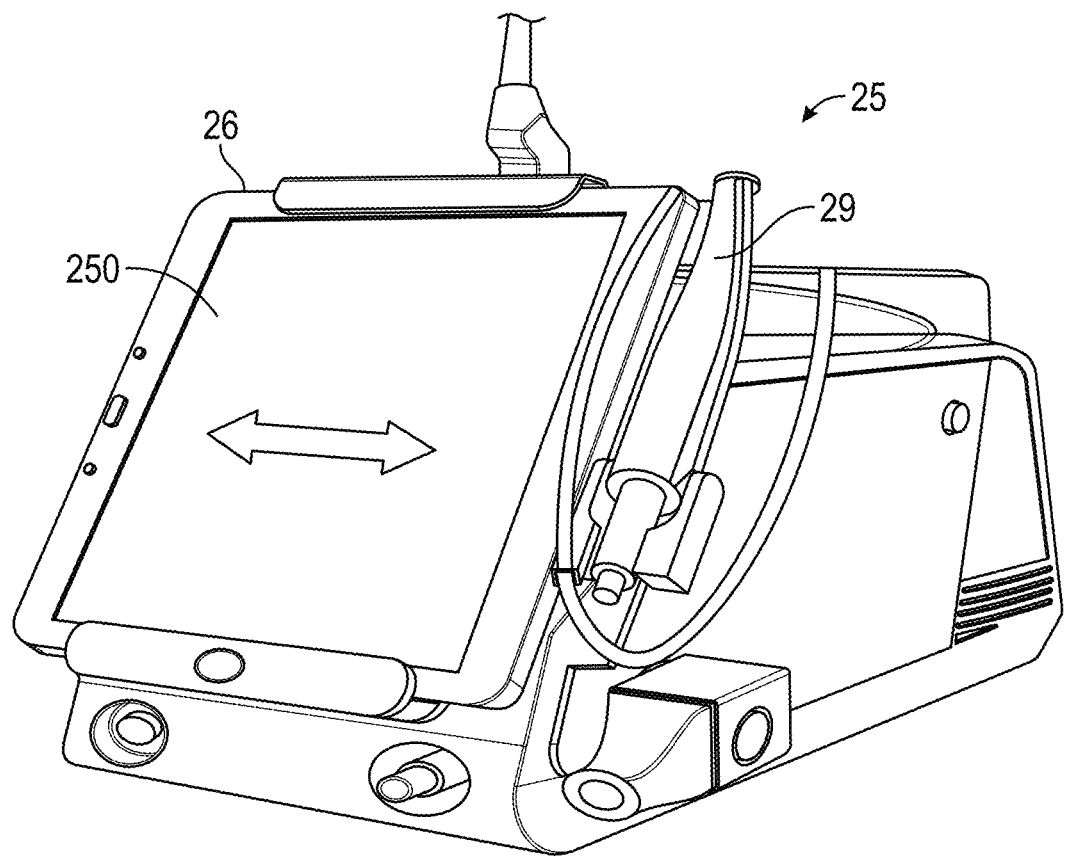
FIG. 1B depicts a dental laser station including a removable tablet computer with a display configured for rendering of a GUI in accordance with some embodiments of the invention.
Figure 2:
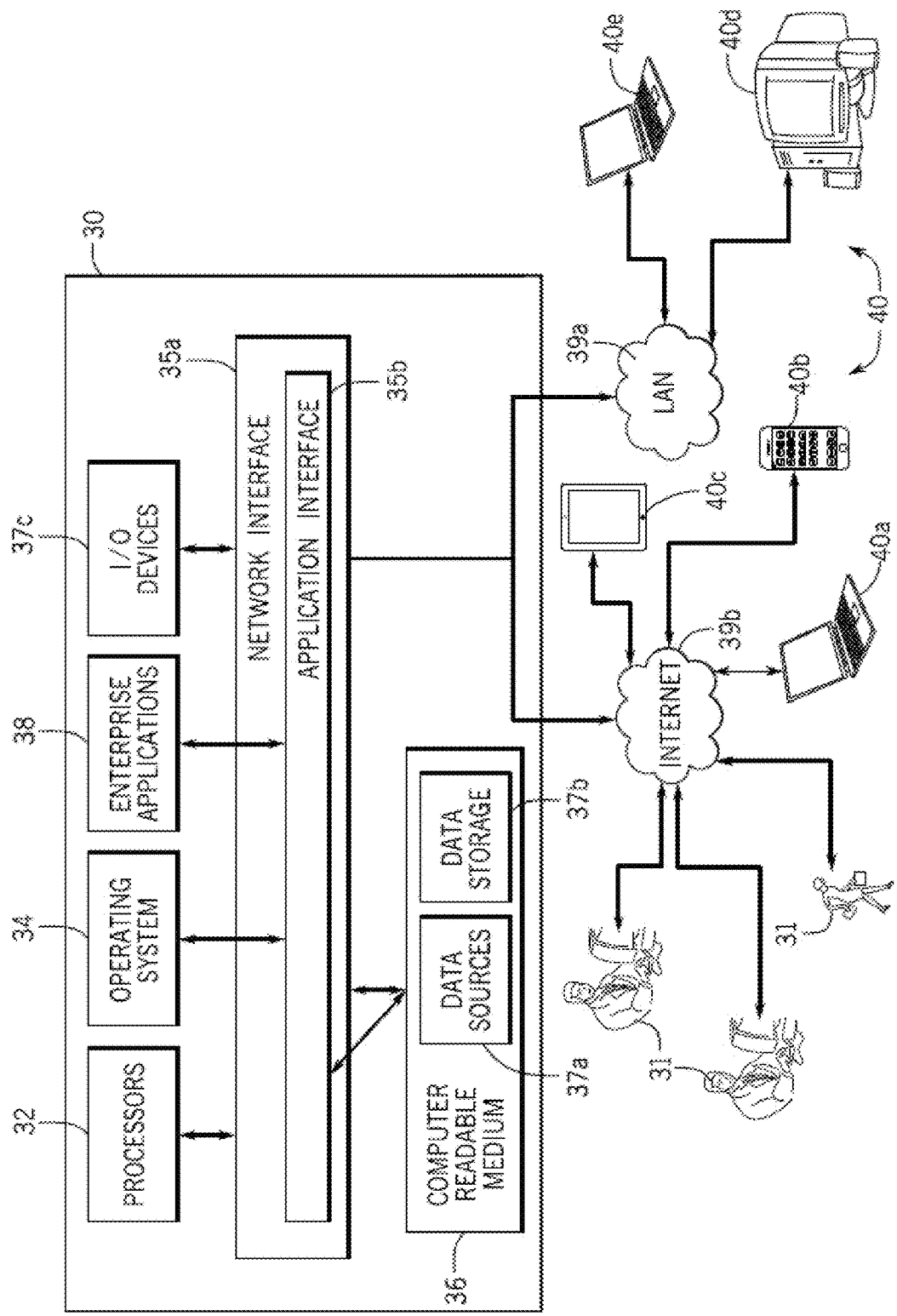
FIG. 2 illustrates a computer system useful for controlling and/or networking to a dental laser station shown in FIG. 1B and/or for operating or forming part of the system of FIG. 1A in accordance with some embodiments of the invention.

FIG. 2 illustrates a computer system 30 that can be used for controlling and/or networking to a dental laser station shown in FIG. 1B and/or for operating or forming part of the system of FIG. 1A in accordance with some embodiments of the invention. In some embodiments, the system 30 can control one or more components or systems of a dental laser station including any operation portion of a remote access function of the dental laser station. In some embodiments of the invention, the system 30 can comprise operating and processing modules for operating the remote access system 10. In some embodiments, using the system 30, the remote access system 10 can manage the organization of data and data flow between the various components of a dentistry control system of the dental laser station 15. In some embodiments, the system 30 can include at least one computing device including one or more processors 32. Some processors 32 can include processors residing in one or more conventional server platforms including within a cloud of computing resources. In some embodiments, the system 30 can include a network interface 35a and/or an application interface 35b coupled to at least one processor 32 capable of running at least one operating system 34. Further, in some embodiments, the at least one processor 32 can be capable of running one or more of the software modules (e.g., such as enterprise applications 38). In some embodiments, the system 30 can comprise at least one computer readable medium 36 coupled to at least one data storage device 37b, and/or at least one data source 37a, and/or at least one input/output device 37c. In some embodiments, the computer readable medium 36 can be any data storage device that can store data, which can thereafter be read by a computer system (such as the system 30). Examples of the computer readable medium 36 can include hard drives, network attached storage (NAS), read-only memory, random-access memory, FLASH based memory, CD-ROMs, CD-Rs, CD-RWs, DVDs, magnetic tapes, other optical and non-optical data storage devices, or any other physical or material medium which can be used to tangibly store the desired information or data or instructions and which can be accessed by a computer or processor (including processors 32).

Some embodiments include at least a portion of the remote access system 10 embodied as computer readable code on the computer readable medium 36. In some embodiments of the invention, the computer readable medium 36 can also be distributed over a conventional computer network via the network interface 35a so that the computer readable code can be stored and executed in a distributed fashion. For example, in some embodiments, one or more components of the system 30 can be tethered to send and/or receive data through a local area network ("LAN") 39a. In some further embodiments, one or more components of the system 30 can be tethered to send or receive data through an internet 39b (e.g., a wireless internet). Further, in some embodiments, at least one software application 38 running on one or more processors 32 can be configured to be coupled for communication over a network 39a, 39b. In some embodiments, one or more components of the network 39a, 39b can include one or more resources for data storage, including any other form of computer readable media beyond the media 36 for storing information and including any form of computer readable media for communicating information from one electronic device to another electronic device.

In some embodiments, the network 39a, 39b can include wide area networks ("WAN"), direct connections (e.g., through a universal serial bus port) or other forms of computer-readable media 36, or any combination thereof. Further, in some embodiments, one or more components of the network 39a, 39b can include a number of client devices which can be one or more computers 40 including for example desktop computers 40d, laptop computers 40a, 40e, digital assistants and/or personal digital assistants (shown as 40c), cellular phones or mobile phones or smart phones (shown as 40b), pagers, digital tablets, internet appliances, and other processor-based devices. In general, a client device can be any type of external or internal devices such as a conventional mouse, CD-ROM, DVD, keyboard, display, or other input or output devices 37c. In some embodiments, various other forms of computer-readable media 36 can transmit or carry instructions to one or more computers 40, including a router, private or public network, or other transmission device or channel, both wired and wireless. In some embodiments, the software modules 38 can be configured to send and receive data from a database (e.g., from a computer readable medium 36 including data sources 37a and data storage 37b that can comprise a database), and data can be received by the software modules 38 from at least one other source.

In some embodiments, at least one of the software modules 38 can be configured within the system 30 to output data to at least one user 31 via at least one digital display (e.g., to a computer comprising a digital display). In some embodiments, any users 11 can comprise the at least one user 31. In some embodiments, the display can include the display 250 of the dental laser station 25 depicted in FIG. 1B. In some embodiments, the system 30 as described can enable one or more users 31 to receive, analyze, input, modify, create and send data to and from the system 30, including to and from one or more enterprise applications 38 running on the system 30. Some embodiments include at least one user 31 coupled to a computer 40 accessing one or more modules of the dentistry control system including at least one enterprise applications 38 via a stationary I/O device 37c through a LAN 39a. In some other embodiments, the system 30 can enable at least one user 31 (through computer 40) accessing enterprise applications 38 via a stationary or mobile I/O device 37c through an internet 39a. In some embodiments, the software modules 38 can include a server-based software platform that can include dentistry control software modules suitable for hosting at least one user 31 account and/or at least one patient account or record. In some embodiments, using the system 30, the dentistry control system and method can manage multiple user accounts and/or multiple patient accounts.

Some embodiments include a remote access system 10 that can include a remote access feature allowing real time access to any connected laser system using a mobile display of a computing device 26 (e.g., such as a mobile display of a smartphone or computer or mobile terminal). In some embodiments of the invention, one or more components of the computing device 26 can include an interface for the users 11 to connect to a Wi-Fi network. In some further embodiments of the invention, the computing device 26 can provide a web portal for users 11 to share information and best practices. In some further embodiments of the invention, the computing device 26 can integrate with system provider systems for automated ordering, etc. (e.g., such as CRM and ERP order management systems). In some further embodiments of the invention, the remote access system 10 can scale to support all future system provider web-enabled laser systems.

Some embodiments include a remote access system 10 that can receive session and log data from any connected system at a specific time and at specific intervals. For example, some embodiments include a remote access system 10 that is configured to receive one or more session and log data from any connected system about twice per week. This frequency can vary based on one or more user settings, or the remote access system 10 can set or vary the frequency based on one or more parameters of the remote access system 10. In some embodiments of the invention, the session data can include information related to one or more procedures, and/or settings information, and/or errors, as well as time spent firing the laser. In some embodiments, the log data can include all events (screen presses, etc.) in addition to raw communication data. In some embodiments, reports and metrics 21 of the remote access system 10 can include any of the session data described.

Some embodiments include a remote access system 10 that can receive intermediate data via a "Help Me Now" feature which appends a current log file and that is sent to a system provider. In some embodiments, other data can be sent or received and appended to the log file based on any system input or output. Some embodiments include a remote access system 10 that includes a remote access feature which allows real time access to any coupled laser system (e.g., such as dental laser station 15). Some embodiments include a remote access system 10 that can allow download of updated training materials, videos, software, and firmware updates over the air (e.g., through interne access point 16). Some embodiments include a remote access system 10 that also includes a user dashboard and discussion forum. In some embodiments, on the system provider side, some embodiments include a remote access system 10 that allows all received data to be queried arbitrarily for data mining and analysis purposes as well as review of device or user history.

In some embodiments of the invention, the remote access system 10 can function to address various system provider remote access requirements. For example, in some embodiments, the remote access system 10 can provide access to field data for error analysis and usage trending. Further, some embodiments of the invention can enable near instantaneous customer support features (shown as 22).

In some embodiments of the invention, the remote access system 10 can provide automated alerts when any component or system of the remote access system 10 experiences an error. In some further embodiments of the invention, the remote access system 10 can provide automated software and content updates (e.g., from one or more servers 20).

In some embodiments, one or more system or software updates can be uploaded or downloaded through a wired and/or wireless connection of the remote access system 10 (e.g., from the network 17). For example, in some embodiments, remote access system 10 can receive at least one automated software and content update via an internet connection (network 17) that is enabled using a wired and/or wireless connection (internet access point 16).

Some embodiments include a computing device 26 that can allow a download of updated training materials, videos, software, and firmware updates over the air. Some embodiments include a computing device 26 that also includes a user dashboard and discussion forum. On the system provider side, some embodiments include a computing device 26 that allows all received data to be queried arbitrarily for data mining and analysis purposes as well as review of device or user history. In some embodiments of the invention, the computing device 26 can function to address various system provider remote access requirements. For example, in some embodiments, the remote access system 10 can provide access to field data for error analysis and usage trending. Further, some embodiments of the invention can enable near instantaneous customer support features. In some embodiments of the invention, the computing device 26 can provide automated alerts when any component or system of the remote access system 10 experiences an error.

In some further embodiments of the invention, the computing device 26 can provide automated software and content updates. In some embodiments, one or more system or software updates can be uploaded or downloaded through a wired and/or wireless connection of the computing device 26. For example, in some embodiments, the computing device 26 can receive at least one automated software and content update via an internet connection that is enabled using a wired and/or wireless connection.

In some embodiments, the computing device 26 can be used to control and function as an interactive educational tool to perform complex clinical procedures. In some embodiments of the invention, prior to the use of a medical system for any particular clinical procedures, the computing device 26 can be "locked" for a given user, and the system can request the user to perform interactive or other types of training. In some embodiments, any particular procedure can be unlocked only after the user successfully passes the required training (e.g., in the form of one or more training modules configured for interactive display on the tablet computer). In reference to FIGS. 1A and 1B, in some embodiments of the invention, the system 10 can perform an analysis of one or more clinical cases through comparative analysis of the clinical images of the particular clinical case with one or more images stored in the system memory. In some embodiments of the invention, after analysis of the clinical images, the system 10 can recommend specific protocols and settings to perform this particular clinical treatment.

In some embodiments, the system 10 can prepare a recording of the patient feedback (e.g. after any clinical procedure). In some embodiments, this feedback can be used for multiple purposes, including, but not limited to, demonstration of the superiority of particular clinical treatment technology and protocol over the conventional methods or other protocols. In some embodiments, this feedback can lead towards optimization of the protocols and further selection "technology of choice" for any treatment. Such feedback can also be used to select highly expert practitioners to train others, to publicly recognize particularly effective practitioners as being unusually expert to gain prestige in the profession, and the like. In some embodiments, the computing device 26 can be used to record patient-reported outcomes, where for example, based on the results of the procedure performed, patient's feelings during and after procedure and their opinions in relation to the previously used and alternative technologies or clinical protocols can be recorded. In some embodiments, once recorded and analyzed, these records can be used to facilitate the selection of the protocols for the doctor as well as to improve parameters and settings within particular protocols.

In some embodiments, the system 10 can enable standardization of clinical recommended settings and protocols, as well as unification of the feedback data when applied within certain network of medical clinics. In some embodiments of the invention, all systems utilization data as well as new recommendations can be controlled and consolidated within certain networks, used to improve educational programs, customer support, sales and marketing initiatives. In some embodiments of the invention, this function can also imply in providing "fee for service" type of the use of medical systems and facilitate low-cost introductory of the new technology and medical device as well as ensure sustaining long-term income for the service provider. In some embodiments, it can identify "under-utilization" as well as misuse of the devices with implementation of further corrective actions and analysis of their effectiveness.

Some implementations of the abovementioned functions can include, but not be limited to, interactive training, and/or image-based clinical recommendations, and/or record patient's outcome, and/or utilization within the clinical networks. For utilization within clinical networks, the introduction of the new technology within the network of medical clinics can act as a differentiator as well as a competitive advantage. In some embodiments, the use of the computing device 26 can allow not only provide consistent education and training within the network, but also allow optimization of clinical utilization based on the specifics of the given network environment. Such utilization can be different from any other and may require unique aspects of support or business management to ensure success. For example, for interactive training, the system 10 can have multiple loaded procedures, which can be altered, uploaded or deleted remotely by the manufacturer, one or more of which can include an interactive function. If a particular user has not been certified to use any particular procedure, it can be "locked" on the user's system. "Unlocking" can be allowed only after successful on-board educational and training session, which will include not only answering the questions, but also performing certain manipulations using clinical animations. This process can be initiated and monitored by the manufacturer.

Further, for image-based clinical recommendations, the system 10 can have multiple clinical images loaded in its memory. Any particular clinical case in medical practice can be photographed and comparatively analyzed through pattern recognition function with the images in system memory. In some embodiments, clinical recommendations, using "best clinical practices" can then be suggested to the clinician or practitioner to make a treatment decision. In some embodiments, these recommendations can include a suggestion to use or not use system technology for particular treatment and/or options to select a particular best-fitting clinical protocol and system settings to ensure best clinical outcome.

Some embodiments include the use of one or more identification or notification icons or other rendered graphics displayed on a GUI of the computing device 26 of the dental laser station 25. In the following discussion, any described GUI, display, or component or image can be displayed on the display 250 of the computing device 26 when described as the system 10. For example, when described in terms the system 10, any GUI, display, or component or image (e.g., such as an icon or a portion of a displayed image) described herein can be displayed on the display 250 of the computing device 26, and/or on any display coupled to and/or forming part of the system 10.

Figure 3:
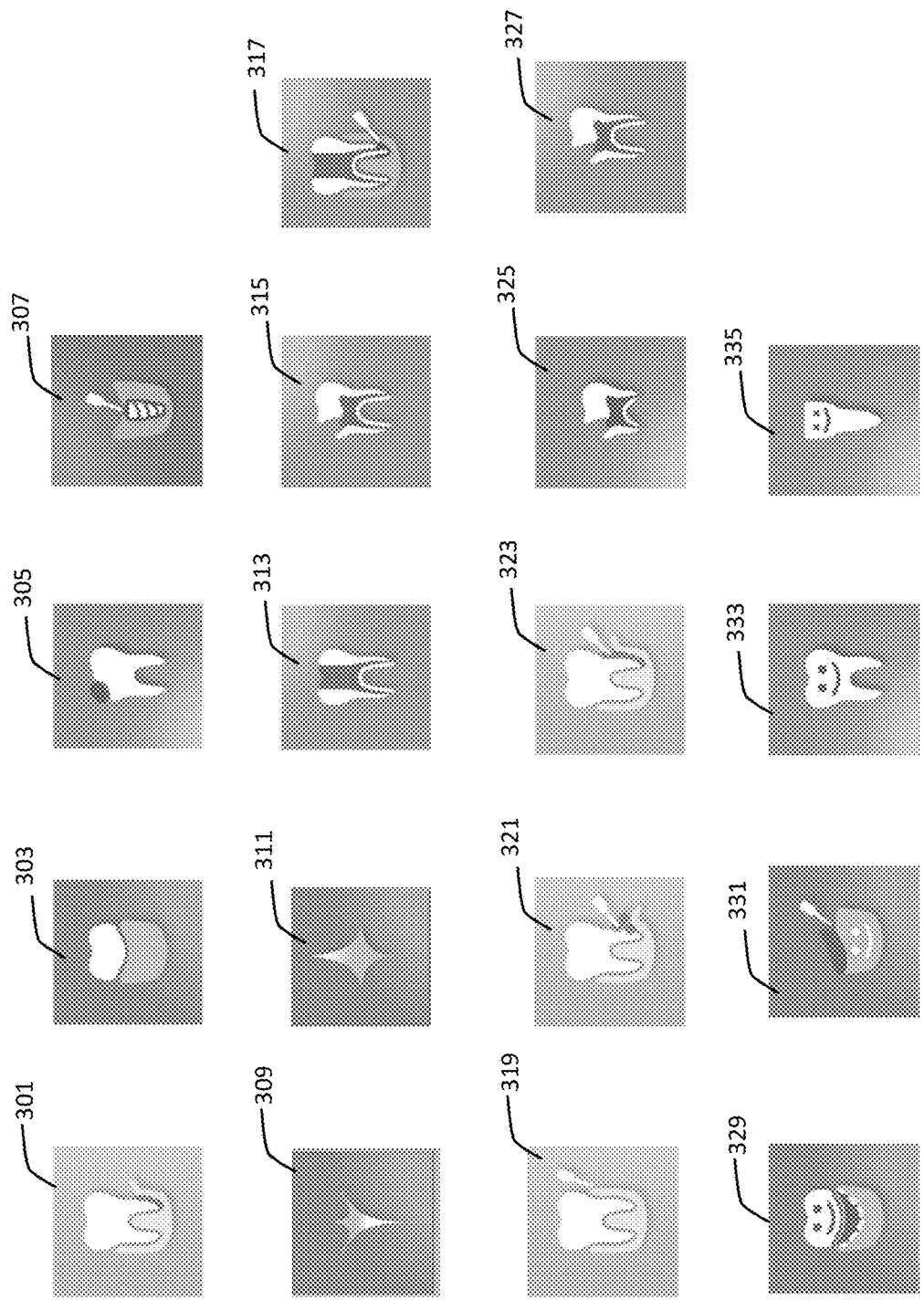
FIG. 3 shows GUI icons displayable on the dental laser station of FIG. 1B in accordance with some embodiments of the invention.
Figure 5:
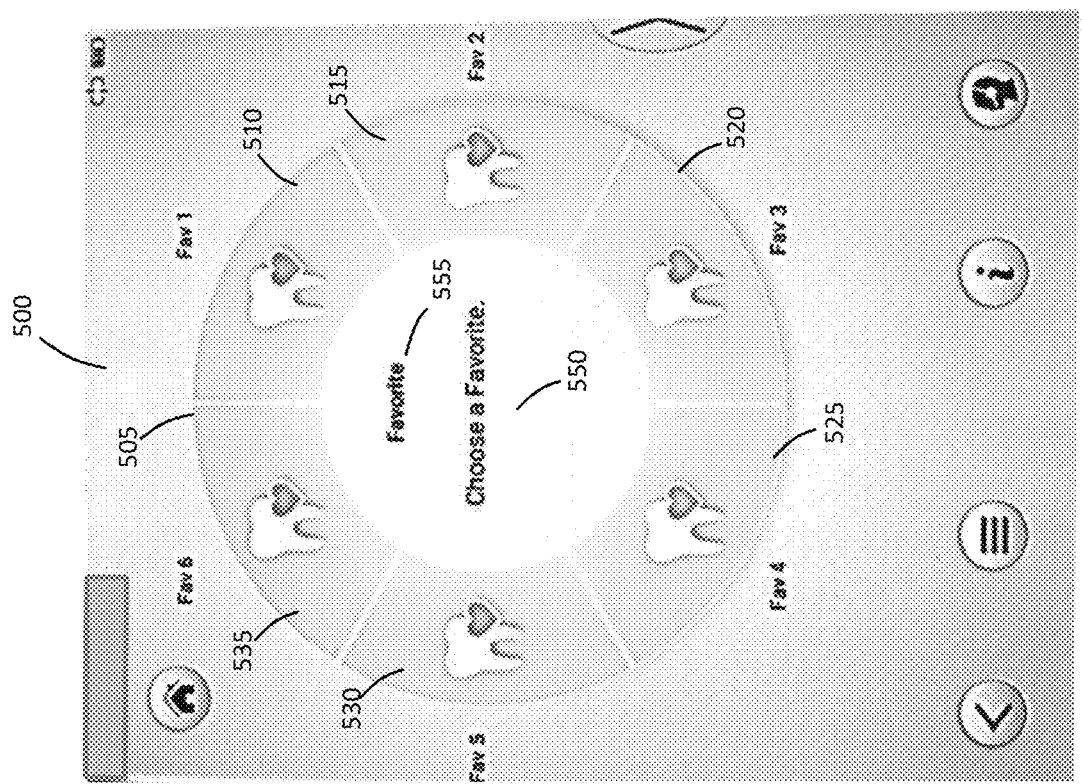
FIG. 5 illustrates a favorites selection GUI display in accordance with some embodiments of the invention.

In some embodiments, the identification or notification icons can provide a tie between the user and particular clinical applications. For example, FIG. 3 shows GUI icons 301, 303, 305, 307, 309, 311, 313, 315, 317, 319, 321, 323, 325, 327, 329, 331, 333, 335 displayable on computing device 26 of the dental laser station 25 of FIG. 1B in accordance with some embodiments of the invention. In some embodiments, one or more features or aspects of any one of the icons 301, 303, 305, 307, 309, 311, 313, 315, 317, 319, 321, 323, 325, 327, 329, 331, 333, 335 can be used or altered to represent a function, action, or feature of the system. For example, in some embodiments, the system 10 can display one or more of the icons 301, 303, 305, 307, 309, 311, 313, 315, 317, 319, 321, 323, 325, 327, 329, 331, 333, 335 in one or more colors. In some embodiments, each category of procedures related to a particular field can include a unique identification color. In some embodiments, the color can be related to some clinical aspects of a clinical category, including, but not limited to: for procedures, where treatment of bone is involved, and the associative color is yellow, the color of the bone; and/or where more blood is involved, the associative color is a shade of red or orange (different from a red used for emergency situations only), and/or where the treatment of tooth surface is mostly involved, and can be an associative color of light blue.

In some embodiments, one or more of the icons 301, 303, 305, 307, 309, 311, 313, 315, 317, 319, 321, 323, 325, 327, 329, 331, 333, 335 can be used to make an associative connection with any one or more clinical applications and/or a specific step within the application. In some embodiments, one or more of the icons 301, 303, 305, 307, 309, 311, 313, 315, 317, 319, 321, 323, 325, 327, 329, 331, 333, 335 can be detailed enough to enable observation of differences or similarities in an application or a step. In some embodiments, one or more icons 301, 303, 305, 307, 309, 311, 313, 315, 317, 319, 321, 323, 325, 327, 329, 331, 333, 335 can be indicative of clinical relevancy. In some embodiments, one or more icons 301, 303, 305, 307, 309, 311, 313, 315, 317, 319, 321, 323, 325, 327, 329, 331, 333, 335 can reflect any real clinical situation, enabling a minimum of or no associative disconnect or blockage between the expert user's mind and clinical meaning of the identification icon.

In some embodiments, the structure and/or detail included in any one of the icons 301, 303, 305, 307, 309, 311, 313, 315, 317, 319, 321, 323, 325, 327, 329, 331, 333, 335 can be indicative of the level of clinical procedure (e.g., such as the level of detail), and when identification of a particular procedure step is shown, and/or where specific technique is described, the icons are generally include more detailing and/or structure or information.

In some embodiments, one or more of the icons 301, 303, 305, 307, 309, 311, 313, 315, 317, 319, 321, 323, 325, 327, 329, 331, 333, 335 can include a commonality. In some embodiments, within each clinical category, all icons can generally include the same common general symbol, and details of procedures can be depicted around the general symbol. In some embodiments, steps can be common between different clinical categories, having different identification colors and different general symbols. In that case, the use of the secondary symbols can be used to emphasize those commonalities.

In some embodiments, periodontal applications can involve in most cases treatment of the jaw bones, which has yellow color, and so in some embodiments, the icon 301 can be yellow. Treatment of soft tissues is associated in most cases with blood, and so in some embodiments, the icon 303 can be a shade of red. The treatment of the tooth itself is mostly the enamel, and in some embodiments, the icon 305 can be a shade of blue. The treatment of periodontal diseases is involved with multiple types of tissue: tooth itself, jaw bone, gum (soft tissue), and in some embodiments, the icon 307 can combine bone and soft tissue in the icon.

In some embodiments of the invention, one or more icons can be arranged based on the clinical relevancy of a specific procedure, option, step, or method. In some embodiments, images can be reviewed and corrected by a group of clinical experts within multiple disciplines, different levels of academic/scientific and practical hands-on experience, and practicing in many countries. For example, in soft tissue/frenectomy, the system 10 can distinguish between maxillary frenectomy (cutting the lip frenum) (represented as icon 309), and lingual frenectomy (cutting of the tongue frenum) (represented as icon 311).

In some embodiments of the invention, there can be different levels of clinical applications. For example, in some embodiments of the invention, there can be three levels of clinical applications, including "level 0—clinical category", "level 1—a particular clinical application within this category", and "level 2—a specific step of the procedure or option to perform this procedure". In some embodiments of the invention, at level 0, the system 10 can show a common general icon of the area involved (e.g., in endo—root canals). In some embodiments, at level 1, the system 10 can generally show clinical conditions of the particular clinical application (in endo/pulp cap≥exposure of the tooth nerve). In some embodiments, at level 2, the system 10 can show how to approach treatment of these conditions (in endo/apicoectomy/osseous access—getting laser tip at the apex of the root). For example, level 0 in endodontics: (shown as icon 313), level 1: (shown as icon 315), and level 2: (shown as icon 317). In some embodiments, within a clinical category, the system 10 can generally try to keep the same main icon, e.g., such as periodontal level 2 for outline: (shown as icon 319), degranulation: (shown as icon 321), and root debridement: (shown as icon 323).

In some embodiments, in different clinical categories, the system 10 can similarly depict common aspects of clinical conditions, e.g., such as exposed tooth pulp for treatment in deciduous teeth (hard tissue category): (shown as icon 325), and for treatment in the endodontic: (shown as icon 327). In some further embodiments, the system 10 can use common secondary icons for depicting similar approach to treatment technique within different clinical applications. For example, some embodiments include a gentle (shown as icon 329) approach such as a "comfort cut" in soft tissue procedures: (shown as icon 331) and hard tissue procedures: (shown as icon 333) (shown as icon 335). In some embodiments, the comfort cut settings can be selected to decrease pain sensations in a typical patient at the potential expense of slowing other performance characteristics of the system 10.

Figure 4:
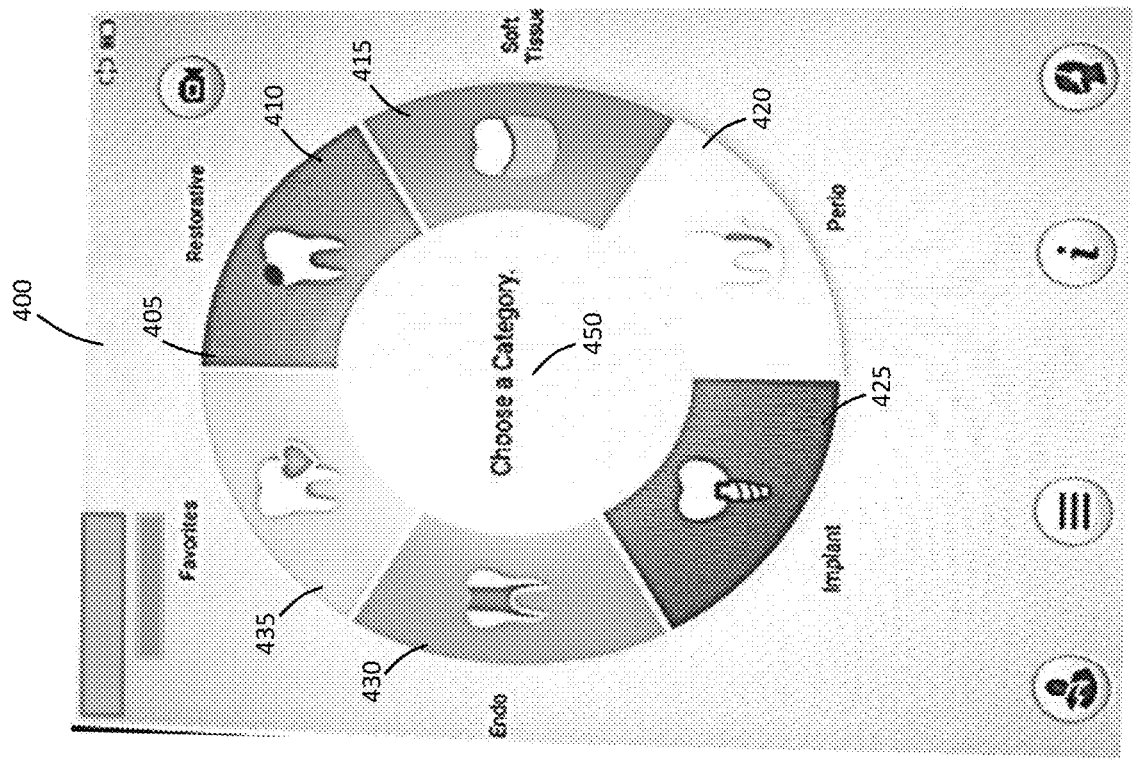
FIG. 4 illustrates a category selection GUI display in accordance with some embodiments of the invention.

In some embodiments, various icons, including, but not limited to any of the icons described above, can be used in various control and information displays. For example, FIGS. 4-36 shows illustrates control and information displays of the display of the dental laser station 25 of FIG. 1B in accordance with some embodiments of the invention. For example, FIG. 4 illustrates a control and information of display 400 including a control wheel 405 with icons or segments representing selectable categories of procedures. In some embodiments, the control wheel 405 is circular. In other embodiments, the control wheel 405 (or any of the control wheels described herein) can be non-circular (i.e., oval, a square, or a rectangle, or triangular). In some embodiments, any of the icons or segments can include a visual icon comprising a banner, graphic, image, text, or combinations thereof. In some embodiments, the visual icon can comprise a notification or description of the underlying segment. In some embodiments, following a user selection of a specific segment or icon, the contents of a variation of the contents of the visual icon of the chosen segment can be displayed in the display 400 such as within the central display 450. Further, in some embodiments, the segment can be identified as being selected (e.g., such as shown in the example embodiments where the segment or icon is shown separated from adjacent segments). In other embodiments, the selected segment can be distinguished by color, shape, size, animation, or any other conventional GUI display format.

In some embodiments, any procedure operated through the control wheel 405 of the display 400 can enable a user to update, select, or modify the control wheel 405, including, for example, to add or subtract category segments or buttons, to modify attribute values, and/or to allow personification of a specific doctor's preference system. The adjustable parameters can include, but not be limited to, laser pulse peak power, laser pulse repetition rate, laser pulse duration, laser average output power, and volume and quality of the cooling water spray or air flow. For example, in some embodiments, the display 400 can include adjustable parameters for the power and pulse of at least one laser source. Other adjustable parameters for control of air, water, aiming, and illumination can also be included. The display 400 can also include one or more numeric displays representing operational parameters (e.g., such as laser power, pulse frequency, percentages of air and water, and percentages of aim and illumination) with and/or adjacent to the central display 450.

In some embodiments, the icons can be arranged as a circle at least partially surrounding the central display 450, where each icon can be selectable to access one or more categories of procedures. In some embodiments, the selectable icons can form or define at least a portion of the control wheel 405. For example, in some embodiments, the selectable icons can form or define at least a portion of the circumference of the control wheel 405 when the control wheel 405 is substantially circular. In other embodiments, when the control wheel 405 is non-circular, the selectable icons can form or define at least a portion of an outer portion or periphery of the shape of the control wheel. In some embodiments, at least some of the icons were described earlier with respect to FIG. 3, including, but not limited to, access icons for restorative procedures 410, access icons for soft tissue procedures 415, access icons for periodontal procedures 420, access icons for implant procedures access 425, and access icons for endodontic procedures 430. Further, some embodiments include icons for favorites procedures (icon 435). In some embodiments, users 11 can use the access icon for restorative procedures 410 to select and/or initiate a restorative procedure. In some embodiments, users 11 can use the access icon for soft tissue procedures 415 to select and/or initiate a soft tissue procedure. In some embodiments, users 11 can use the access icon for periodontal procedures 420 to select and/or initiate a periodontal procedure. In some embodiments, users 11 can use the access icon for implant procedures 425 to select and/or initiate a soft tissue procedure. In some embodiments, users 11 can use the access icon for endodontic procedures 430 to select and/or initiate an endodontic procedure.

In some embodiments, the central display 450 can include a notification or other system message or instruction. For example, in some embodiments, the central display 450 can include a notification of "Choose a Category". In some embodiments, after users 11 select any one of the icons 410, 415, 420, 425, 430, the display 400 can update or change to enable a user to proceed with selections or options within a category or procedure. In some other embodiments, after users 11 select favorites icon 435, display 500 (shown in FIG. 5) can be displayed with a menu control wheel 505 for selection from a plurality of favorite icons. For example, in some embodiments, the menu control wheel 505 can include first favorite 510, and/or second favorite 515, and/or third favorite 520, and/or fourth favorite 525, and/or fifth favorite 530, and/or sixth favorite 535. In some embodiments, the icons can be arranged as a circle at least partially surrounding a central display 550, where each icon can be selectable to access one or more favorites. In some embodiments, the selectable icons can form or define at least a portion of a periphery and/or the circumference of the control wheel 505.

Figure 6:
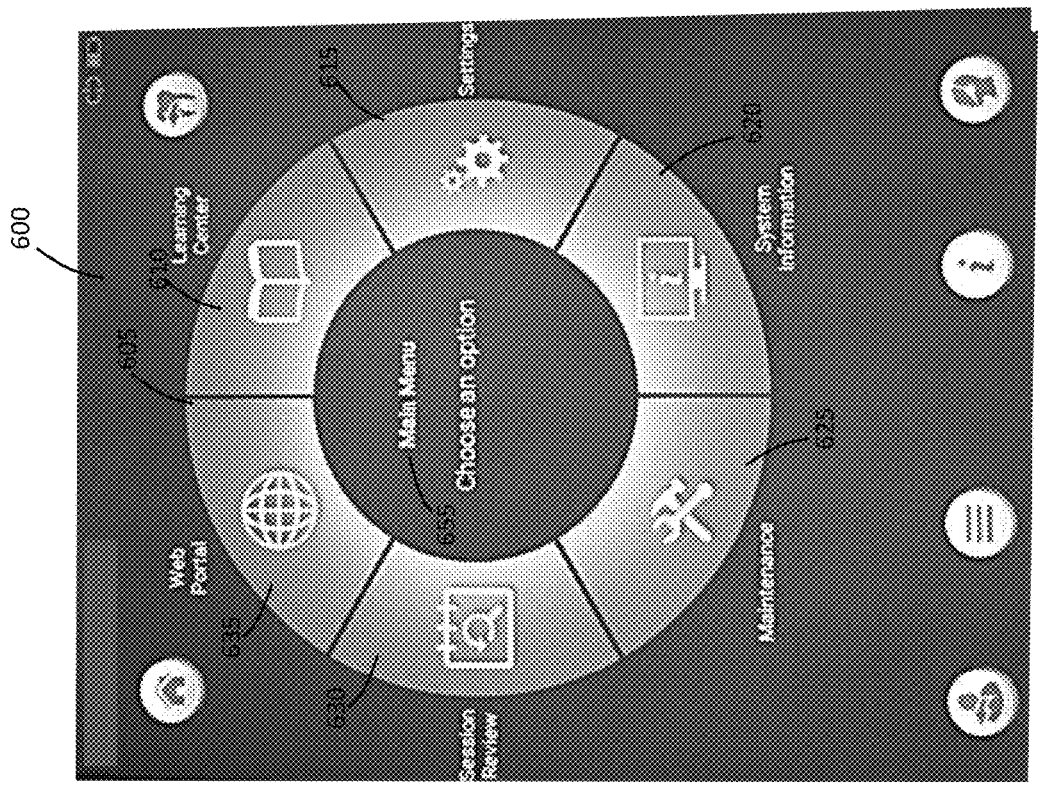
FIG. 6 illustrates a main menu GUI display in accordance with some embodiments of the invention.

Referring to FIG. 6, some embodiments include a display 600 including menu 605 with selectable icons for information and system access, including a learning center icon 610, settings icon 615, system information icon 620, maintenance icon 625, session review icon 630, and web portal access icon 635 selection icon options. In some embodiments, the icons 610, 615, 620, 625, 630, 635 can be arranged as a circle at least partially surrounding a central display 655, where each icon can be selectable to access one or more system features. In some embodiments, the learning center icon 610 can enable users 11 to access learning information related to operation and function of the system 10, and/or for information related to one or more clinical procedures. In some further embodiments, the settings icon 610 can enable users 11 to access settings information related to operation and function of the system 10. In some other embodiments, the system information icon 620 can enable users 11 to access system information related to operation and function of the system 10. In some embodiments, the maintenance icon 625 can enable users 11 to access maintenance information related to operation and function of the system 10. In some embodiments, the session review icon 630 can enable users 11 to access session information related to operations and functions of the system 10 during one or more sessions. In some embodiments, the web portal access icon 635 can enable users 11 to access a web portal of the system 10. In some embodiments, the selectable icons 610, 615, 620, 625, 630, 635 can form or define at least a portion of a periphery and/or the circumference of the control wheel 605. In some embodiments, the central display 655 can include a notification or selectable icon for "Main Menu" that can enable users 11 to prompt the system 10 to display a main menu. In some embodiments, users 11 can access a learning center portion of the system 10 using the learning center icon 610. In some further embodiments, users 11 can access settings and parameters of the system including the settings and parameters of the dental laser station 25 using the setting icon 615. In some further embodiments, the system information icon 620 can be used to access one or more system information procedures, parameters, or processes. In some other embodiments, the maintenance icon 625 can be used to access one or more maintenance procedures, parameters, or processes. In other embodiments, users 11 can use the session review icon 630 to access and review session information. In other embodiments, users 11 can use the web portal access icon 635 to access the internet.

Figure 7:
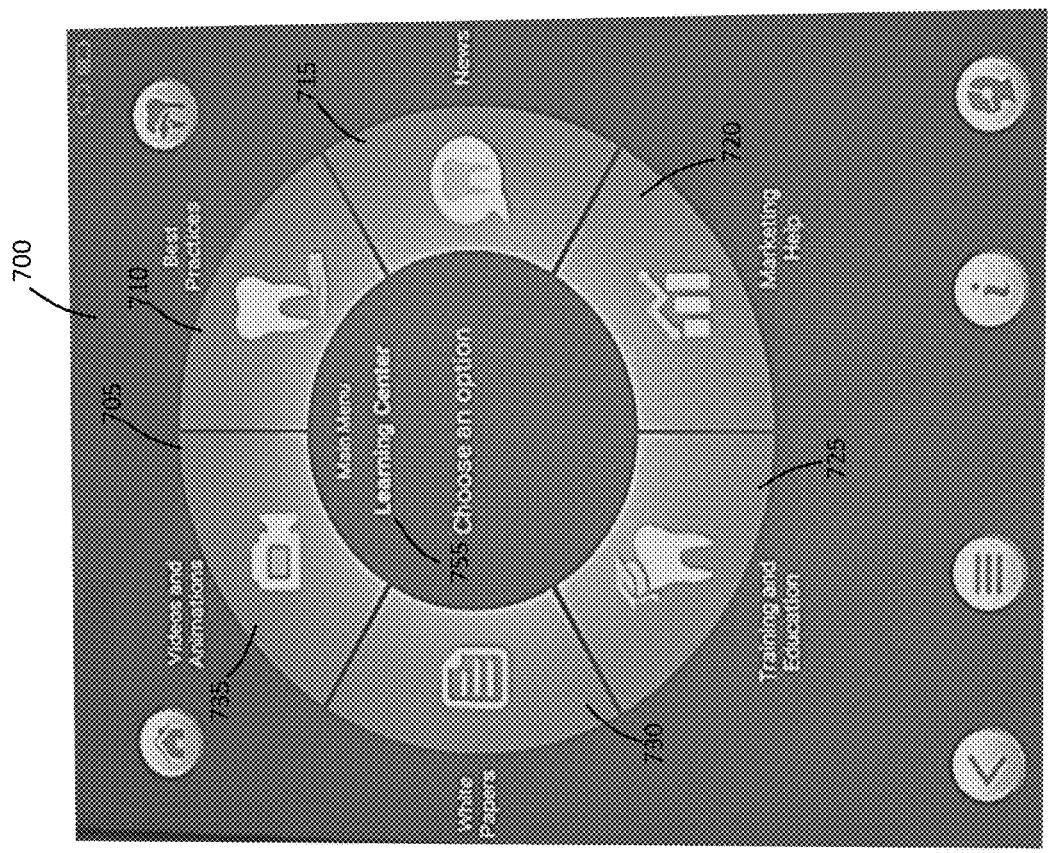
FIG. 7 illustrates a learning center GUI display in accordance with some embodiments of the invention.

In some embodiments of the invention, selection of the learning center icon 610 can enable the display 700 of FIG. 7, including, but not limited to, selectable icons for best practices (selectable icon 710), news (selectable icon 715), marketing help (selectable icon 720), training and education (selectable icon 725), access to white papers (selectable icon 730), and videos and animations selection icon options (selectable icon 735). In some embodiments, the icons 710, 715, 720, 725, 730, 735 can be arranged as a circle at least partially surrounding a central display 755, where each icon can be selectable to access one or more system features. In some embodiments, the selectable icons 710, 715, 720, 725, 730, 735 can form or define at least a portion of a periphery and/or the circumference of the control wheel 705. In some embodiments, the central display 755 can include a notification or selectable icon for "Main Menu" that can enable users 11 to prompt the system 10 to display a main menu. In some embodiments, the selectable icon 710 can enable a user to access information related to best practices, and the selectable icon 715 can enable a user to access information related to news. In some embodiments, the selectable icon 720 can enable a user to access information related to marketing help, and the selectable icon 725 can enable a user to access information related to training and education. In some embodiments, the selectable icon 730 can enable a user to access information related to access to white papers, and the selectable icon 735 can enable a user to access information related to videos and animations related to procedures, clinical methods, and/or operation of the dental laser station 25.

Figure 8:
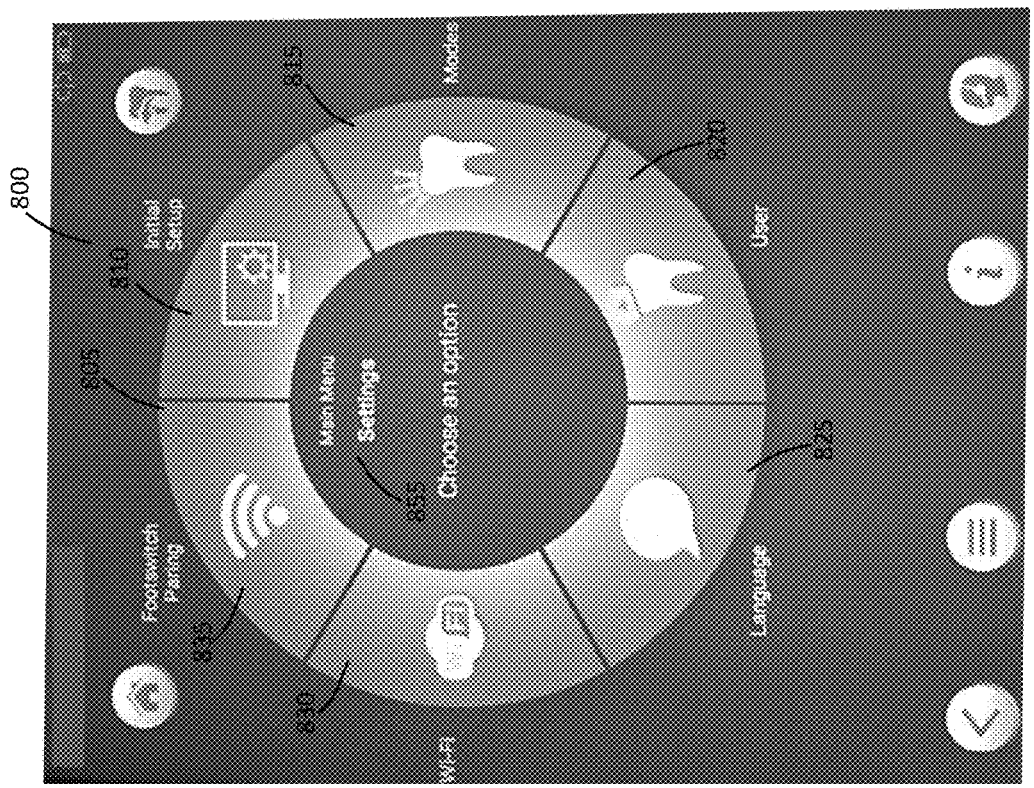
FIG. 8 illustrates a settings GUI display in accordance with some embodiments of the invention.

One further non-limiting example can enable users 11 selection of the settings icon 615 where the system 10 can subsequently provide a display 800 of the control wheel 805 shown in FIG. 8. In some embodiments, the display 800 of FIG. 8 can include initial setup, modes, user, language, Wi-Fi, and footswitch pairing options. For example, some embodiments include a control wheel 805 comprising the initial setup access icon 810, modes icon 815, user icon 820, language icon 825, Wi-Fi icon 830, and a footswitch pairing icon 835. In some embodiments, the icons 810, 815, 820, 825, 830, 835 can be arranged as a circle at least partially surrounding a central display 855, where each icon can be selectable to access one or more system features. In some embodiments, the initial setup access icon 810 can enable users 11 to engage in one or more setup operations. In some further embodiments, modes icon 815 can enable users 11 to switch between two or more modes and/or to select a mode. In some embodiments, user selection can be controlled with user icon 820. In some further embodiments, language icon 825 can be used to adjust or set a preferred language. In some embodiments, the Wi-Fi icon 830 can be used to access or switch Wi-Fi couplings and/or setup. In some embodiments, the footswitch pairing icon 835 can be used to pair and/or access a footswitch. In some embodiments, the selectable icons 810, 815, 820, 825, 830, 835 can form or define at least a portion of a periphery and/or the circumference of the control wheel 805. In some embodiments, the central display 855 can include a notification or selectable icon for "Main Menu" that can enable users 11 to prompt the system 10 to display a main menu. Further, in some embodiments, the central display can include a notification or identification related to the settings menu (i.e., to alert users of the type or function of the displayed menu).

Figure 9:
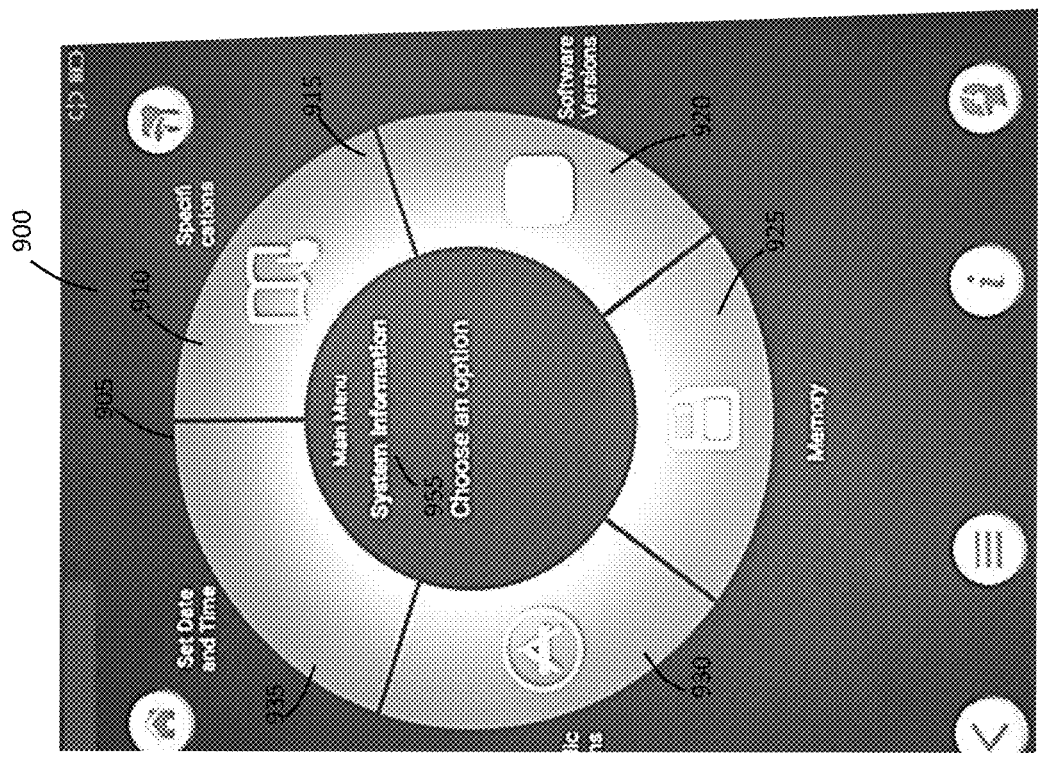
FIG. 9 illustrates a system information GUI display in accordance with some embodiments of the invention.

In some embodiments, selection of the system information icon 620 (FIG. 6) can enable the display 900 shown in FIG. 9 of a control wheel 905 including miscellaneous specification icon 910, software version icon 920, memory icon 925, application icon 930, and set date and time selection icon 935 options. In some embodiments, the icons 910, 915, 920, 925, 930, 935 can be arranged as a circle at least partially surrounding a central display 955, where each icon can be selectable to access one or more system features. In some embodiments, the selectable icons 910, 915, 920, 925, 930, 935 can form or define at least a portion of a periphery and/or the circumference of the control wheel 905. In some embodiments, the central display 955 can include a notification or selectable icon for "Main Menu" that can enable users 11 to prompt the system 10 to display a main menu, and also a notification or identification related to the system information menu. In some embodiments, the specification icon 910 can enable a user to access one or more specifications of the dental laser station 25. In some embodiments, the software version icon 920 can enable a user to access a software version of the dental laser station 25. In some embodiments, the memory icon 925 can enable a user to access memory details or information. In some embodiments, application icon 930 can enable a user to access one or more applications of the dental laser station 25. In some embodiments, set date and time selection icon 935 can enable a user to access to set a date or time.

Figure 10:
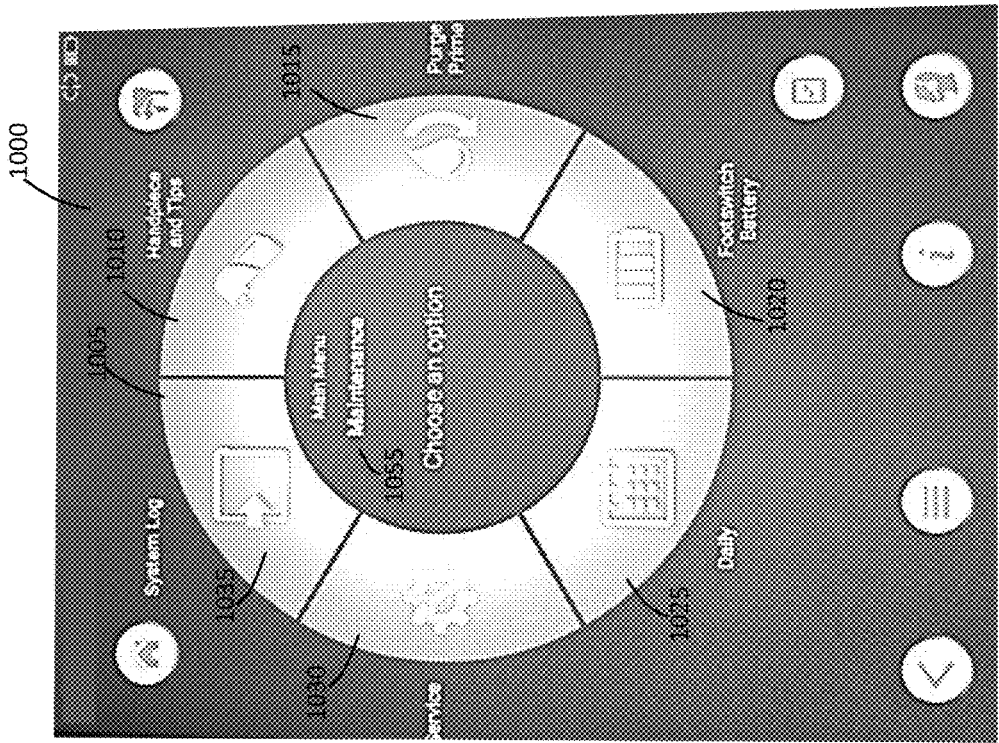
FIG. 10 illustrates a maintenance GUI display in accordance with some embodiments of the invention.

FIG. 10 illustrates a control and information display 1000 shown following access of the maintenance icon 625. In some embodiments, the display 1000 can include a control wheel 1005 including miscellaneous handpiece and tips access icon 1010, purge/prime icon 1015, footswitch battery icon 1020, daily (calendar) icon 1025, service icon 1030, and system log icon 1035. In some embodiments, the icons 1010, 1015, 1020, 1025, 1030, 1035 can be arranged as a circle at least partially surrounding a central display 1055, where each icon can be selectable to access one or more system features. In some embodiments, the selectable icons 1010, 1015, 1020, 1025, 1030, 1035 can form or define at least a portion of a periphery and/or the circumference of the control wheel 1005. In some embodiments, the central display 1055 can include a notification or selectable icon for "Main Menu" that can enable users 11 to prompt the system 10 to display a main menu, and also a notification or identification related to the system information menu. In some embodiments, the handpiece and tips access icon 1010 can enable a user to select or access handpieces and/or tips. In some embodiments, the purge/prime icon 1015 can enable a user to purge or prime the dental laser station 25. In some embodiments, the footswitch battery icon 1020 can enable a user to check a battery function or level of the footswitch battery. In some embodiments, the daily (calendar) icon 1025 can enable a user to access a daily calendar. In some embodiments, the service icon 1030 can enable a user to access a service function. In some further embodiments, the system log icon 1035 can enable a user to access a system log.

Figure 11:
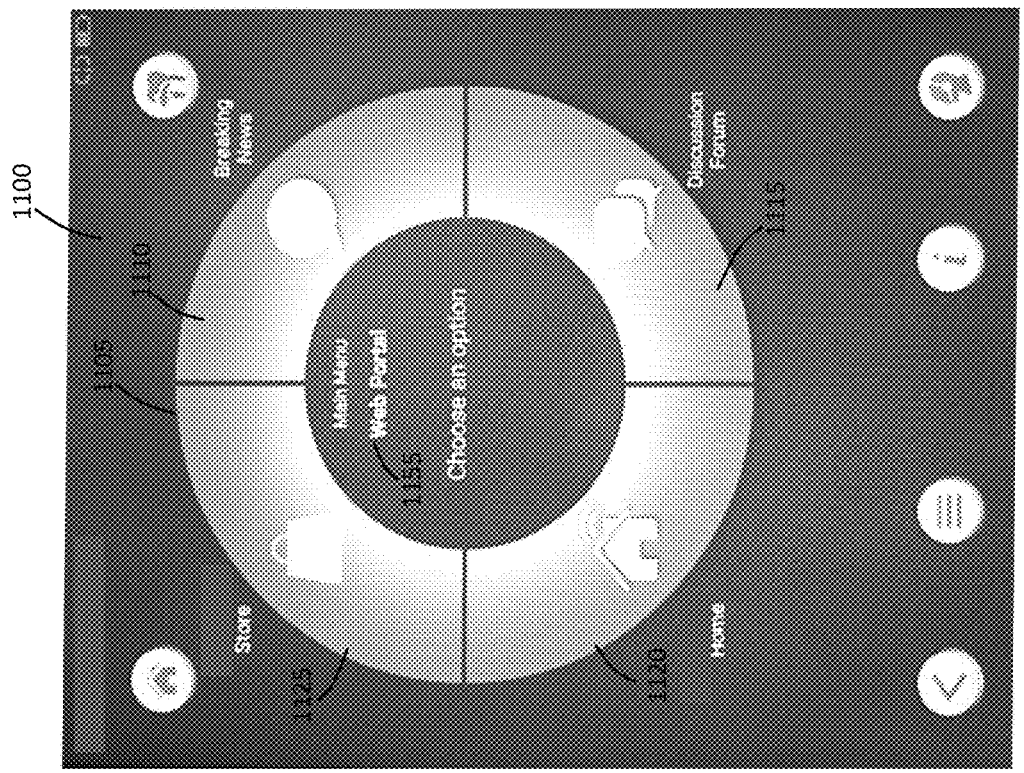
FIG. 11 illustrates a web portal GUI display in accordance with some embodiments of the invention

FIG. 11 illustrates a display 1100 including a control wheel 1105 with control and information following web portal selection using 635 web portal access icon 635. In some embodiments, selectable icons from web portal menus can comprise a breaking news icon 1110, discussion forums icon 1115, home icon 1120, and a store icon 1125. In some embodiments, the icons 1110, 1115, 1120, 1125 can be arranged as a circle at least partially surrounding a central display 1155, where each icon can be selectable to access one or more system features. In some embodiments, the selectable icons 1110, 1115, 1120, 1125 can form or define at least a portion of a periphery and/or the circumference of the control wheel 1105. In some embodiments, the central display 1155 can include a notification or selectable icon for "Main Menu" that can enable users 11 to prompt the system 10 to display a main menu, and also a notification or identification related to the system information menu. In some embodiments, users 11 can utilize the breaking news icon 1110 to access breaking news. In some embodiments, users 11 can utilize the discussion forums icon 1115 to access a forum (e.g., such as a clinical discussion forum). In some embodiments, users 11 can utilize the home icon 1120 to access a home menu. In some embodiments, users 11 can utilize the store icon 1125 to access a store.

Figure 12:
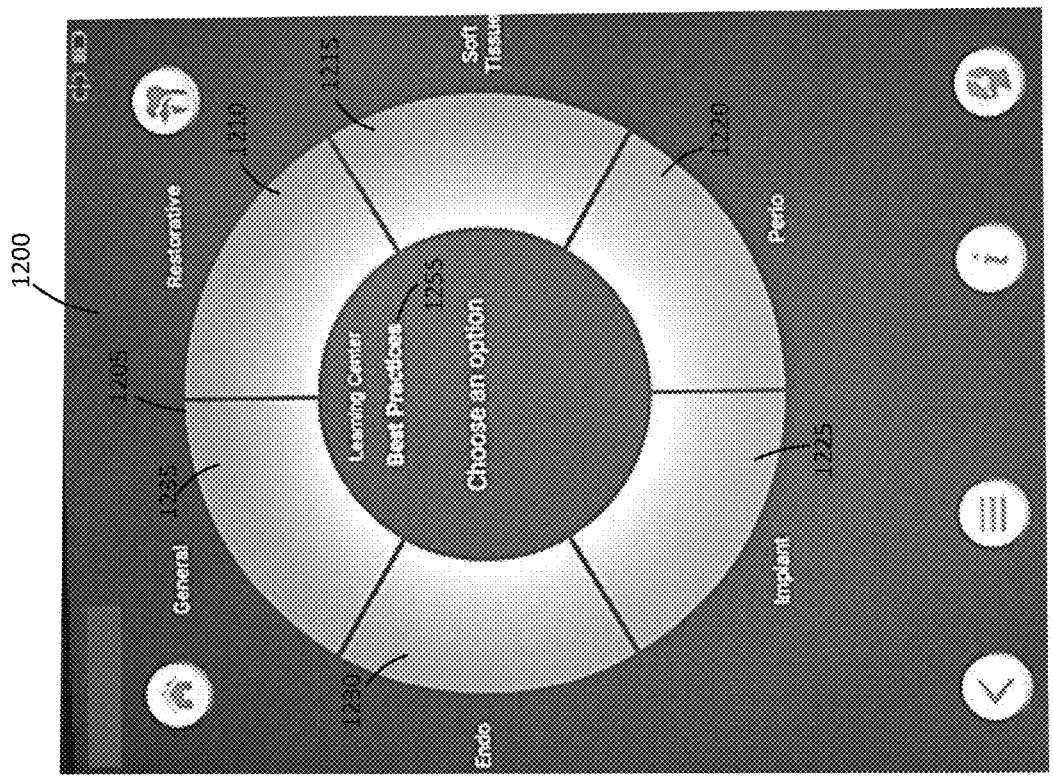
FIG. 12 illustrates a best practices GUI display in accordance with some embodiments of the invention.

FIG. 12 illustrates a control and information display 1200 following selection of the best practices icon 710 (FIG. 7). In some embodiments, the control wheel 1205 can include selectable icons including a restorative category icon 1210, soft tissue category icon 1215, periodontal category icon 1220, implant category icon 1225, endodontic category icon 1230, and a general category icon 1235. In some embodiments, the icons 1210, 1215, 1220, 1225, 1230, and 1235 can be arranged as a circle at least partially surrounding a central display 1255, where each icon can be selectable to access one or more system features. In some embodiments, the selectable icons 1210, 1215, 1220, 1225, 1230, and 1235 can form or define at least a portion of a periphery and/or the circumference of the control wheel 1205. In some embodiments, the central display 1255 can include a notification or selectable icon for "Main Menu" that can enable users 11 to prompt the system 10 to display a main menu, and also a notification or identification related to the system information menu. In some embodiments, users can access procedures, option or steps related to restorative categories using the icon 1210. In some further embodiments, users can access procedures, option or steps related to soft tissue categories using icon 1215. In some embodiments, users can access procedures, option or steps related to periodontal categories using icon 1220. In some embodiments, users can access procedures, option or steps related to implant categories using icon 1225. In some embodiments, users can access procedures, option or steps related to endodontic categories using icon 1230. In some embodiments, users can access procedures, option or steps related to general categories using icon 1235.

Figure 13:
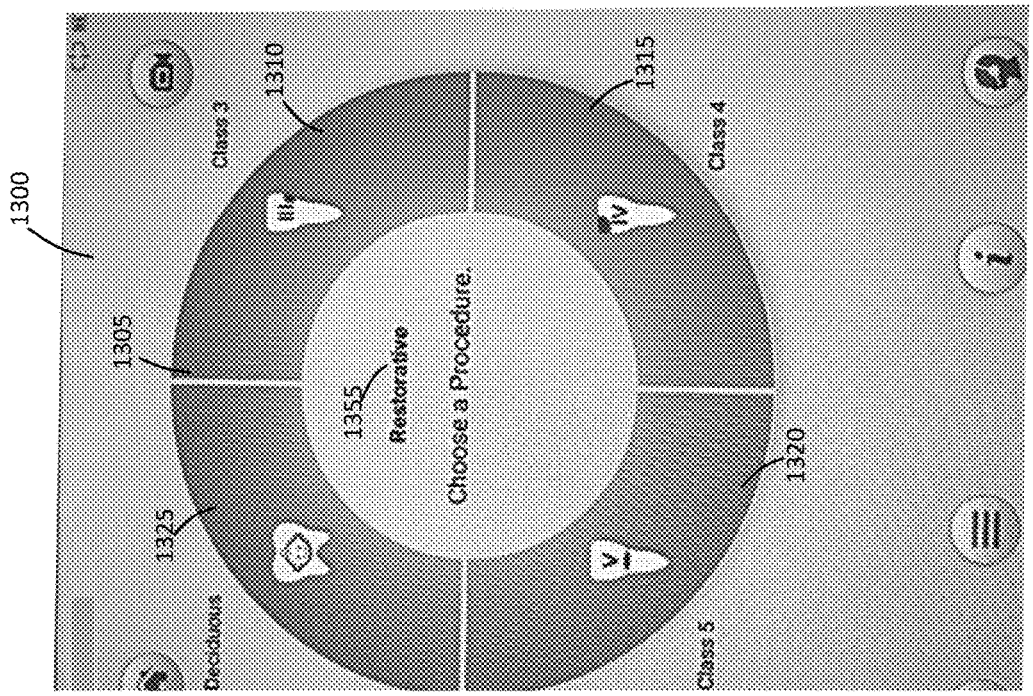
FIG. 13 illustrates a restorative GUI display in accordance with some embodiments of the invention.

FIG. 13 illustrates a display 1300 including a control wheel 1305 with control and information access restorative icons including a class 3 procedure access icon 1310, a class 4 procedure access icon 1315, a class 5 procedure access icon 1320, and deciduous procedure access icon 1325. In some embodiments of the invention, the icons 1310, 1315, 1320, 1325 can be arranged as a circle at least partially surrounding a central display 1355, where each icon can be selectable to access one or more system features. In some embodiments, the selectable icons 1310, 1315, 1320, 1325 can form or define at least a portion of a periphery and/or the circumference of the control wheel 1305. In some embodiments, users can access procedures, option or steps related to restorative categories using a class 3 procedure access icon 1310. In some further embodiments, users can access procedures, option or steps related to restorative categories using a class 4 procedure access icon 1315. In some other embodiments, users can access procedures, option or steps related to restorative categories using a class 5 procedure access icon 1320. In some embodiments, users can access procedures, option or steps related to restorative categories using a deciduous procedure access icon 1325.

Figure 14:
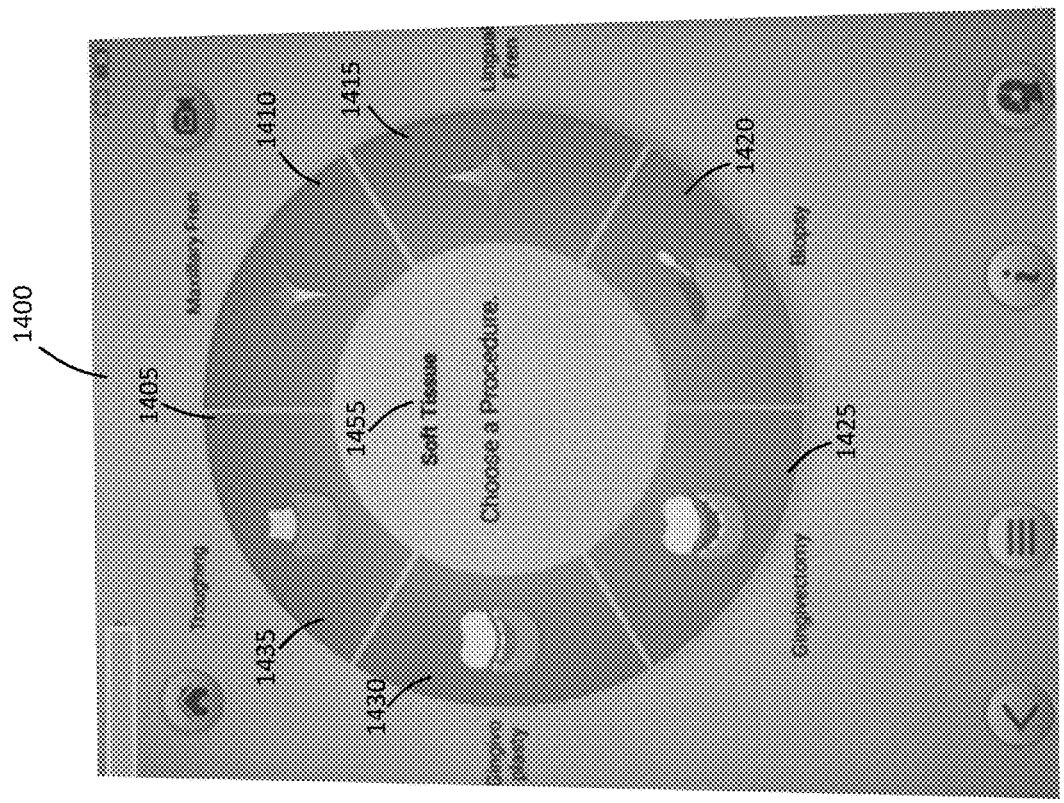
FIG. 14 illustrates a soft tissue GUI display in accordance with some embodiments of the invention.

FIG. 14 illustrates a display 1400 including a control wheel 1405 with illustrates a control and information access soft tissue icons for procedures including maxillary frenum (icon 1410), lingual frenum (icon 1415), biopsy (icon 1420), gingivectomy (icon 1425), gingivoplasty (icon 1430), and troughing (icon 1435). In some embodiments of the invention, the icons 1410, 1415, 1420, 1425, 1430, and 1435 can be arranged as a circle at least partially surrounding a central display 1455, where each icon can be selectable to access one or more system features. In some embodiments, the selectable icons 1410, 1415, 1420, 1425, 1430, and 1435 can form or define at least a portion of a periphery and/or the circumference of the control wheel 1405. In some embodiments, users can access soft tissue related procedures, option or steps related to maxillary frenum using icon 1410. In some further embodiments, users can access soft tissue related procedures, option or steps related to lingual frenum using the icon 1415. In some other embodiments, users can access soft tissue related procedures, option or steps related to biopsy using the icon 1420. In some embodiments, users can access soft tissue related procedures, option or steps related to gingivectomy using the icon 1425. In some further embodiments, users can access soft tissue related procedures, option or steps related to gingivoplasty using the icon 1430. In some embodiments, users can access soft tissue related procedures, option or steps related to troughing using the icon 1435.

Figure 15:
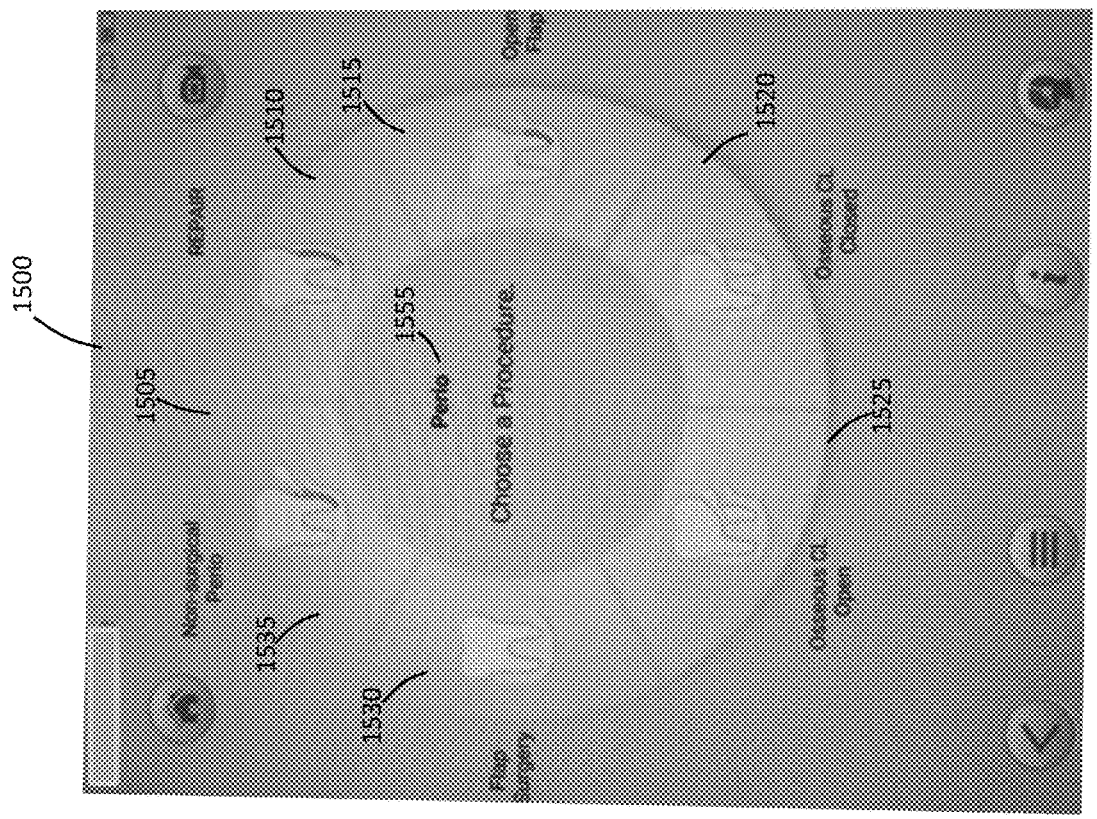
FIG. 15 illustrates a periodontal GUI display in accordance with some embodiments of the invention.

FIG. 15 illustrates a display 1500 including a control wheel 1505 with control and information access icons for periodontal procedures including repair (icon 1510), open flap (1515), osseous CL closed (1520), osseous CL open (1525), flap surgery (1530), and non-surgical periodontics (1535). In some embodiments of the invention, the icons 1510, 1515, 1520, 1525, 1530, and 1535 can be arranged as a circle at least partially surrounding a central display 1555, where each icon can be selectable to access one or more system features. In some embodiments, the selectable icons 1510, 1515, 1520, 1525, 1530, and 1535 can form or define at least a portion of a periphery and/or the circumference of the control wheel 1505. In some embodiments, users can access periodontal related procedures, option or steps related to repair procedures using icon 1510. In some further embodiments, users can access periodontal related procedures, option or steps related to open flap procedures using icon 1515. In some other embodiments, users can access periodontal related procedures, option or steps related to osseous CL closed procedures using icon 1520. In some other embodiments, users can access periodontal related procedures, option or steps related to osseous CL open procedures using icon 1525. In some other embodiments, users can access periodontal related procedures, option or steps related to flap surgery procedures using icon 1530. In some other embodiments, users can access periodontal related procedures, option or steps related to non-surgical periodontics procedures using icon 1535.

Figure 16:
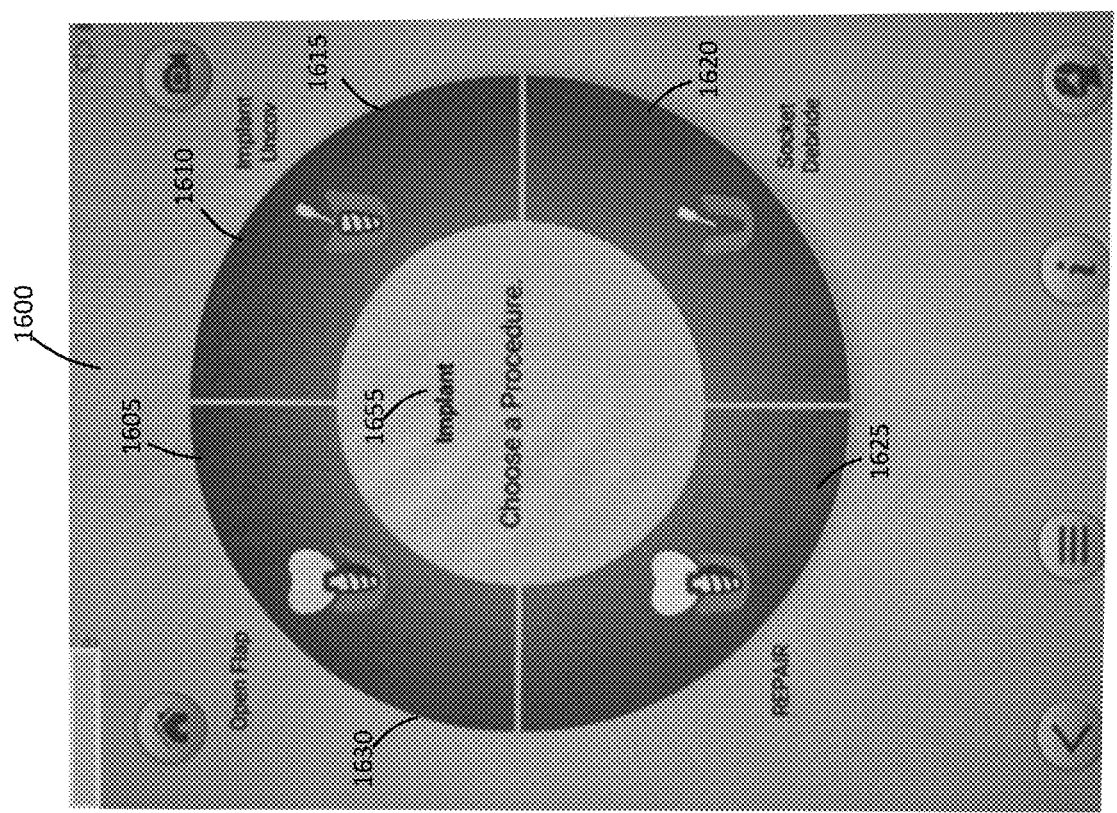
FIG. 16 illustrates an implant GUI display in accordance with some embodiments of the invention.

FIG. 16 illustrates a display 1600 including a control wheel 1605 with control and information access icons for implant procedures including "implant uncov" icon 1610, a socket debride icon 1620, a repair icon 1625, and an open flap icon 1630. In some embodiments of the invention, the icons 1610, 1615, 1620, 1625, and 1630 can be arranged as a circle at least partially surrounding a central display 1655, where each icon can be selectable to access one or more system features. In some embodiments, the selectable icons 1610, 1615, 1620, 1625, and 1630 can form or define at least a portion of a periphery and/or the circumference of the control wheel 1505. In some embodiments, users can access implant related procedures, option or steps related to "implant uncov" procedures using icon 1610. In some embodiments, users can access implant related procedures, option or steps related to socket debride procedures using icon 1620. In some embodiments, users can access implant related procedures, option or steps related to repair icon procedures using 1625. In some embodiments, users can access implant related procedures, option or steps related to open flap procedures using icon 1630.

Figure 17:
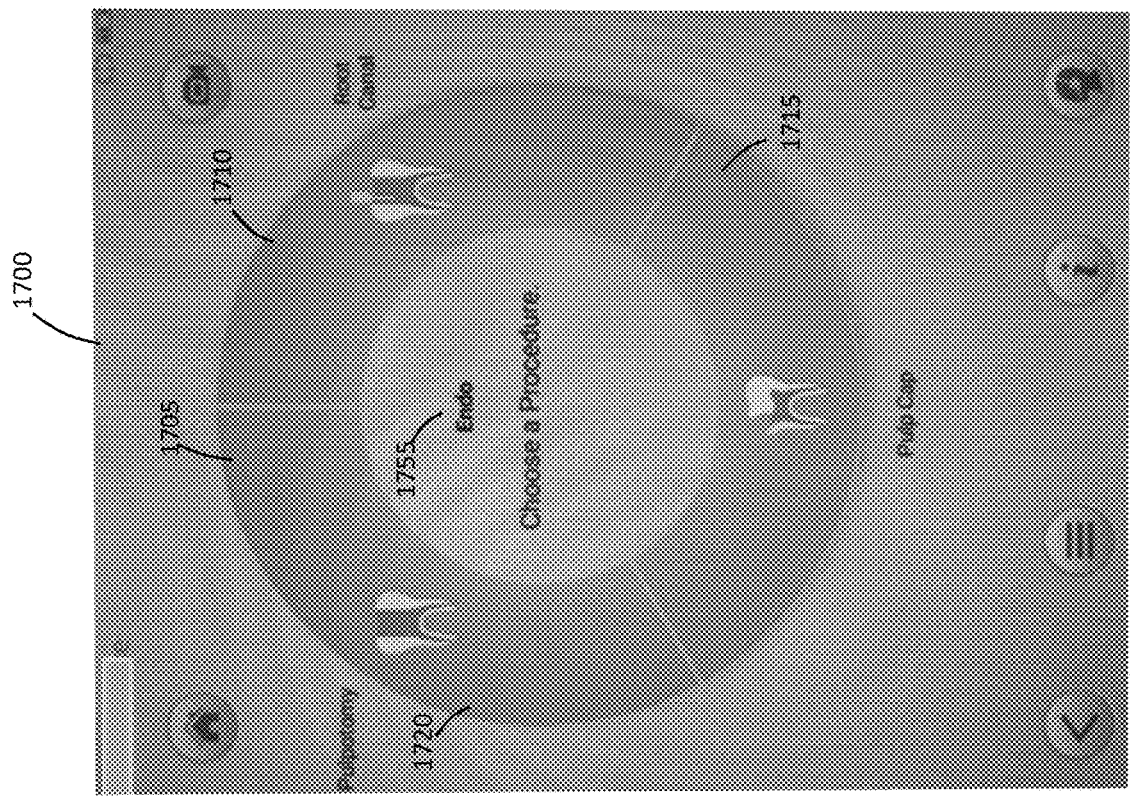
FIG. 17 illustrates an endodontal GUI display in accordance with some embodiments of the invention.

FIG. 17 illustrates a display 1700 including a control wheel 1705 with control and information access icons for endodontic procedures including root canal (icon 1710), pulp cap (1715), and pulpotomy (1720). In some embodiments of the invention, the icons 1710, 1715, and 1720 can be arranged as a circle at least partially surrounding a central display 1755, where each icon can be selectable to access one or more system features. In some embodiments, the selectable icons 1710, 1715, and 1720 can form or define at least a portion of a periphery and/or the circumference of the control wheel 1705. In some embodiments, users can access endodontic procedures, option or steps related to root canal procedures using icon 1710. In some embodiments, users can access endodontic procedures, option or steps related to pulp cap procedures using icon 1715. In some embodiments, users can access endodontic procedures, option or steps related to procedures using a pulpotomy icon 1720.

Figures 18, 19:
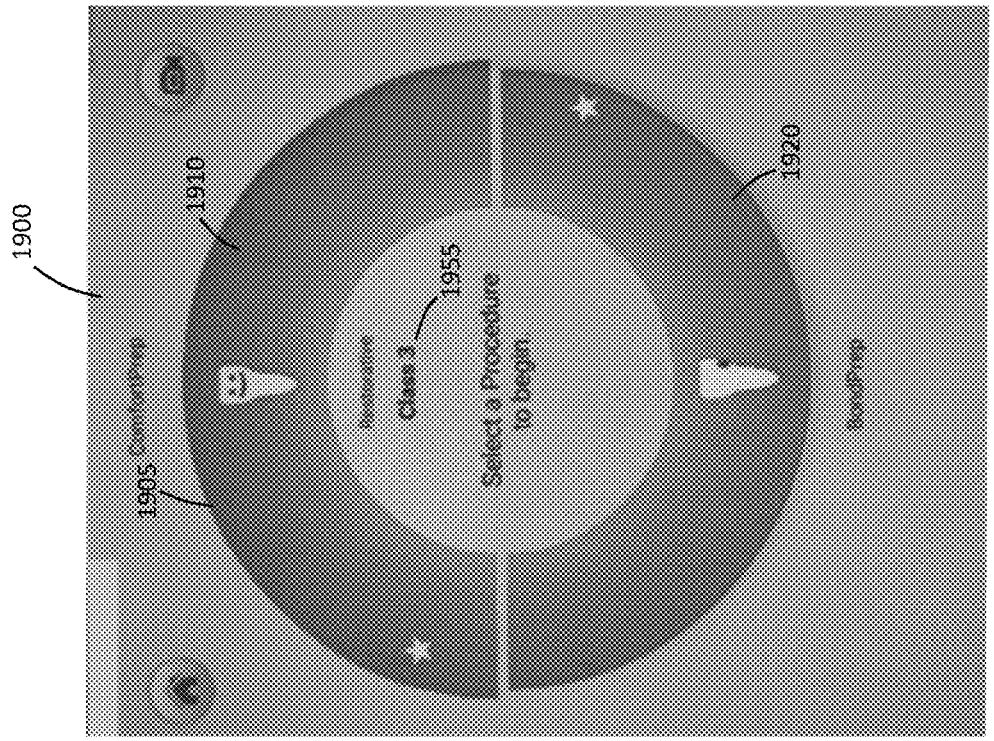
FIG. 18 illustrates a root canal GUI display in accordance with some embodiments of the invention.
FIG. 19 illustrates a Class 3 laser GUI display in accordance with some embodiments of the invention.

FIG. 18 illustrates a display 1800 including a control wheel 1805 with control and information access icons for root canal including clean procedures (icon 1810) and disinfection procedures (1815). In some embodiments of the invention, the icons 1810, 1815 can be arranged as a circle at least partially surrounding a central display 1855, where each icon can be selectable to access one or more system features. In some embodiments, the selectable icons 1810, 1815 can form or define at least a portion of a periphery and/or the circumference of the control wheel 1805. In some embodiments, users can access root canal related procedures, option or steps using icon 1810 for root canal cleaning, and root canal disinfection using icon 1810.

Figure 20:
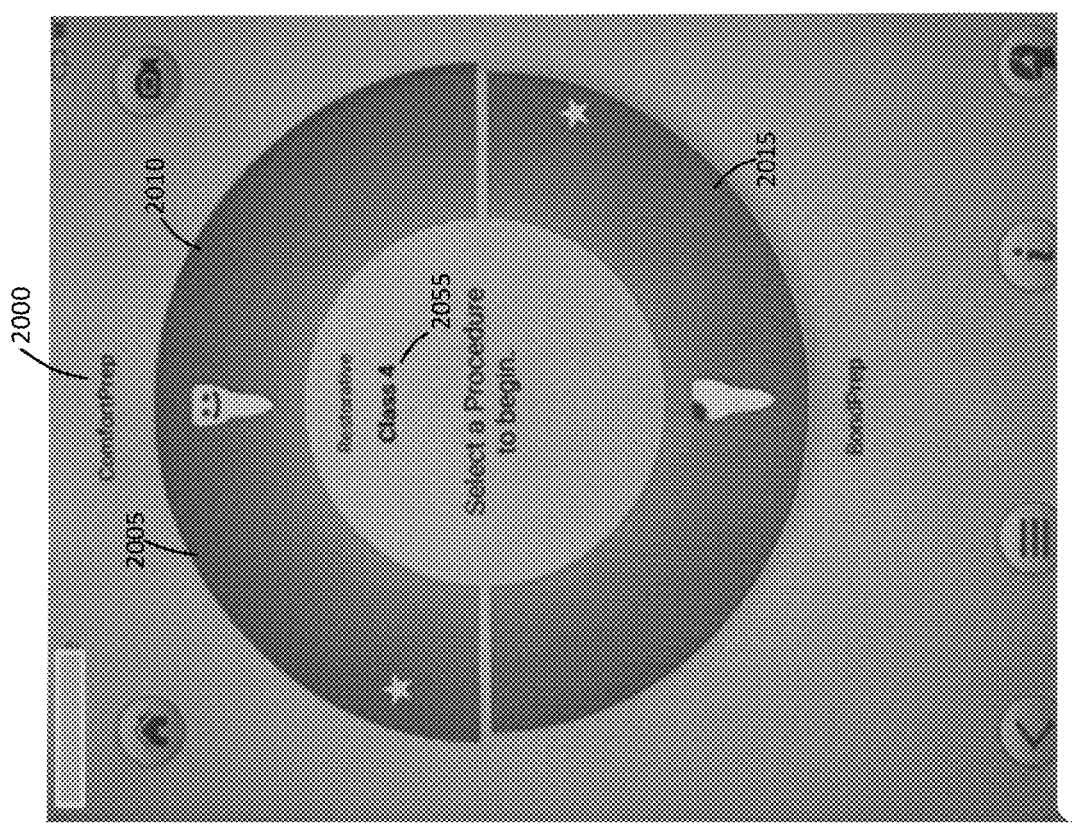
FIG. 20 illustrates a Class 4 laser GUI display in accordance with some embodiments of the invention.

FIG. 19 illustrates a display 1900 including a control wheel 1905 with control and information access icons for class 3 restorative procedures including "comfortprep" (icon 1910), and "BondPrep" (icon 1920). In some embodiments of the invention, the icons 1910, 1915 can be arranged as a circle at least partially surrounding a central display 1955, where each icon can be selectable to access one or more system features. In some embodiments, the selectable icons 1910, 1915 can form or define at least a portion of a periphery and/or the circumference of the control wheel 1905. In some embodiments, users can access class 3 restorative procedures, option or steps using icon 1910 for preparation, and icon 1910 for bonding preparation. Further FIG. 20 illustrates a display 2000 including a control wheel 2005 with control and information access icons for class 4 restorative including "comfortprep" (icon 2010), and "BondPrep" (icon 2015). In some embodiments of the invention, the icons 2010, 2015 can be arranged as a circle at least partially surrounding a central display 2055, where each icon can be selectable to access one or more system features. In some embodiments, the selectable icons 2010, 2015 can form or define at least a portion of a periphery and/or the circumference of the control wheel 2005. In some embodiments, users can access class 4 restorative procedures, option or steps using icon 2010 for preparation, and icon 2010 for bonding preparation.

Figure 21:
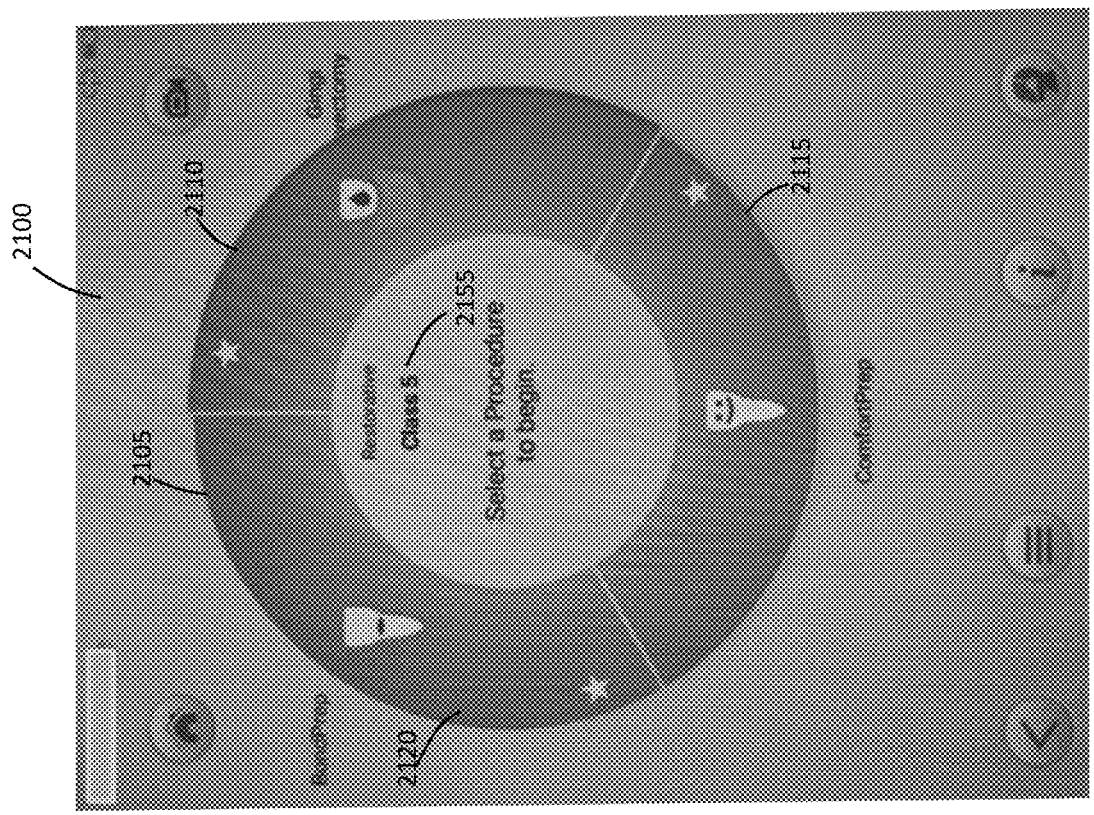
FIG. 21 illustrates a Class 5 laser GUI display in accordance with some embodiments of the invention.

FIG. 21 illustrates a display 2100 including a control wheel 2105 with control and information access icons for class 5 restorative including "Gingivectomy" (icon 2110), "comfortprep" (icon 2115), and "BondPrep" (icon 2120). In some embodiments of the invention, the icons 2110, 2115, 2120 can be arranged as a circle at least partially surrounding a central display 2155, where each icon can be selectable to access one or more system features. In some embodiments, the selectable icons 2110, 2115, and 2120 can form or define at least a portion of a periphery and/or the circumference of the control wheel 2105. In some embodiments, users can access class 5 restorative procedures, option or steps using icon 2110 for gingivectomy procedures. In some embodiments, users can access class 5 restorative procedures, option or steps using icon 2115 for preparation procedures. In some embodiments, users can access class 5 restorative procedures, option or steps using icon 2120 for bonding preparation procedures.

Figure 22:
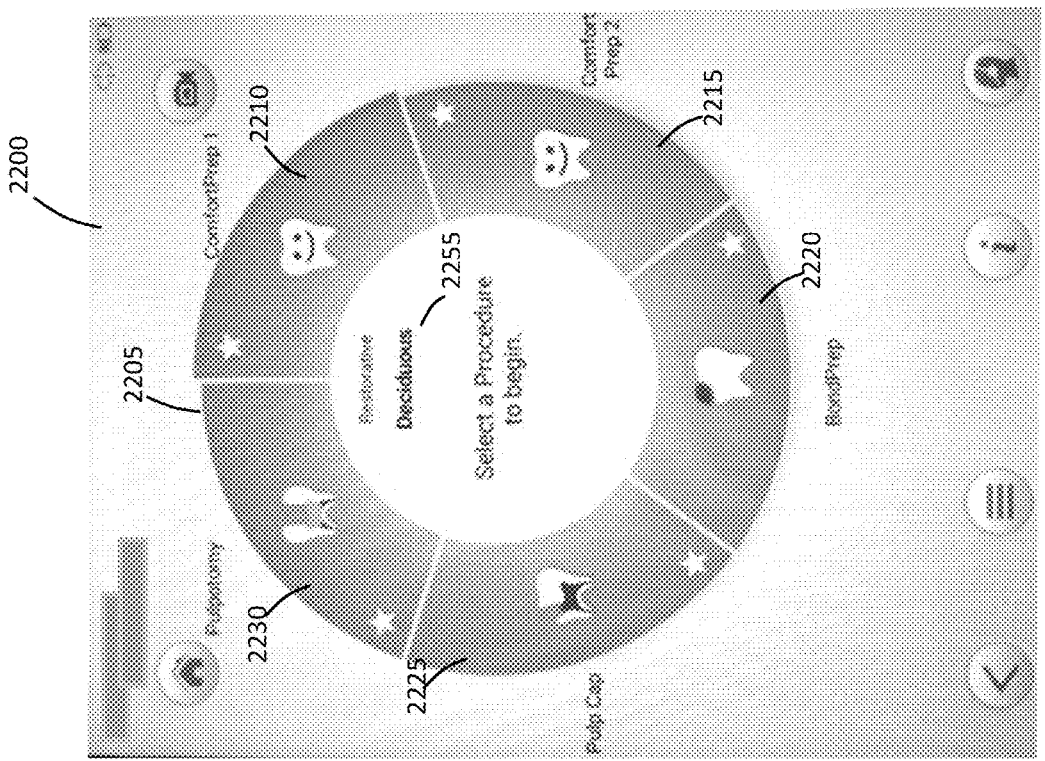
FIG. 22 illustrates a restorative "Deciduous" GUI display in accordance with some embodiments of the invention.

FIG. 22 illustrates a display 2200 including a control wheel 2205 with control and information access icons for restorative deciduous procedures including "ComfortPrep 1" (icon 2210), "ComfortPrep 2" (icon 2215), "BondPrep" (icon 2220), "Pulp Cap" (icon 2225), and "Pulpotomy" (icon 2230). In some embodiments of the invention, the icons 2210, 2215, 2220, 2225, and 2230 can be arranged as a circle at least partially surrounding a central display 2255, where each icon can be selectable to access one or more system features. In some embodiments, the selectable icons 2210, 2215, 2220, 2225, and 2230 can form or define at least a portion of a periphery and/or the circumference of the control wheel 2205. In some embodiments, users can access restorative deciduous procedures, option or steps for procedures including preparation using icon 2210, 2215. In some embodiments, users can access restorative deciduous procedures, option or steps for procedures including bond preparation using icon 2220. In some embodiments, users can access restorative deciduous procedures, option or steps for procedures including pulp cap preparation using icon 2225. In some embodiments, users can access restorative deciduous procedures, option or steps for procedures including pulpotomy" using icon 2230.

Figure 23:
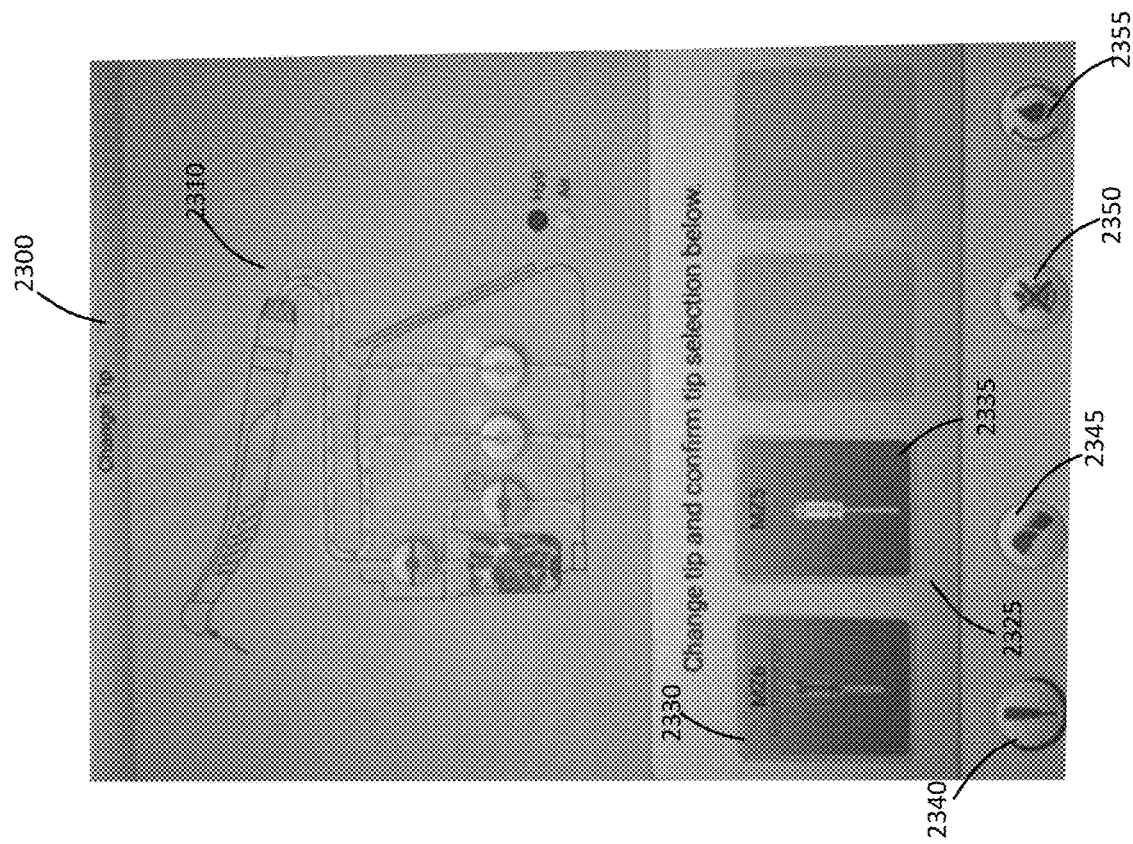
FIG. 23 illustrates a change tip display in accordance with some embodiments of the invention.

In some embodiments of the invention, the system 10 can render an operation and/or system display to assist users 11 with reviewing and/or selecting operations and parameters. For example, FIG. 23 illustrates a control and information of display 2300 of the dental laser station 25 of FIG. 1B in accordance with some embodiments of the invention. In this non-limiting embodiment, operation of the system including flow of water and/or air and two selections tip icons is shown as a fixed image or as an animation in the display 2300. For example, in some embodiments, following a selection of a procedure, the display 2300 can render an animation of the operation of the system 10 including flow of water and/or air with a display 2300. Further, in some embodiments, the display 2300 can show one or more icons for selection 2325 of specific tips (e.g., such as tip icon 2330 and/or tip icon 2335). Related icons 2340, 2345 can be used to select and/or initiate tip changeover procedures. Further, air and/or water flow can be controlled using icons 2350, 2355.

Figure 24:
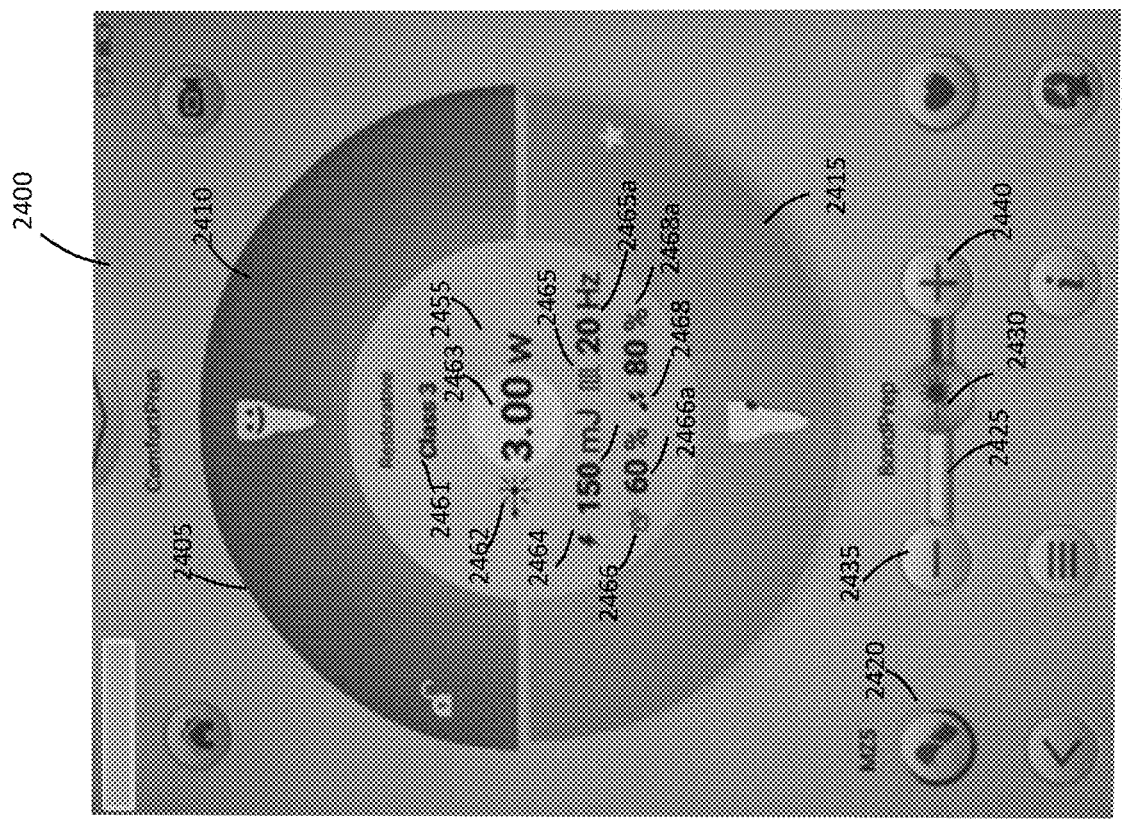
FIG. 24 illustrates a restorative Class 3 control GUI display in accordance with some embodiments of the invention.

FIG. 24 illustrates a display 2400 including a control wheel 2405 with control and information display of the dental laser station 25 of FIG. 1B in accordance with some embodiments of the invention. In some embodiments of the invention, the icons 2410, 2415 can be arranged as a circle at least partially surrounding a central display 2455, where each icon can be selectable to access one or more system features. In some embodiments, the selectable icons 2410, 2415 can form or define at least a portion of a periphery and/or the circumference of the control wheel 2405. In some embodiments, users can access restorative procedures, option or steps for Class 3 procedures including preparation using icon 2410, and bonding preparation using icon 2415. In some embodiments, the display 2400 can include operating parameters and a selectable slider 2430 on a bar 2425 for modifying and/or setting at least one parameter of at least one procedure dental laser station 25. In some embodiments, the slider 2430 can be moved by the users 11 interaction of the display 250 to control one or more parameters of the dental laser station 25. In some embodiments, the slider 2430 can be moved towards a negative end 2435 to reduce laser power and towards the positive end 2440 to increase the laser power. Further, in some embodiments, the central display 2455 can include a display of one or more parameters of the dental laser station 25. For example, in some embodiments, the central display 2455 can include a display of laser power, and/or laser energy, and/or pulse rate, and/or water flow, and/or air flow. Some embodiments include a displayed procedure name 2461. Further, some embodiments include a laser status icon 2462 illustrative of a status of one or more laser sources of the dental laser station 25. Some embodiments also include a power level display 2463 illustrative of the current power level of the one or more laser sources of the dental laser station 25. Some further embodiments include an energy level icon 2464 that in some embodiments includes an adjacent energy level display 2464a showing a display of the energy level. Some further embodiments include an air level icon 2466 that in some embodiments includes an adjacent air level display 2466a showing a display of the air flow level. Some further embodiments include a water level icon 2468 that in some embodiments includes an adjacent water level display 2468a showing a display of the water flow level. Some further embodiments include a frequency level icon 2465 that in some embodiments includes an adjacent frequency level display 2465a showing a display of the frequency level.

In some further embodiments, users 11 can use the display 2400 (or other non-limiting examples described herein) to change or modify one or more parameters related to the operation and function of a dental laser, including, but not limited to, laser pulse peak power, laser pulse repetition rate, laser pulse duration, laser average output power, and volume and quality of the cooling water spray or air flow using a master controller. For example, in some embodiments, using the master controller, any of the parameters that would normally be controlled by the one or more of the sliders of the display 2400. In some embodiments, parameters of a dental laser station (e.g., such as dental laser station 25) can be controlled using the master controller, and any change in values can accordingly be reflected in the display 2400 (e.g., such as within the central display 2455).

Figure 25:
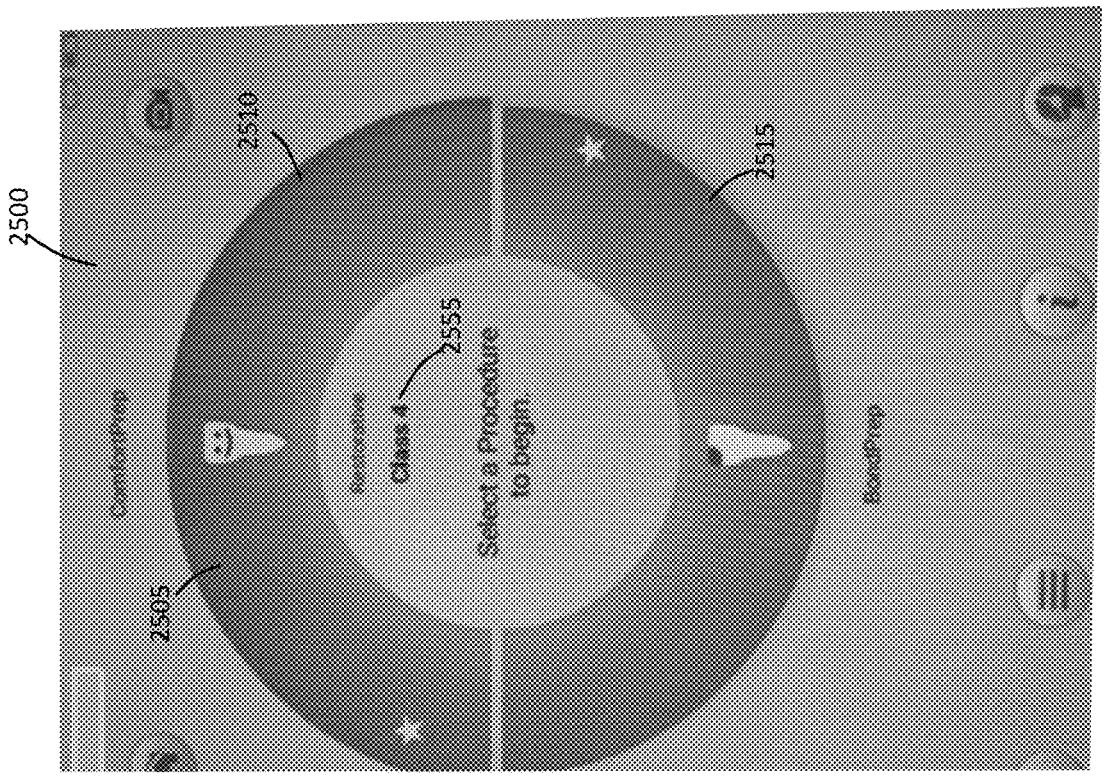
FIG. 25 illustrates a Class 4 GUI display in accordance with some embodiments of the invention.
Figure 26:
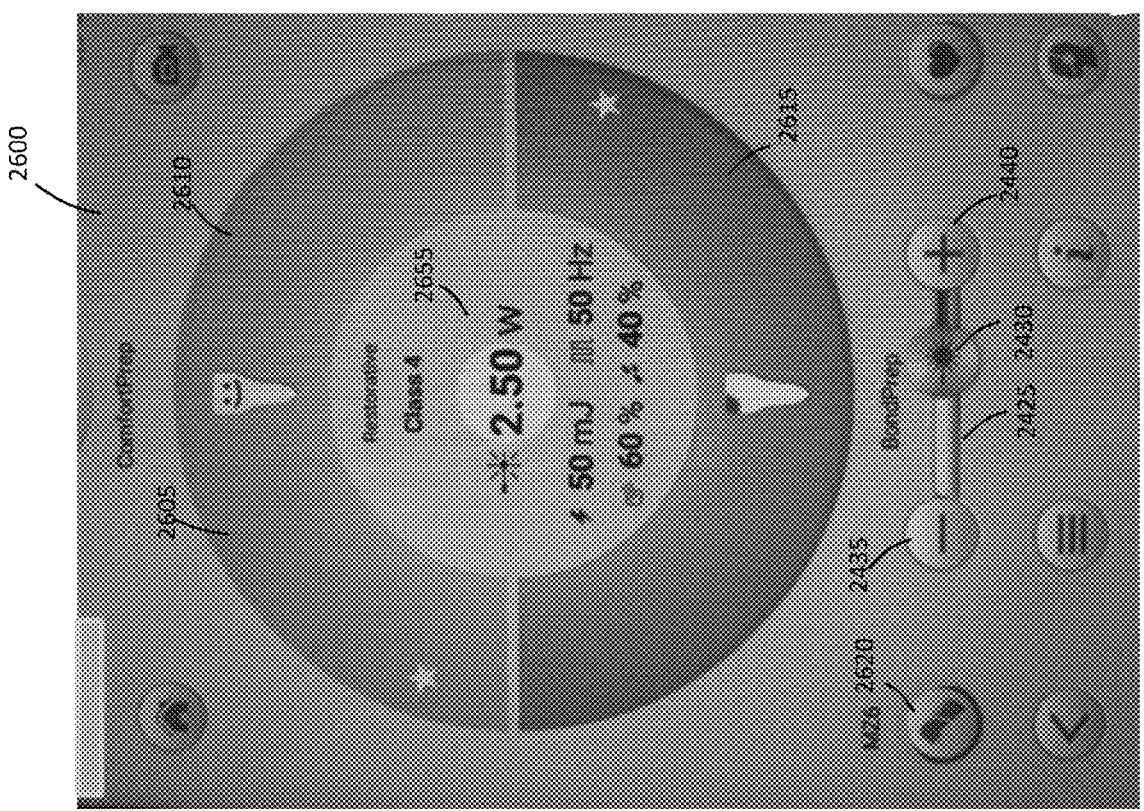
FIG. 26 illustrates a restorative Class 4 control GUI display in accordance with some embodiments of the invention.

FIG. 25 illustrates a display 2500 including a control wheel 2505 with control and information display of the dental laser station 25 of FIG. 1B in accordance with some embodiments of the invention, where selection of a restorative procedure icon (e.g., such as restorative "Comfort-Prep" icon 2510 or "BondPrep" icon 2515) can enable the display of FIG. 26, illustrating a display 2600 including a control wheel 2605 with control and information display of the dental laser station of FIG. 1B in accordance with some embodiments of the invention. In some embodiments, the display 2600 can include operating parameters and a selectable slider for modifying and/or setting at least one parameter of the procedure. Referring to FIG. 25, in some embodiments of the invention, the icons 2510, 2515 can be arranged as a circle at least partially surrounding a central display 2555, where each icon can be selectable to access one or more system features. In some embodiments, the selectable icons 2510, 2515 can form or define at least a portion of a periphery and/or the circumference of the control wheel 2505. In some embodiments, users can access restorative procedures, option or steps for Class 4 procedures including preparation using icon 2510, and bonding preparation using icon 2515. In some embodiments, the display 2500 can include operating parameters and a selectable slider 2430 on a bar 2425 as described earlier. In some embodiments, the central display 2555 can include a display of one or more parameters of the dental laser station 25. For example, in some embodiments, the central display 2555 can include a display of laser power, and/or laser energy, and/or pulse rate, and/or water flow, and/or air flow. Referring to FIG. 26, in some embodiments of the invention, the icons 2610, 2615 can be arranged as a circle at least partially surrounding a central display 2655, where each icon can be selectable to access one or more system features. In some embodiments, the selectable icons 2610, 2615 can form or define at least a portion of a periphery and/or the circumference of the control wheel 2605. In some embodiments, users can access restorative procedures, option or steps for Class 4 procedures including preparation using icon 2610, and bonding preparation using icon 2615. In some embodiments, the display 2600 can include operating parameters and a selectable slider 2430 on a bar 2425 as described earlier. In some embodiments, the central display 2655 can include a display of one or more parameters of the dental laser station 25. For example, in some embodiments, the central display 2655 can include a display of laser power, and/or laser energy, and/or pulse rate, and/or water flow, and/or air flow.

Figure 27:
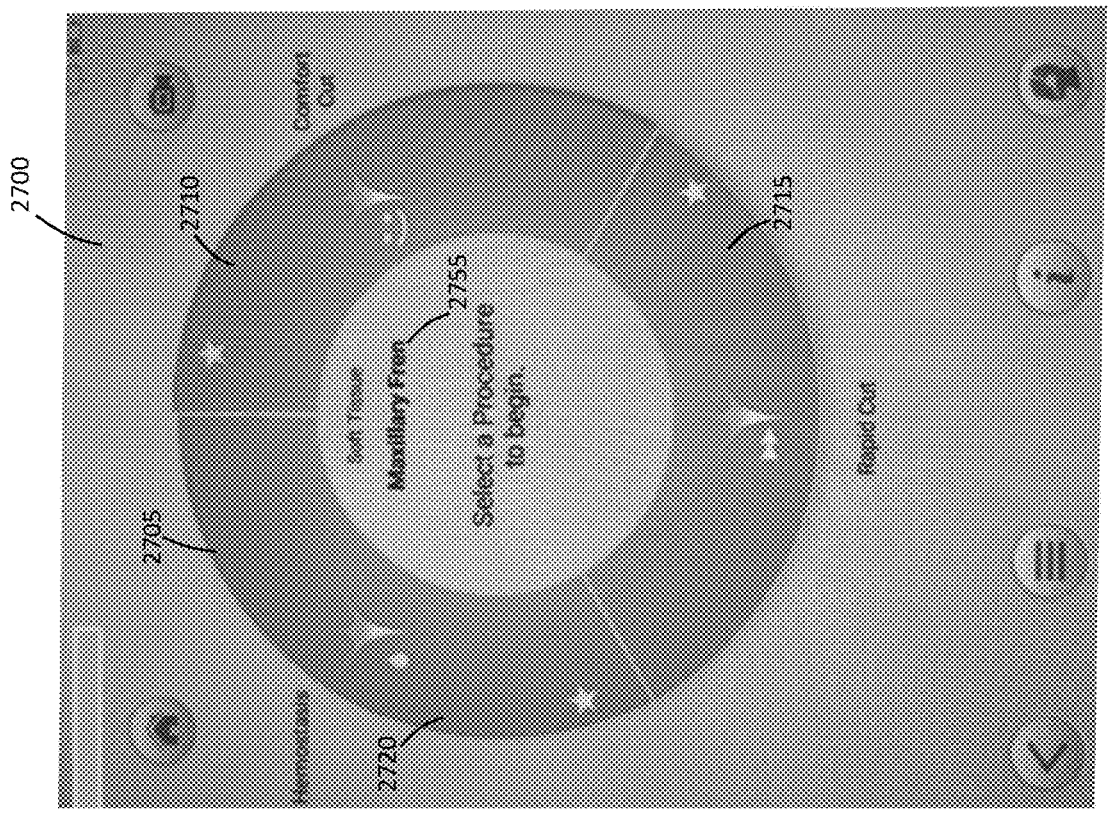
FIG. 27 illustrates a soft tissue "Maxillary Fren" GUI display in accordance with some embodiments of the invention.
Figure 28:
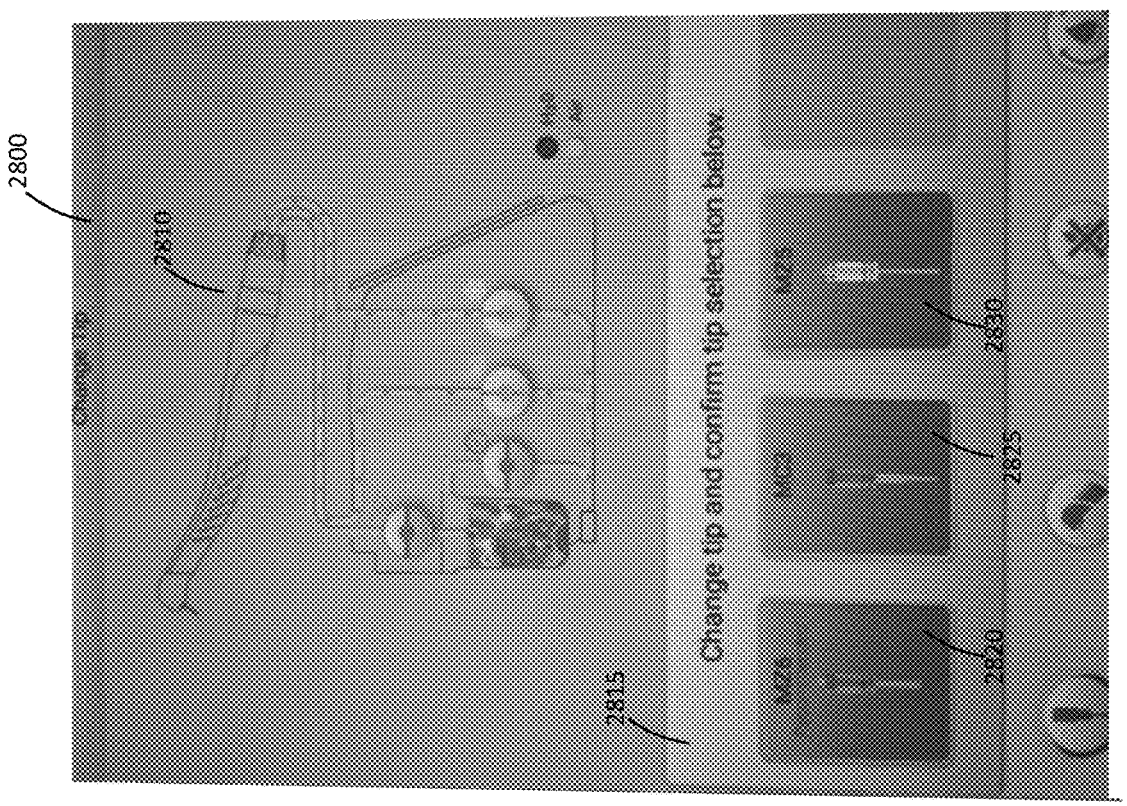
FIG. 28 illustrates a tip selection GUI display in accordance with some embodiments of the invention.

FIG. 27 illustrates a display 2700 including a control wheel 2705 with control and information display of the dental laser station 25 of FIG. 1B in accordance with some embodiments of the invention. In some embodiments, selection of any of the soft tissue maxillary fren procedures (e.g., such as "Comfort Cut" (icon 2710), "Rapid Cut" (icon 2715), or "Hemostasis" (icon 2720) can enable the rendering of the display of FIG. 28 illustrates a display 2800 including a representation of the operation of the system 10 including flow of water and/or air and selections of tips of the dental laser station 25 of FIG. 1B in accordance with some embodiments of the invention. In some embodiments, the display can render an animation of the operation of the system including flow of water and/or air. Further, in some embodiments, the display can show one or more icons for selection of specific tips to the procedure. Referring to FIG. 27, in some embodiments of the invention, the icons 2710, 2715, 2720 can be arranged as a circle at least partially surrounding a central display 2755, where each icon can be selectable to access one or more system features. In some embodiments, the selectable icons 2710, 2715, 2720 can form or define at least a portion of a periphery and/or the circumference of the control wheel 2705. In some embodiments, users can access soft tissue maxillary fren procedures, option or steps for Class 4 including preparation using a cutting procedure "Comfort Cut" (icon 2710), "Rapid Cut" (icon 2715), or a hemostatis procedure "Hemostasis" (icon 2720). Referring to FIG. 28, in this non-limiting embodiment, operation of the system 10 including flow of water and/or air and two selections tip icons is shown as a fixed image or as an animation is represented in the display 2800. For example, in some embodiments, following a selection of a procedure from the display 2700 of FIG. 27, the display 2800 can render an animation of the operation of the system 10 including flow of water and/or air with a display 2800. Further, in some embodiments, the display 2800 can show one or more icons for selection 2815 of specific tips (e.g., such as tip icon 2820 and/or tip icon 2825, and/or tip icon 2830).

Figure 29:
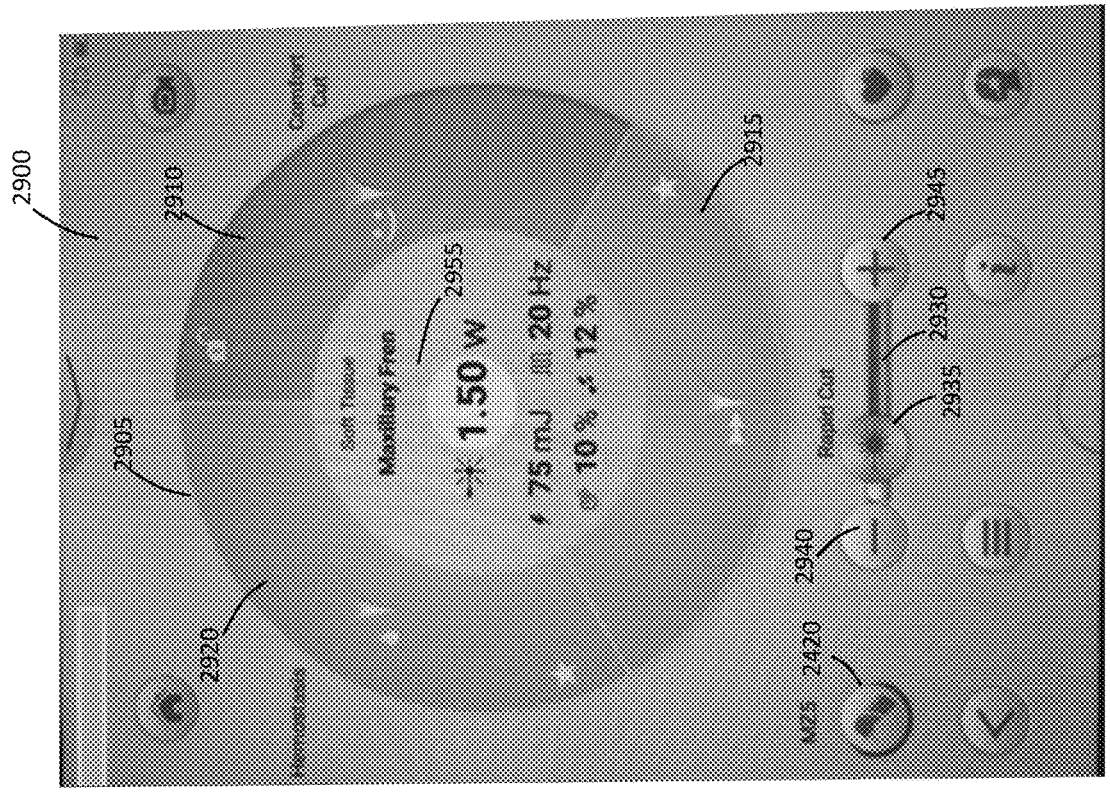
FIG. 29 illustrates a soft tissue "Maxillary Fren" control GUI display in accordance with some embodiments of the invention.
Figure 30:
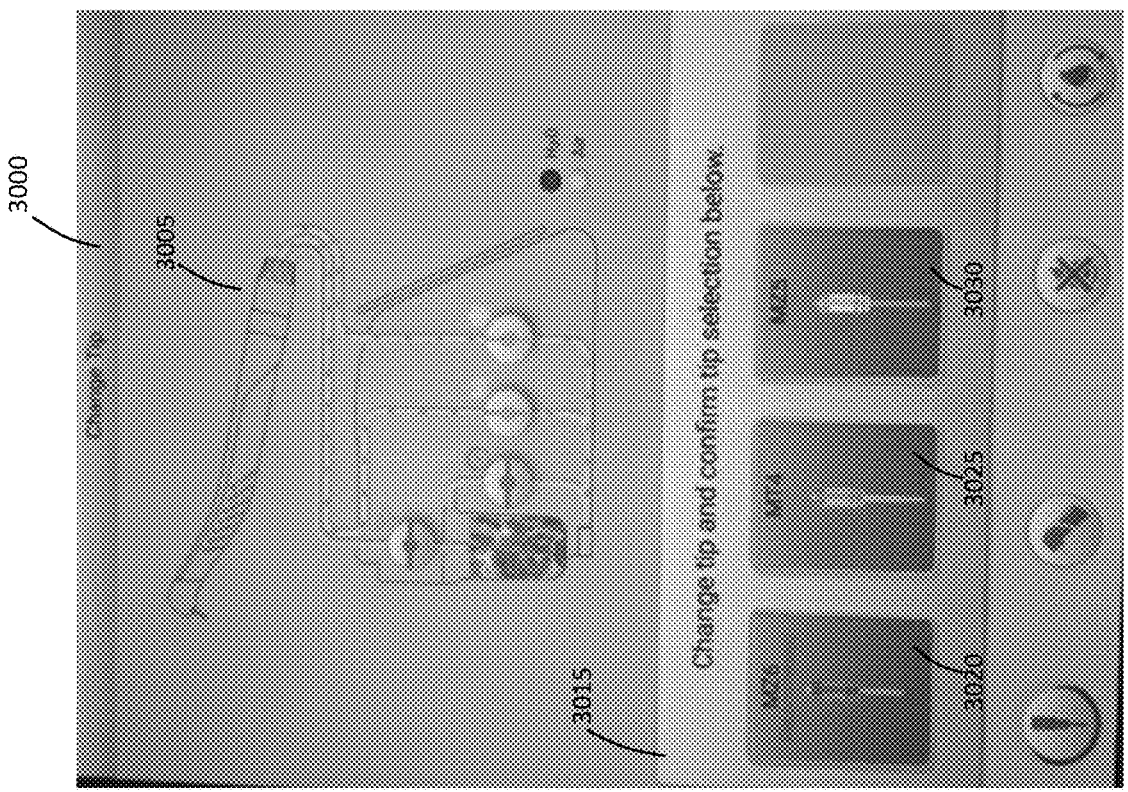
FIG. 30 illustrates a tip change and confirm GUI display in accordance with some embodiments of the invention.

Another non-limiting example embodiment is shown in FIG. 29, illustrating a display 2900 including a control wheel 2905 with control and information display of the dental laser station 25 of FIG. 1B in accordance with some embodiments of the invention. In some embodiments, the display 2900 can include operating parameters and a selectable slider 2935 for modifying and/or setting at least one parameter of the procedure, where the display 2900 can include selection of "Comfort Cut" (icon 2910), "Rapid Cut" (icon 2915), and "Hemostasis" (icon 2920), the selection of which can enable the display of animation of the operation of the system including flow of water and/or air, and one or more icons for selection of specific tips to the procedure. See for example, FIG. 30 illustrating a display 3000 including a representation of the operation of the system 10 including flow of water and/or air and selections of tips of the dental laser station 25 of FIG. 1B in accordance with some embodiments of the invention. Referring to FIG. 29, in some embodiments of the invention, the icons 2910, 2915, 2920 can be arranged as a circle at least partially surrounding a central display 2955, where each icon can be selectable to access one or more system features. In some embodiments, the selectable icons 2910, 2915, 2920 can form or define at least a portion of a periphery and/or the circumference of the control wheel 2905. In some embodiments, users can access soft tissue, maxillary fren procedures, option or steps including preparation using icon 2610, 2615 for cutting, and icon 2920 for hemostatis. In some embodiments, the display 2900 can include operating parameters and a selectable slider 2935 on a bar 2930 as described earlier. In some embodiments, the central display 2955 can include a display of one or more parameters of the dental laser station 25. For example, in some embodiments, the central display 2955 can include a display of laser power, and/or laser energy, and/or pulse rate, and/or water flow, and/or air flow. In some embodiments, tip icon 2420 can be accessed to access or select one or more tips. Referring to FIG. 30, in this non-limiting embodiment, operation of the system 10 including flow of water and/or air and three selection tip icons is shown as a fixed image or as an animation is represented in the display 3000. For example, in some embodiments, following a selection of a procedure from the display 2900 of FIG. 29, the display 3000 can render an animation of the operation of the system 10 including flow of water and/or air with a display 3000. Further, in some embodiments, the display 3000 can show one or more icons for selection 3015 of specific tips (e.g., such as tip icon 3020 and/or tip icon 3025, and/or tip icon 3030).

Figure 31:
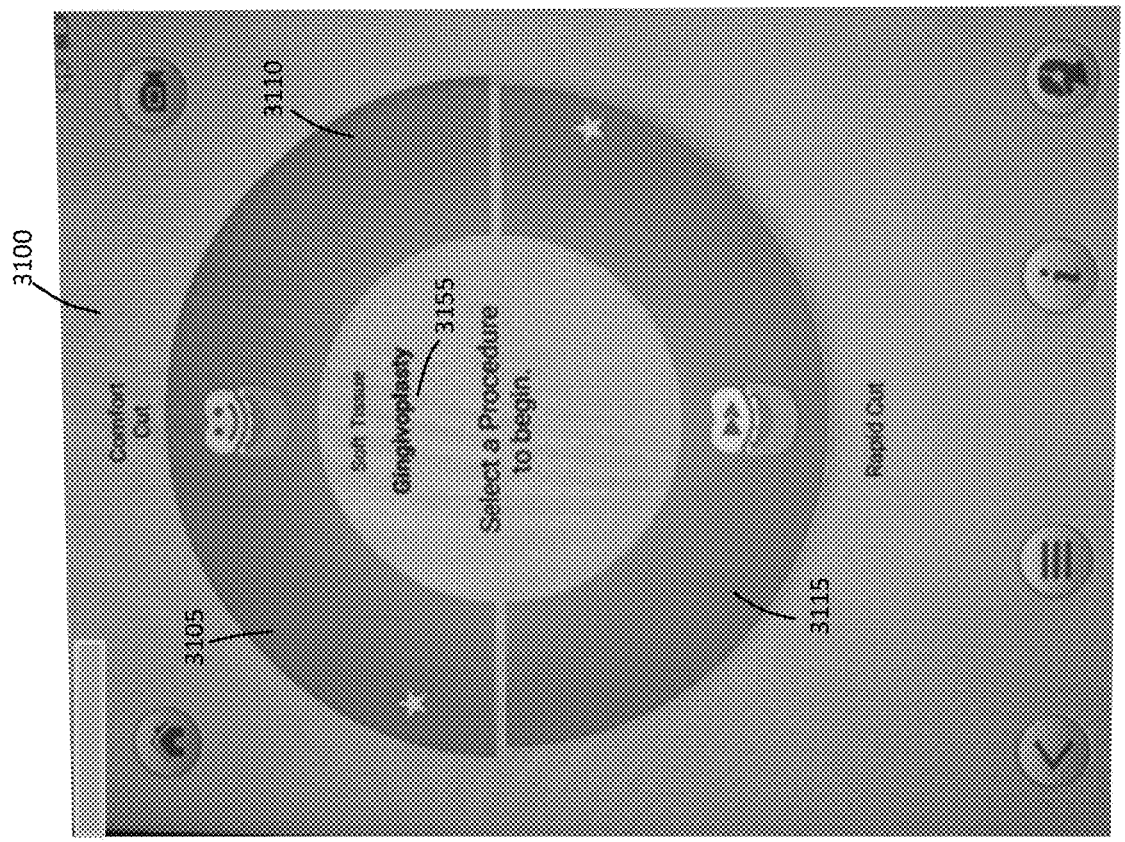
FIG. 31 illustrates a soft tissue "Gingivoplasty" GUI display in accordance with some embodiments of the invention.

A further non-limiting example embodiment is shown in FIG. 31, illustrating a display 3100 including a control wheel 3105 with control and information display of the dental laser station 25 of FIG. 1B in accordance with some embodiments of the invention. In some embodiments, the display 3100 can include operating parameters with selectable icons modifying and/or setting at least one parameter of the procedure, where the display 3100 can include selection of "Comfort Cut" (icon 3110), "Rapid Cut" (icon 3115), where the selection of which can enable the display of animation of the operation of the system including flow of water and/or air, and one or more icons for selection of specific tips to the procedure. See for example, FIG. 32 illustrating a display 3200 including a representation of the operation of the system 10 including flow of water and/or air and selections of tips of the dental laser station 25 of FIG. 1B in accordance with some embodiments of the invention. Referring to FIG. 31, in some embodiments of the invention, the icons 3110, 3115 can be arranged as a circle at least partially surrounding a central display 3155, where each icon can be selectable to access one or more system features. In some embodiments, the selectable icons 3110, 3115 can form or define at least a portion of a periphery and/or the circumference of the control wheel 3105. In some embodiments, users can access soft tissue, gingivoplasty procedures, option or steps including preparation using icons 3110, 3115 for cutting. Referring to FIG. 32, in this non-limiting embodiment, operation of the system 10 including flow of water and/or air and three selection tip icons is shown as a fixed image or as an animation is represented in the display 3200. For example, in some embodiments, following a selection of a procedure from the display 3100 of FIG. 31, the display 3200 can render an animation of the operation of the system 10 including flow of water and/or air. Further, in some embodiments, the display 3200 can show one or more icons for selection 3210 of specific tips (e.g., such as tip icon 3215 and/or tip icon 3220, and/or tip icon 3225).

Figure 35:
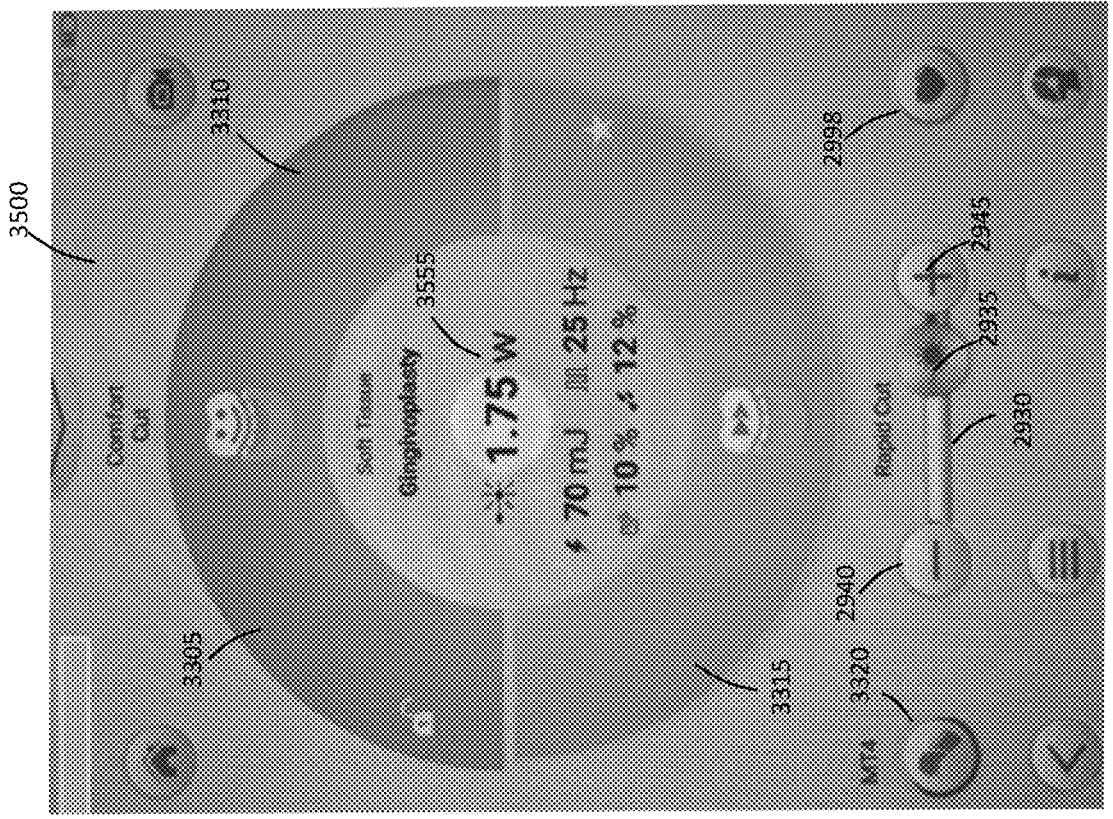
Figure 34:
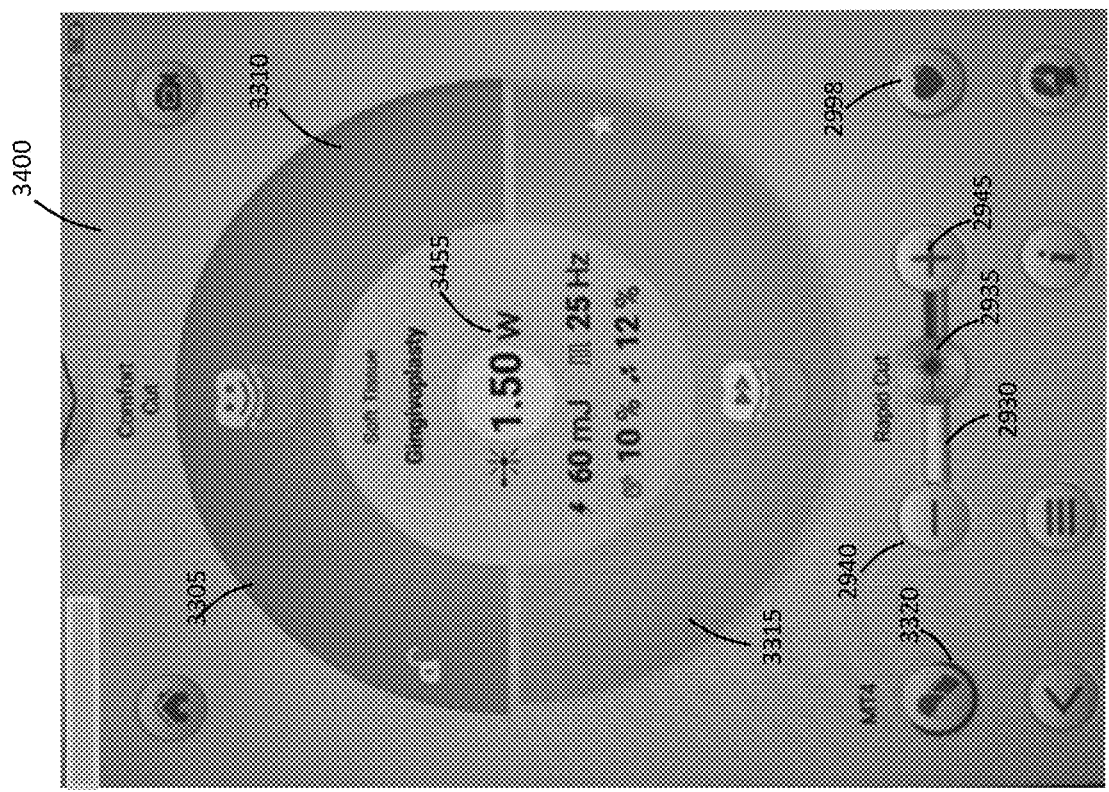

FIGS. 33-35 illustrate soft tissue "Gingivoplasty" control GUI displays in accordance with some embodiments of the invention. In reference to FIG. 33 illustrating a display 3300 according to some embodiments, a control wheel 3305 can comprise a control and information display of the dental laser station 25 of FIG. 1B. In some embodiments, selection of any of the gingivoplasty procedures such as "Comfort Cut" (icon 3310) or "Rapid Cut" (icon 3315), or "Hemostasis" (icon 2720) can enable the procedures that can be controlled using the slider 2935. In some embodiments, icons 3310, 3315 can be arranged as a circle at least partially surrounding a central display 3355, where each icon can be selectable to access one or more system features. Further, in some embodiments, the central display 3355 can include a display of one or more parameters of the dental laser station 25. For example, in some embodiments, the central display 3355 can include a display of laser power, and/or laser energy, and/or pulse rate, and/or water flow, and/or air flow. In some embodiments, the selectable icons 3310, 3315 can form or define at least a portion of a periphery and/or the circumference of the control wheel 3305. In some embodiments, users can access the slider 2935 and move the slider 2935 along the bar 2930 towards a positive end 2945 to increase laser power, or towards a negative end 2940 to decrease the laser power. By controlling the laser using the slider 2935, users 11 can control the cutting speed and/or depth of cutting.

According to some embodiments of the invention, when a user (e.g., such as users 11) moves the slider 2935 along the bar 2930 towards the positive end 2945, the central display 3355 can be updated to the central display 3455 shown in the display 3400 of FIG. 34. Further, in reference to FIG. 35, when a user moves the slider 2935 along the bar 2930 towards the positive end 2945, the central display 3355 can be updated to the central display 3555 shown in the display 3500 of FIG. 35.

As described earlier with respect to at least FIG. 5, some embodiments include access to selection of favorite procedures, options and/or steps. As shown in FIGS. 33-35, some embodiments include a favorite icon 2998. In some embodiments, access by users 11 to favorites can be accomplished using the favorite icon 2998, resulting in a display 3600 of FIG. 36, illustrates a control and information display of the dental laser station of FIG. 1B including an overlap menu 3610 for selection from a pool of favorite procedures. In some embodiments, users 11 can access one or more of the favorites of the menu 3610 and/or store/save one or more parameter settings as a favorite.

Figure 37:
FIG. 37 shows a display of system settings and parameters for procedures, options, and steps for restorative categories and Class 1-2, and Class 3 procedures in accordance with some embodiments of the invention.
Figure 42:
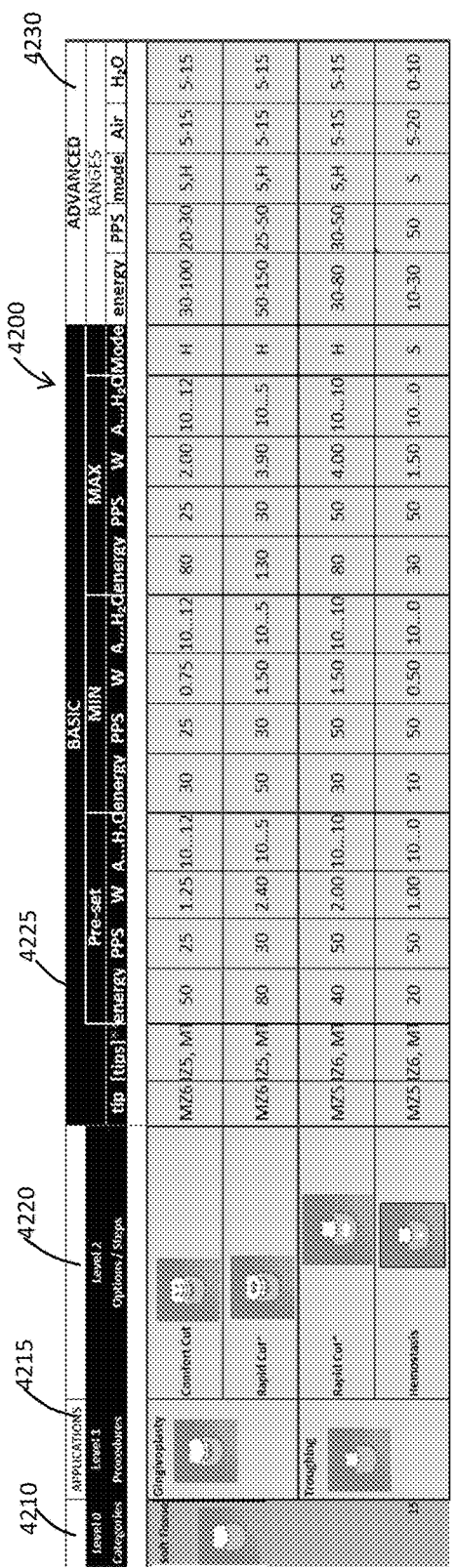
FIG. 42 shows a display of system settings and parameters for procedures, options, and steps for soft tissue categories and gingivectomy, and troughing procedures in accordance with some embodiments of the invention.
Figure 52:
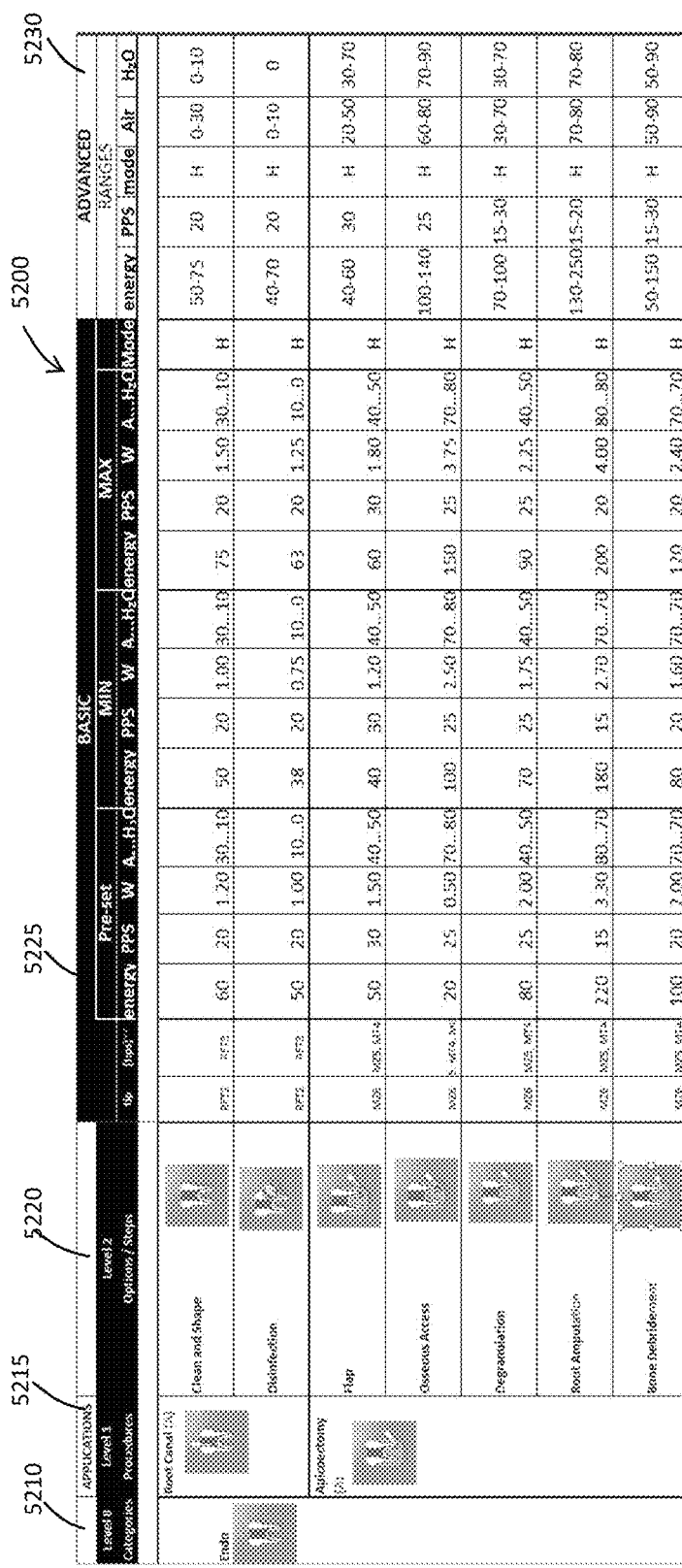
FIG. 52 shows a display of system settings and parameters for procedures, options, and steps for endodontic categories and root canal, and Apicoectomy procedures in accordance with some embodiments of the invention.
Figure 53:
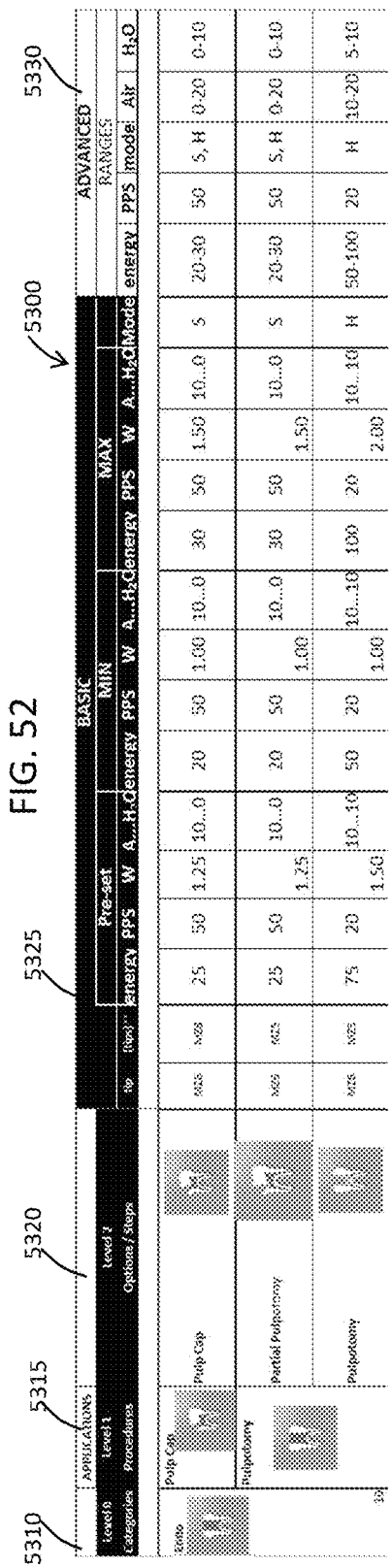
FIG. 53 shows a display of system settings and parameters for procedures, options, and steps for endodontic categories and pulp cap, and pulpotomy procedures in accordance with some embodiments of the invention.

In some further embodiments, various icons, including, but not limited to any of the icons described above, can be used in a representation of system settings and parameters for procedures, options, and steps. For example, FIGS. 37-53 shows system settings and parameters for procedures, options, and steps in accordance with some embodiments of the invention. In some embodiments, the settings can be used with one or more of the procedures, options, and steps described earlier. For example, in summary, FIGS. 37-39 show system settings and parameters for restorative procedures, options, and steps in accordance with some embodiments of the invention. FIGS. 40-42 show system settings and parameters for soft tissue procedures, options, and steps in accordance with some embodiments of the invention. FIGS. 43-47 show system settings and parameters for periodontal procedures, options, and steps in accordance with some embodiments of the invention. FIGS. 48-51 show system settings and parameters for implant procedures, options, and steps in accordance with some embodiments of the invention. FIGS. 52-53 show system settings and parameters for endodontic procedures, options, and steps in accordance with some embodiments of the invention.

Referring to FIGS. 37-39, some embodiments include level 1 procedures with specific level 2 options/steps, each of which include laser settings, tip selections, and settings for air or water as shown. Referring to FIGS. 40-42, some embodiments include level 1 procedures with specific level 2 options/steps, each of which include laser settings, tip selections, and settings for air or water as shown. Referring to FIGS. 43-47, some embodiments include level 1 procedures with specific level 2 options/steps, each of which include laser settings, tip selections, and settings for air or water as shown. Referring to FIGS. 48-51, some embodiments include level 1 procedures with specific level 2 options/steps, each of which include laser settings, tip selections, and settings for air or water as shown. Referring to FIGS. 52-53, some embodiments include level 1 procedures with specific level 2 options/steps, each of which include laser settings, tip selections, and settings for air or water as shown. In some embodiments, any of the settings shown in FIGS. 37-39, and/or FIGS. 40-42, and/or FIGS. 43-47, and/or FIGS. 48-51, and/or FIGS. 52-53 can include tip selection for any specific procedure, basis settings, and advanced ranges. Other settings can include air and water flow rate settings.

The specific settings shown can vary and are non-limiting embodiments only. Other settings can be used without departing from the invention as described herein. For example, FIG. 37 shows a display 3700 of system settings and parameters for procedures, options, and steps for restorative categories and Class 1-2, and Class 3 procedures in accordance with some embodiments of the invention. In some embodiments, the category 3710 can be a restorative category, and the procedure 3715 can be a "Class 1-2(A)" and/or a "Class 3" for this category. In some embodiments, the basic settings 3725 can include pre-set settings, minimum and maximum settings. In some embodiments, the basic settings 3725 can include energy, pulse rate, and power settings of the laser. Further, in some embodiments, within the basic settings, a specific tip and/or optional tips can be displayed alongside the basic setting for laser parameters, and/or air and/or water flow rate settings. Further, some embodiments include advanced settings 3730 including optional ranges of settings or levels. In some embodiments, the advanced settings can include energy, pulse rate, mode, and/or power settings of the laser. Further, within the advanced settings, can include air and/or water flow rate settings. Further, in some embodiments, options and/or steps can be selected for one or more categories and/or procedures. For example, in some embodiments, one or more options or steps 3720 can be selected that can comprise specific basic settings 3725 and/or advanced settings 3730. For example, some embodiments include a "Comfortprep" option/step, a "Bondprep" option/step, or a "Pulp Cap" option/step for a "Class 1-2(A)" procedure, or a "Comfort-Prep" option/step or "BondPrep" option/step for a "Class 3" procedure.

FIG. 38 shows a display 3800 of system settings and parameters for procedures, options, and steps for restorative categories and Class 4, and Class 5 procedures in accordance with some embodiments of the invention. In some embodiments, the category 3810 can be a restorative category, and the procedure 3815 can be a "Class 4 and/or a "Class 5" for this category. In some embodiments, the basic settings 3825 can include pre-set settings, minimum and maximum settings as shown. In some embodiments, the basic settings 3825 can include energy, pulse rate, and power settings of the laser. Further, in some embodiments, within the basic settings 3825, a specific tip and/or optional tips can be displayed alongside the basic setting for laser parameters, and/or air and/or water flow rate settings. Further, some embodiments include advanced settings 3830 including optional ranges of settings or levels. In some embodiments, the advanced settings 3830 can include energy, pulse rate, mode, and/or power settings of the laser. Further, within the advanced settings, can include air and/or water flow rate settings. In some embodiments, one or more options or steps 3820 can be selected that can comprise specific basic settings 3825 and/or advanced settings 3830. For example, some embodiments include a "Comfortprep" option/step or a "Bondprep" option/step for a "Class 4" procedure, and a "Hemostatic Gingivectomy" option/step, "Comfortprep" option/step, and "Bondprep" option/step for a "Class 5" procedure.

FIG. 39 shows a display 3900 of system settings and parameters for procedures, options, and steps for restorative categories and deciduous procedures in accordance with some embodiments of the invention. In some embodiments, the category 3910 can be a restorative category, and the procedure 3915 can be a deciduous procedure for this category. In some embodiments, the basic settings 3925 can include pre-set settings, minimum and maximum settings as shown. In some embodiments, the basic settings 3925 can include energy, pulse rate, and power settings of the laser. Further, in some embodiments, within the basic settings 3925, a specific tip and/or optional tips can be displayed alongside the basic setting for laser parameters, and/or air and/or water flow rate settings. Further, some embodiments include advanced settings 3930 including optional ranges of settings or levels. In some embodiments, the advanced settings 3930 can include energy, pulse rate, mode, and/or power settings of the laser. Further, within the advanced settings, can include air and/or water flow rate settings. In some embodiments, one or more options or steps 3920 can be selected that can comprise specific basic settings 3925 and/or advanced settings 3930. For example, some embodiments include a "Comfortprep Class 1" option/step, "Comfortprep Class 2" option/step, a "Bondprep" option/step, a "Pulp Cap" option/step, or a "Pulpotomy" option/step.

FIG. 40 shows a display 4000 of system settings and parameters for procedures, options, and steps for soft tissue categories and maxillary frenectomy, and lingual frenectomy procedures in accordance with some embodiments of the invention. In some embodiments, the category 4010 can be a soft tissue category, and the procedure 4015 can be a maxillary frenectomy, and lingual frenectomy for this category. In some embodiments, the basic settings 4025 can include pre-set settings, minimum and maximum settings as shown. In some embodiments, the basic settings 4025 can include energy, pulse rate, and power settings of the laser. Further, in some embodiments, within the basic settings 4025, a specific tip and/or optional tips can be displayed alongside the basic setting for laser parameters, and/or air and/or water flow rate settings. Further, some embodiments include advanced settings 4030 including optional ranges of settings or levels. In some embodiments, the advanced settings 4030 can include energy, pulse rate, mode, and/or power settings of the laser. Further, within the advanced settings, can include air and/or water flow rate settings. In some embodiments, one or more options or steps 4020 can be selected that can comprise specific basic settings 4025 and/or advanced settings 4030. For example, some embodiments include separate "Comfort Cut" option/step, a "Rapid Cut" option/step, or a "Hemostasis" option/step for a "Maxillary Frenectomy" procedure, or a "Lingual Frenectomy" procedure.

FIG. 41 shows a display 4100 of system settings and parameters for procedures, options, and steps for soft tissue categories and biopsy, and gingivectomy procedures in accordance with some embodiments of the invention. In some embodiments, the category 4110 can be a soft tissue category, and the procedure 4115 can be a biopsy, and gingivectomy procedure for this category. In some embodiments, the basic settings 4125 can include pre-set settings, minimum and maximum settings as shown. In some embodiments, the basic settings 4125 can include energy, pulse rate, and power settings of the laser. Further, in some embodiments, within the basic settings 4125, a specific tip and/or optional tips can be displayed alongside the basic setting for laser parameters, and/or air and/or water flow rate settings. Further, some embodiments include advanced settings 4130 including optional ranges of settings or levels. In some embodiments, the advanced settings 4130 can include energy, pulse rate, mode, and/or power settings of the laser. Further, within the advanced settings, can include air and/or water flow rate settings. In some embodiments, one or more options or steps 4120 can be selected that can comprise specific basic settings 4125 and/or advanced settings 4130. For example, some embodiments include separate "Comfort Cut" option/step, a "Rapid Cut" option/step, or a "Hemostasis" option/step for a "Biopsy" procedure, and/or a separate "Comfort Cut" option/step, a "Rapid Cut" option/step for a "Gingivectomy" procedure.

FIG. 42 shows a display 4200 of system settings and parameters for procedures, options, and steps for soft tissue categories and gingivectomy, and troughing procedures in accordance with some embodiments of the invention. In some embodiments, the category 4210 can be a soft tissue category, and the procedure 4215 can be a biopsy, and gingivectomy procedure for this category. In some embodiments, the basic settings 4225 can include pre-set settings, minimum and maximum settings as shown. In some embodiments, the basic settings 4225 can include energy, pulse rate, and power settings of the laser. Further, in some embodiments, within the basic settings 4225, a specific tip and/or optional tips can be displayed alongside the basic setting for laser parameters, and/or air and/or water flow rate settings. Further, some embodiments include advanced settings 4230 including optional ranges of settings or levels. In some embodiments, the advanced settings 4230 can include energy, pulse rate, mode, and/or power settings of the laser. Further, within the advanced settings, can include air and/or water flow rate settings. In some embodiments, one or more options or steps 4220 can be selected that can comprise specific basic settings 4225 and/or advanced settings 4230. For example, some embodiments include a "Comfortprep" option/step, a "Rapid Cut" option/step for a "Gingivoplasty" procedure, and/or a "Rapid Cut" option/step or a "Hemostasis" option/step for a "Troughing" procedure.

Figure 43:
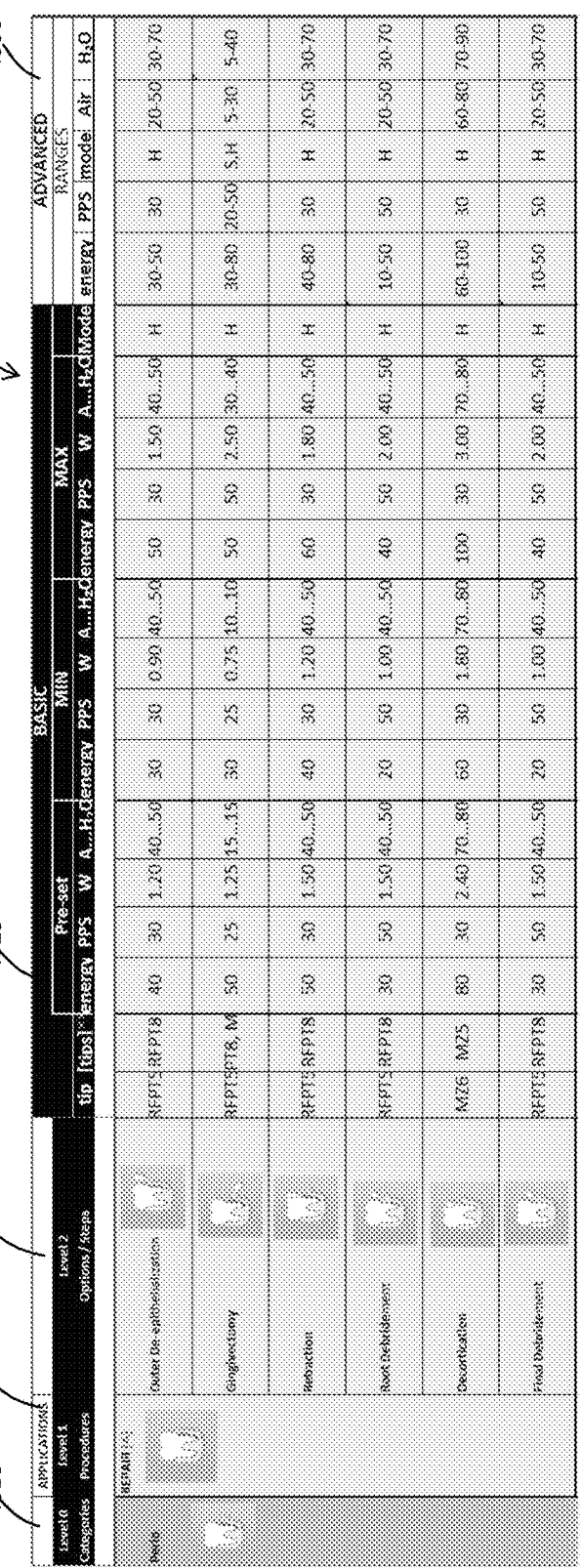
FIG. 43 shows a display of system settings and parameters for procedures, options, and steps for Periodontal categories and repair procedures in accordance with some embodiments of the invention.

FIG. 43 shows a display 4300 of system settings and parameters for procedures, options, and steps for periodontal categories and repair procedures in accordance with some embodiments of the invention. In some embodiments, the category 4310 can be a periodontal category, and the procedure 4315 can be a repair ("A") procedure for this category. In some embodiments, the basic settings 4325 can include pre-set settings, minimum and maximum settings as shown. In some embodiments, the basic settings 4325 can include energy, pulse rate, and power settings of the laser. Further, in some embodiments, within the basic settings 4325, a specific tip and/or optional tips can be displayed alongside the basic setting for laser parameters, and/or air and/or water flow rate settings. Further, some embodiments include advanced settings 4330 including optional ranges of settings or levels. In some embodiments, the advanced settings 4330 can include energy, pulse rate, mode, and/or power settings of the laser. Further, within the advanced settings, can include air and/or water flow rate settings. In some embodiments, one or more options or steps 4320 can be selected that can comprise specific basic settings 4325 and/or advanced settings 4330. For example, some embodiments include a "Outer De-epithelialization" option/step, a "Gingivectomy" option/step, a "Refraction" option/step, a "Root Debridement" option/step, a "Decortication" option/step, or a "Final Debridement" option/step.

FIG. 44 shows a display 4400 of system settings and parameters for procedures, options, and steps for periodontal categories and open flap procedures in accordance with some embodiments of the invention. In some embodiments, the category 4410 can be a periodontal category, and the procedure 4415 can be an open flap procedure for this category. In some embodiments, the basic settings 4425 can include pre-set settings, minimum and maximum settings as shown. In some embodiments, the basic settings 4425 can include energy, pulse rate, and power settings of the laser. Further, in some embodiments, within the basic settings 4425, a specific tip and/or optional tips can be displayed alongside the basic setting for laser parameters, and/or air and/or water flow rate settings. Further, some embodiments include advanced settings 4430 including optional ranges of settings or levels. In some embodiments, the advanced settings 4430 can include energy, pulse rate, mode, and/or power settings of the laser. Further, within the advanced settings, can include air and/or water flow rate settings. In some embodiments, one or more options or steps 4320 can be selected that can comprise specific basic settings 4325 and/or advanced settings 4330. For example, some embodiments include an "Outline" option/step, an "Incision" option/step, an "Outer De-epithelialization" option/step, a "Laser-Assisted Flap Reflection" option/step, a "Secondary Incision" option/step, or a "Degranulation and Collar Removal" option/step, a "Root Surface Modification" option/step, an "Ostectomy" option/step, and an "Osteoplasty" option/step.

Figure 45:
FIG. 45 shows a display of system settings and parameters for procedures, options, and steps for Periodontal categories and Osseous "CL Closed" procedures in accordance with some embodiments of the invention.

FIG. 45 shows a display 4500 of system settings and parameters for procedures, options, and steps for periodontal categories and osseous "CL Closed" procedures in accordance with some embodiments of the invention. In some embodiments, the category 4510 can be a periodontal category, and the procedure 4515 can be an osseous "CL Closed" procedure for this category. In some embodiments, the basic settings 4525 can include pre-set settings, minimum and maximum settings as shown. In some embodiments, the basic settings 4525 can include energy, pulse rate, and power settings of the laser. Further, in some embodiments, within the basic settings 4525, a specific tip and/or optional tips can be displayed alongside the basic setting for laser parameters, and/or air and/or water flow rate settings. Further, some embodiments include advanced settings 4530 including optional ranges of settings or levels. In some embodiments, the advanced settings 4530 can include energy, pulse rate, mode, and/or power settings of the laser. Further, within the advanced settings, can include air and/or water flow rate settings. In some embodiments, one or more options or steps 4520 can be selected that can comprise specific basic settings 4525 and/or advanced settings 4530. For example, some embodiments include an "outline" option/step, a "Gingivectomy" option/step, an "Ostectomy" option/step, and a "Gingivo-Plasty" option/step.

Figure 46:
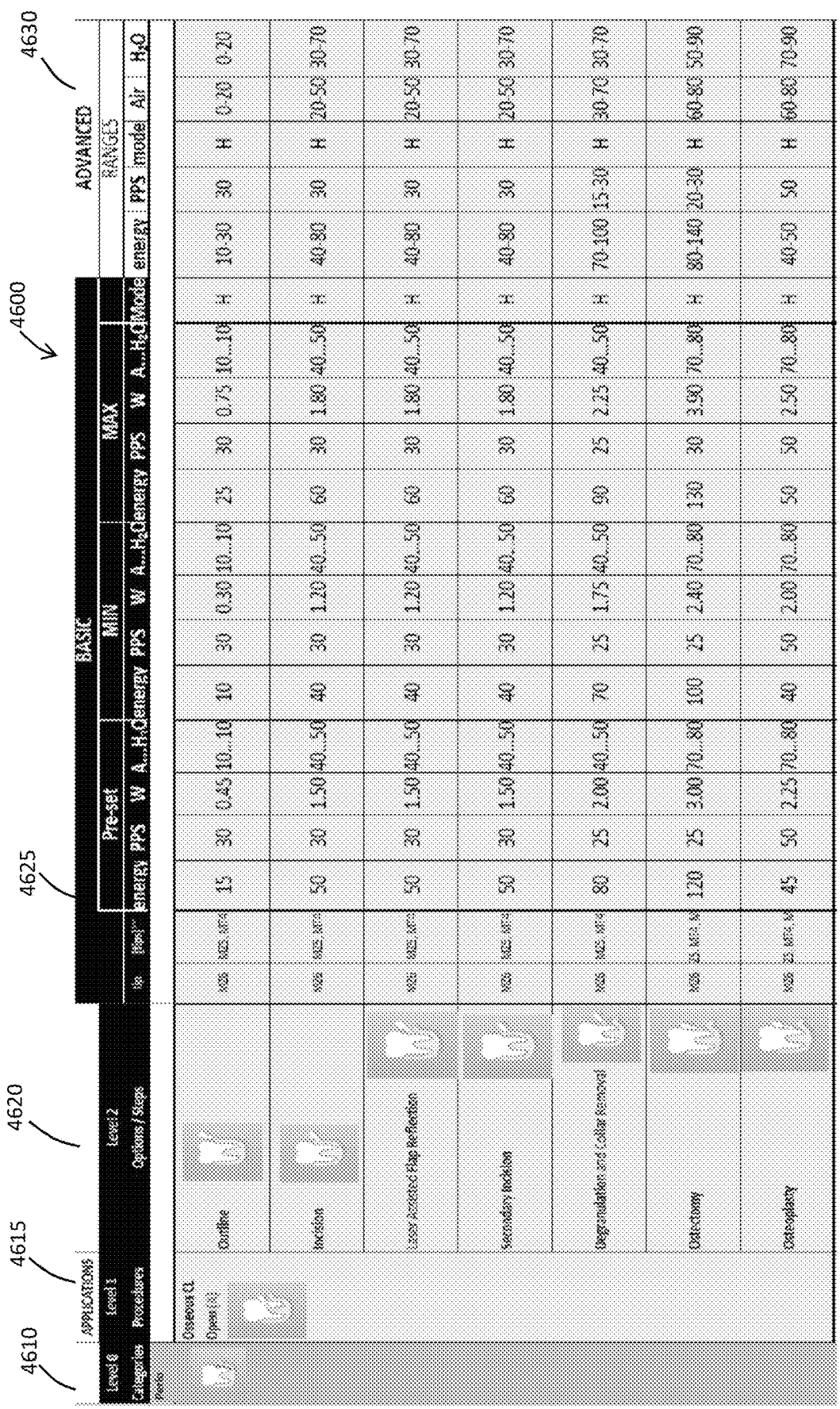
FIG. 46 shows a display of system settings and parameters for procedures, options, and steps for Periodontal categories and Osseous "CL Open" procedures in accordance with some embodiments of the invention.

FIG. 46 shows a display 4600 of system settings and parameters for procedures, options, and steps for Periodontal categories and Osseous "CL Open" procedures in accordance with some embodiments of the invention. In some embodiments, the category 4610 can be a periodontal category, and the procedure 4615 can be an osseous "CL Open" procedure for this category. In some embodiments, the basic settings 4625 can include pre-set settings, minimum and maximum settings as shown. In some embodiments, the basic settings 4625 can include energy, pulse rate, and power settings of the laser. Further, in some embodiments, within the basic settings 4625, a specific tip and/or optional tips can be displayed alongside the basic setting for laser parameters, and/or air and/or water flow rate settings. Further, some embodiments include advanced settings 4630 including optional ranges of settings or levels. In some embodiments, the advanced settings 4630 can include energy, pulse rate, mode, and/or power settings of the laser. Further, within the advanced settings, can include air and/or water flow rate settings. In some embodiments, one or more options or steps 4620 can be selected that can comprise specific basic settings 4625 and/or advanced settings 4630. For example, some embodiments include an "Outline" option/step, an "Incision" option/step, a "Laser Assisted Flap Reflection" option/step, a "Secondary Incision" option/step, a "Degranulation and Collar Removal" option/step, an "Ostectomy" option/step, and an "Osteoplasty" option/step.

Figure 47:
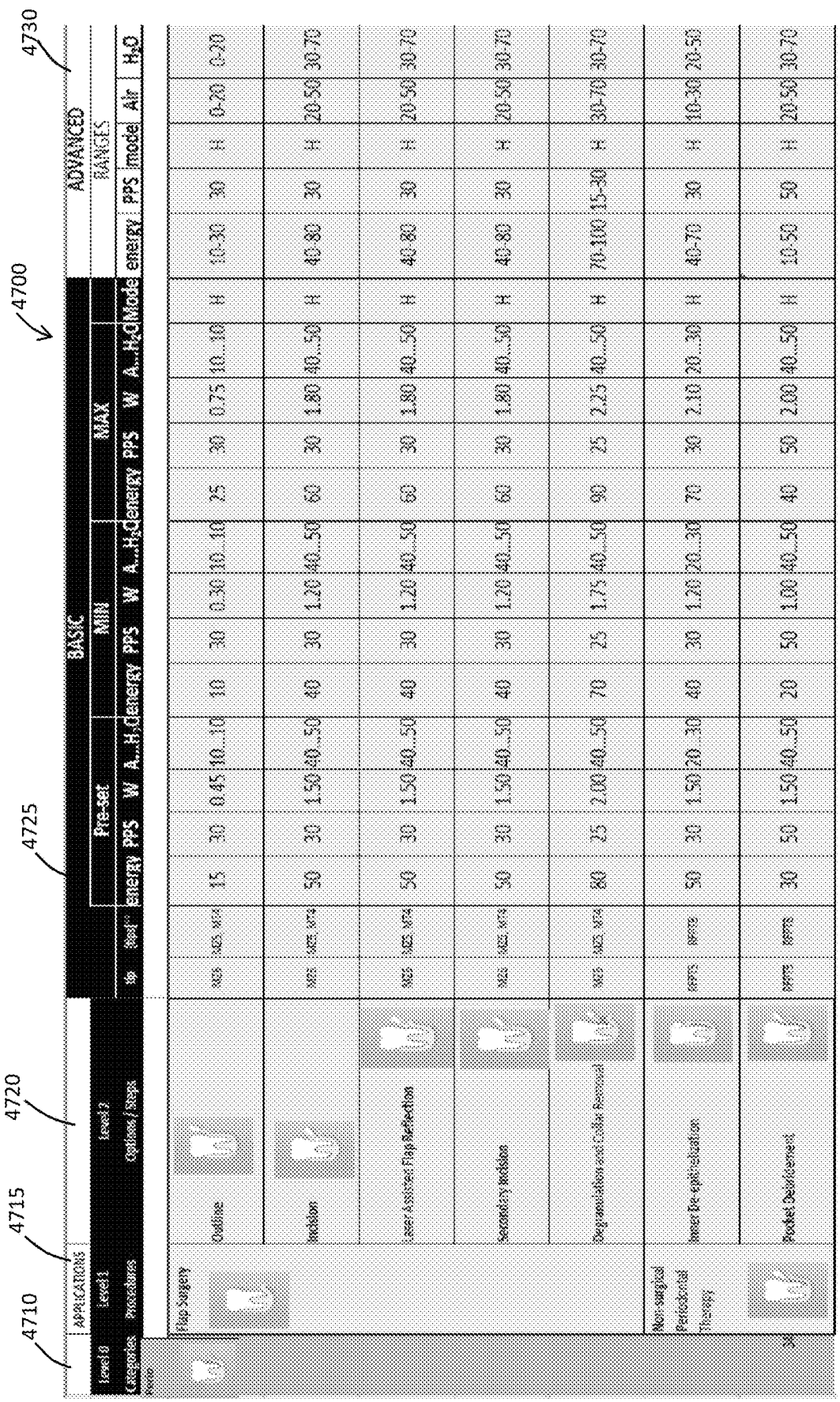
FIG. 47 shows a display of system settings and parameters for procedures, options, and steps for Periodontal categories and flap surgery, and non-surgical periodontal procedures in accordance with some embodiments of the invention.

FIG. 47 shows a display 4700 of system settings and parameters for procedures, options, and steps for periodontal categories and flap surgery, and non-surgical periodontal procedures in accordance with some embodiments of the invention. In some embodiments, the category 4710 can be a periodontal category, and the procedure 4715 can be flap surgery, and non-surgical periodontal procedures for this category. In some embodiments, the basic settings 4725 can include pre-set settings, minimum and maximum settings as shown. In some embodiments, the basic settings 4725 can include energy, pulse rate, and power settings of the laser. Further, in some embodiments, within the basic settings 4725, a specific tip and/or optional tips can be displayed alongside the basic setting for laser parameters, and/or air and/or water flow rate settings. Further, some embodiments include advanced settings 4730 including optional ranges of settings or levels. In some embodiments, the advanced settings 4730 can include energy, pulse rate, mode, and/or power settings of the laser. Further, within the advanced settings, can include air and/or water flow rate settings. In some embodiments, one or more options or steps 4720 can be selected that can comprise specific basic settings 4725 and/or advanced settings 4730. For example, some embodiments include an "Outline" option/step, an "Incision" option/step, a "Laser Assisted Flap Reflection" option/step, a "Secondary Incision" option/step, a "Degranulation and Collar removal" option/step.

Figure 48:
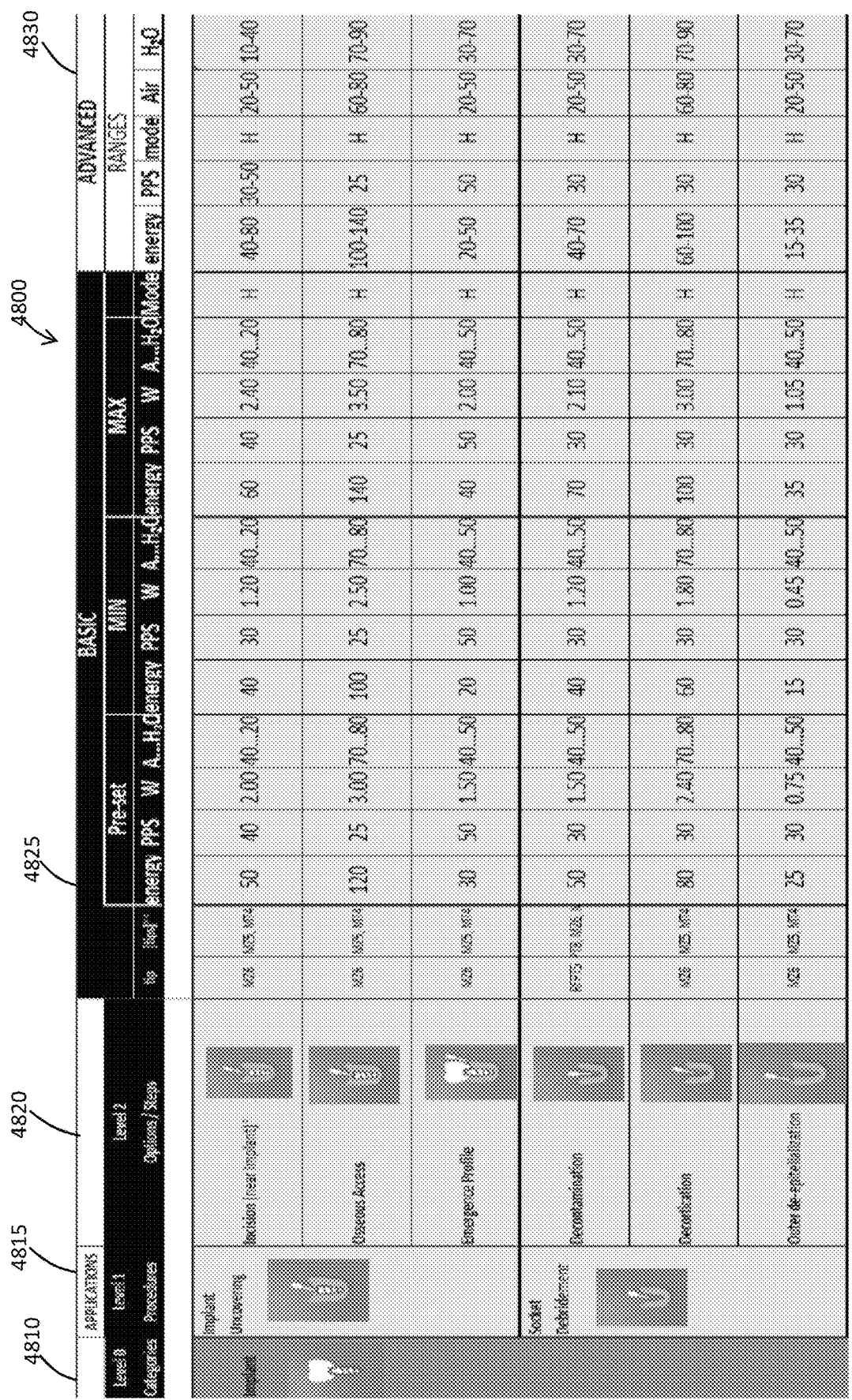
FIG. 48 shows a display of system settings and parameters for procedures, options, and steps for implant categories and implant uncovering, and socket debridement procedures in accordance with some embodiments of the invention.

FIG. 48 shows a display 4800 of system settings and parameters for procedures, options, and steps for implant categories and implant uncovering, and socket debridement procedures in accordance with some embodiments of the invention. In some embodiments, the category 4810 can be implant categories and implant uncovering, and socket debridement procedures for this category. In some embodiments, the basic settings 4825 can include pre-set settings, minimum and maximum settings as shown. In some embodiments, the basic settings 4825 can include energy, pulse rate, and power settings of the laser. Further, in some embodiments, within the basic settings 4825, a specific tip and/or optional tips can be displayed alongside the basic setting for laser parameters, and/or air and/or water flow rate settings. Further, some embodiments include advanced settings 4830 including optional ranges of settings or levels. In some embodiments, the advanced settings 4830 can include energy, pulse rate, mode, and/or power settings of the laser. Further, within the advanced settings, can include air and/or water flow rate settings. In some embodiments, one or more options or steps 4820 can be selected that can comprise specific basic settings 4825 and/or advanced settings 4830. For example, some embodiments include an "Incision near implant" option/step, an "Osseous Access" option/step, and an "Emergence Profile" option/step for an implant uncovering procedure, and a "Decontamination" option/step, a "Decortication" option/step, or an "Outer de-epithelialization" option/step for a socket debridement procedure.

Figure 49:
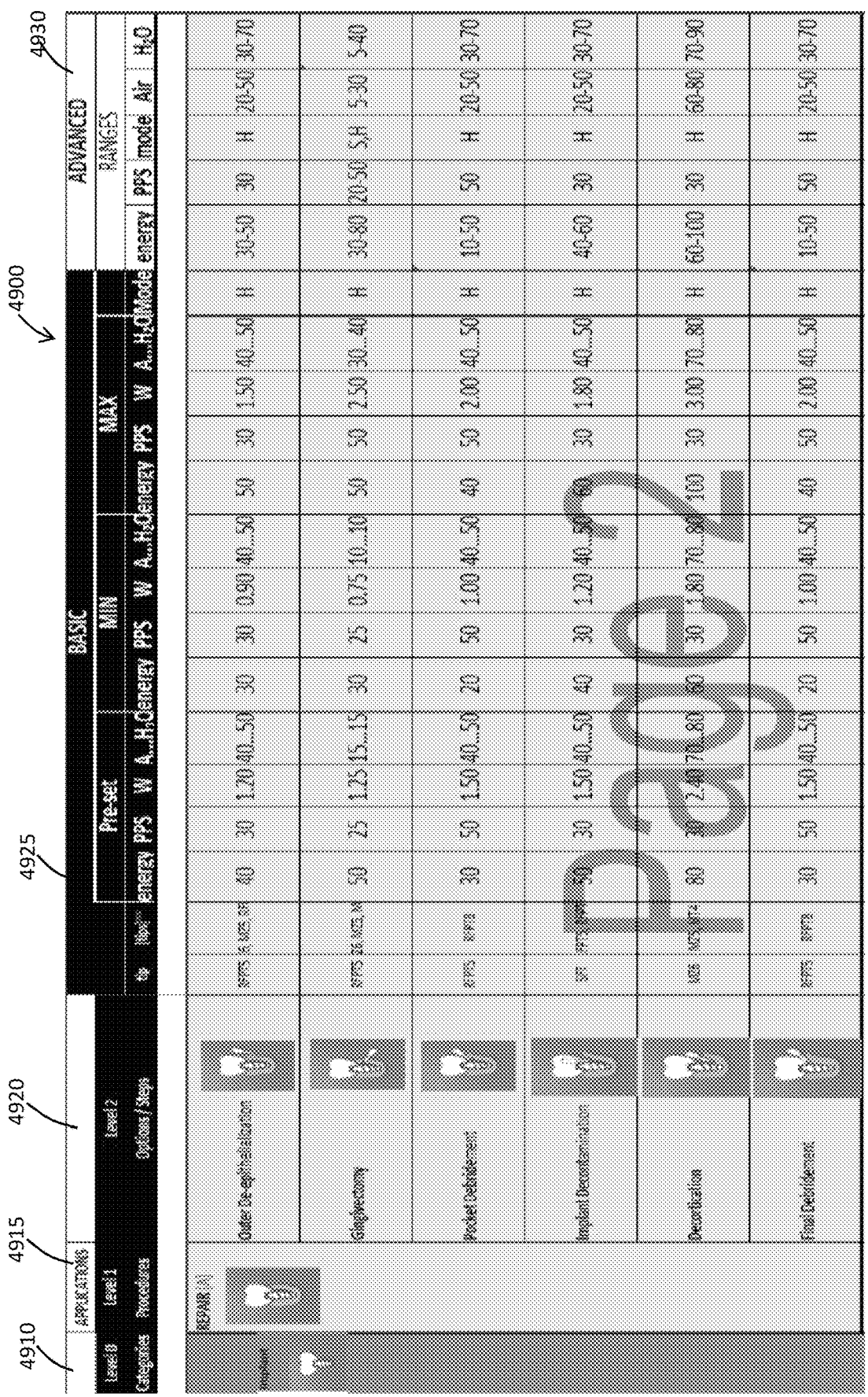
FIG. 49 shows a display of system settings and parameters for procedures, options, and steps for implant categories and repair procedures in accordance with some embodiments of the invention.

FIG. 49 shows a display 4900 of system settings and parameters for procedures, options, and steps for implant categories and repair procedures in accordance with some embodiments of the invention. In some embodiments, the category 4910 can be implant categories and implant repair procedures for this category. In some embodiments, the basic settings 4925 can include pre-set settings, minimum and maximum settings as shown. In some embodiments, the basic settings 4925 can include energy, pulse rate, and power settings of the laser. Further, in some embodiments, within the basic settings 4925, a specific tip and/or optional tips can be displayed alongside the basic setting for laser parameters, and/or air and/or water flow rate settings. Further, some embodiments include advanced settings 4930 including optional ranges of settings or levels. In some embodiments, the advanced settings 4930 can include energy, pulse rate, mode, and/or power settings of the laser. Further, within the advanced settings, can include air and/or water flow rate settings. In some embodiments, one or more options or steps 4920 can be selected that can comprise specific basic settings 4925 and/or advanced settings 4930. For example, some embodiments include an "Outer De-epithelialization" option/step, a "Gingivectomy" option/step, a "Pocket Debridment" option/step, an "Implant Decontamination" option/step, a "Decortication" option/step, and/or a "Final Debridement" option/step.

Figure 50:
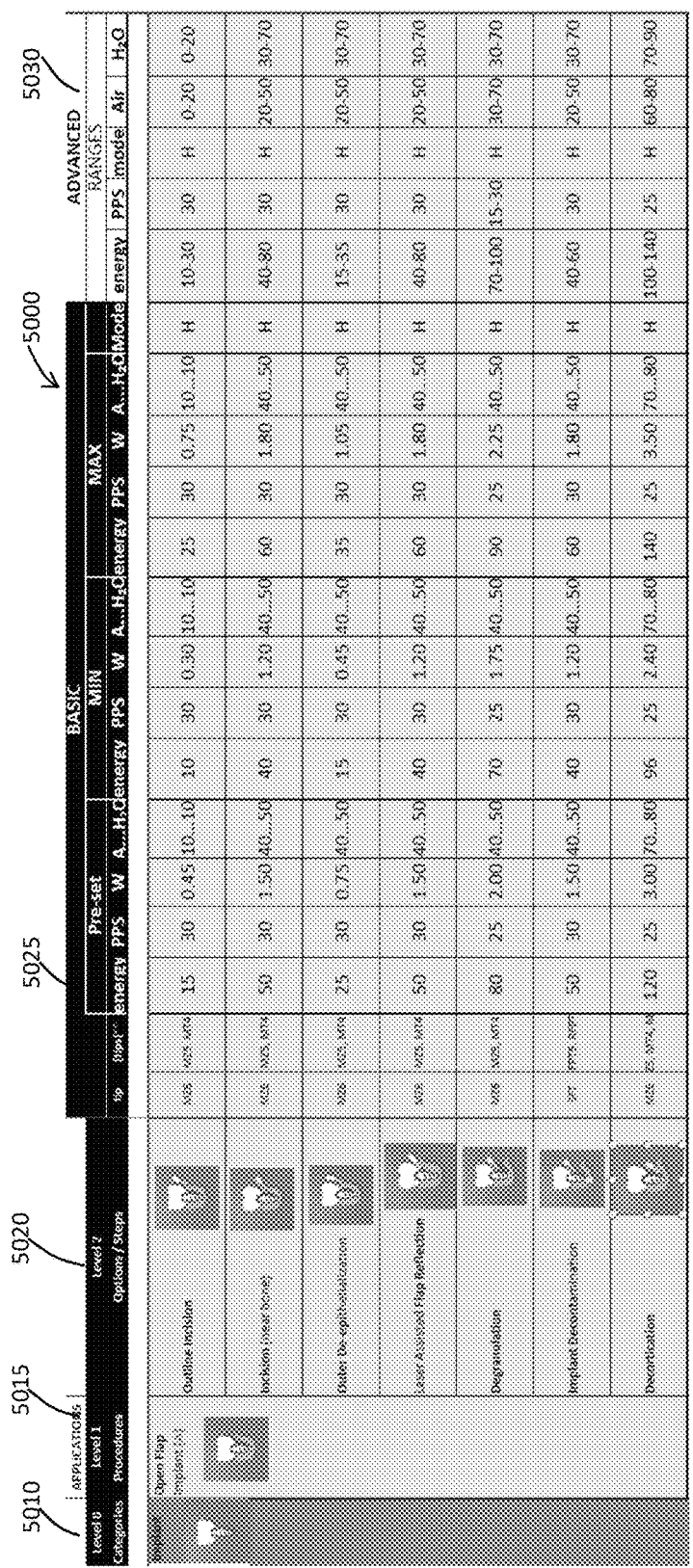
FIG. 50 shows a display of system settings and parameters for procedures, options, and steps for implant categories and open flap implant in accordance with some embodiments of the invention.

FIG. 50 shows a display 5000 of system settings and parameters for procedures, options, and steps for implant categories and open flap implant in accordance with some embodiments of the invention. In some embodiments, the category 5010 can be implant categories and open flap procedures for this category. In some embodiments, the basic settings 5025 can include pre-set settings, minimum and maximum settings as shown. In some embodiments, the basic settings 5025 can include energy, pulse rate, and power settings of the laser. Further, in some embodiments, within the basic settings 5025, a specific tip and/or optional tips can be displayed alongside the basic setting for laser parameters, and/or air and/or water flow rate settings. Further, some embodiments include advanced settings 5030 including optional ranges of settings or levels. In some embodiments, the advanced settings 5030 can include energy, pulse rate, mode, and/or power settings of the laser. Further, within the advanced settings, can include air and/or water flow rate settings. In some embodiments, one or more options or steps 5020 can be selected that can comprise specific basic settings 5025 and/or advanced settings 5030. For example, some embodiments include an "Outline" option/step, an "Incision (near bone)" option/step, an "Outer De-epithelialization" option/step, a "Laser Assisted Flap Reflection" option/step, a "Degranulation" option/step, an "Implant Decontamination" option/step, and/or a "Decortication" option/step.

Figure 51:
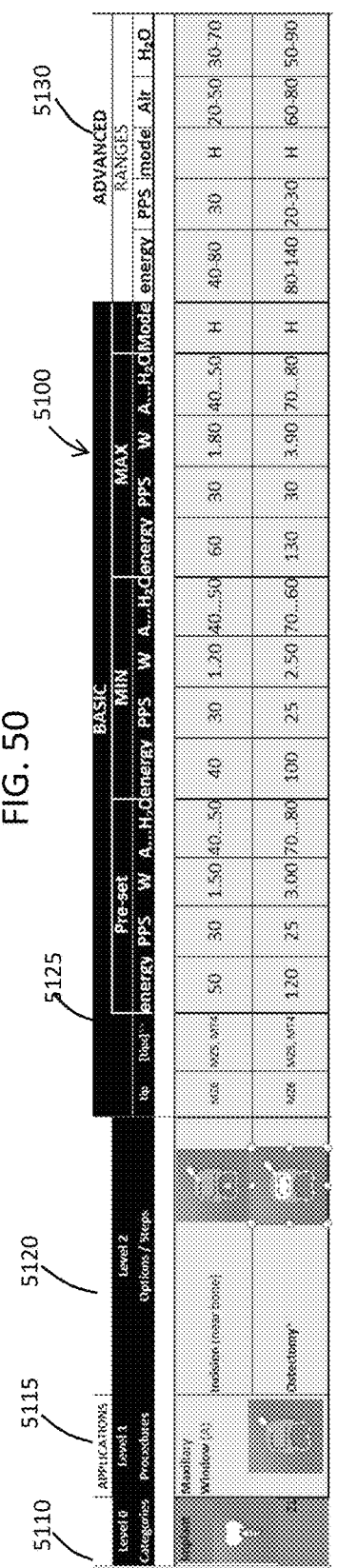
FIG. 51 shows a display of system settings and parameters for procedures, options, and steps for implant categories and maxillary window procedures in accordance with some embodiments of the invention.

FIG. 51 shows a display 5100 of system settings and parameters for procedures, options, and steps for implant categories and maxillary window procedures in accordance with some embodiments of the invention. In some embodiments, the category 5110 can be implant categories and maxillary window procedures for this category. In some embodiments, the basic settings 5125 can include pre-set settings, minimum and maximum settings as shown. In some embodiments, the basic settings 5125 can include energy, pulse rate, and power settings of the laser. Further, in some embodiments, within the basic settings 5125, a specific tip and/or optional tips can be displayed alongside the basic setting for laser parameters, and/or air and/or water flow rate settings. Further, some embodiments include advanced settings 5130 including optional ranges of settings or levels. In some embodiments, the advanced settings 5130 can include energy, pulse rate, mode, and/or power settings of the laser. Further, within the advanced settings, can include air and/or water flow rate settings. In some embodiments, one or more options or steps 5120 can be selected that can comprise specific basic settings 5125 and/or advanced settings 5130. For example, some embodiments include an "Incision (near bone)" option/step, and/or an "Ostectomy" option/step.

FIG. 52 shows a display 5200 of system settings and parameters for procedures, options, and steps for endodontic categories and root canal, and apicoectomy procedures in accordance with some embodiments of the invention. In some embodiments, the category 5210 can be endodontic categories and root canal, and apicoectomy procedures for this category. In some embodiments, the basic settings 5225 can include pre-set settings, minimum and maximum settings as shown. In some embodiments, the basic settings 5225 can include energy, pulse rate, and power settings of the laser. Further, in some embodiments, within the basic settings 5225, a specific tip and/or optional tips can be displayed alongside the basic setting for laser parameters, and/or air and/or water flow rate settings. Further, some embodiments include advanced settings 5230 including optional ranges of settings or levels. In some embodiments, the advanced settings 5230 can include energy, pulse rate, mode, and/or power settings of the laser. Further, within the advanced settings, can include air and/or water flow rate settings. In some embodiments, one or more options or steps 5220 can be selected that can comprise specific basic settings 5225 and/or advanced settings 5230. For example, some embodiments include a "Clean and Shape" option/step, a "Disinfection" option/step, a "Flap" option/step, an "Osseous Access" option/step, a "Degranulation" option/step, a "Root Amputation" option/step, and a "Bone Debridment" option/step.

FIG. 53 shows a display 5300 of system settings and parameters for procedures, options, and steps for endodontic categories and pulp cap, and pulpotomy procedures in accordance with some embodiments of the invention. In some embodiments, the category 5310 can be endodontic categories and pulp cap, and pulpotomy procedures for this category. In some embodiments, the basic settings 5325 can include pre-set settings, minimum and maximum settings as shown. In some embodiments, the basic settings 5325 can include energy, pulse rate, and power settings of the laser. Further, in some embodiments, within the basic settings 5325, a specific tip and/or optional tips can be displayed alongside the basic setting for laser parameters, and/or air and/or water flow rate settings. Further, some embodiments include advanced settings 5330 including optional ranges of settings or levels. In some embodiments, the advanced settings 5330 can include energy, pulse rate, mode, and/or power settings of the laser. Further, within the advanced settings, can include air and/or water flow rate settings. In some embodiments, one or more options or steps 5320 can be selected that can comprise specific basic settings 5325 and/or advanced settings 5330. For example, some embodiments include a a "Pulp Cap" option/step, a "Partial Pulpotomy" option/step, and/or a "Pulpotomy" option/step.

With the above embodiments in mind, it should be understood that the invention can employ various computer-implemented operations involving dentistry control data stored in computer systems. Moreover, the above-described databases and models throughout the dentistry control can store analytical models and other data on computer-readable storage media within the system 30 and on computer-readable storage media coupled to the system 30. In addition, the above-described applications of the dentistry control system can be stored on computer-readable storage media within the system 30 and on computer-readable storage media coupled to the system 30. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated.

Any of the operations described herein that form part of the invention are useful machine operations. The invention also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data is obtained over a network the data can be processed by other computers on the network, e.g. a cloud of computing resources.

The embodiments of the present invention can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally or in particular formats that enable the construction or depiction of a physical and tangible object. In some embodiments, the manipulation can be performed by a processor. In such an example, the processor thus transforms the data from one thing to another. Still further, the methods can be processed by one or more machines or processors that can be connected over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims.

The invention claimed is:

1. A dental system comprising:
   at least one dental station including at least one dental treatment device;
   at least one processor;
   at least one non-transitory computer-readable storage medium in data communication with the at least one processor, the at least one non-transitory computer-readable storage medium including program instructions executable by the at least one processor enabling or operating an exchange of data between the at least one dental station and at least one remote network; and
   at least one Graphic User Interface (GUI) display configured and arranged to display at least one operating parameter or function of the at least one dental station and display at least some of the data exchanged between the at least one dental station and at least one remote network,
   wherein the program instructions include instructions sufficient to direct the at least one processor to update the at least one GUI display with a plurality of user-selectable graphics arranged adjacent a central display; and
   wherein selection of at least one of the plurality of user-selectable graphics controls at least one function of the at least one dental station.

2. The dental system of claim 1, wherein the at least one GUI display comprises at least one percentage display.

3. The dental system of claim 1, further comprising a handpiece assembly coupled to or including the at least one dental station; and
   wherein the at least one GUI display is configured and arranged to enable adjustment of operational characteristics of the handpiece assembly.

4. The dental system of claim 1, wherein the at least one GUI display comprises a touchscreen display of a computer or smartphone.

5. The dental system of claim 1, wherein the at least one GUI display is configured and arranged to enable monitoring or adjustment of operational characteristics of the at least one dental treatment device.

6. The dental system of claim 1, wherein the program instructions include instructions sufficient to direct the processor to enable downloading software or firmware updates over the remote network to the at least one dental station to update the at least one dental station.

7. The dental system of claim 1, wherein the program instructions include instructions sufficient to direct the processor to update the at least one GUI display with a plurality of user-selectable graphics representing or including at least one dental procedure or parameter.

8. The dental system of claim 1, wherein the program instructions include instructions sufficient to direct the processor to record or direct feedback from at least one patient from at least one clinical procedure.

9. The dental system of claim 1, wherein the program instructions include instructions sufficient to direct the processor to display at least one of interactive training, image-based clinical recommendations, and record at least one patient's outcome.

10. The dental system of claim 1, wherein the program instructions include instructions sufficient to direct the processor to enable alteration, uploading or deletion of at least one procedure by a user directly interacting with the dental station or remotely by a user or manufacturer.

11. The dental system of claim 1, wherein the program instructions include instructions sufficient to direct the processor to image compare or pattern recognize one or more clinical images loaded in its memory with one or more images from any procedure of the dental station.

12. The dental system of claim 11, further comprising program instructions sufficient to direct the processor to provide clinical recommendations based at least in part on image comparison or pattern recognition.

13. The dental system of claim 1, wherein the at least one GUI includes a control and information display including the plurality of user-selectable graphics positioned adjacent one another.

14. The dental system of claim 1, wherein the plurality of user-selectable graphics include icons or segments representing selectable categories of procedures, where a user-selection of icons or segments is represented by at least one of color, shape, size, and animation of at least one selected icon or segment.

15. The dental system of claim 1, wherein the plurality of user-selectable graphics includes at least one icon selectable by a user to enable access of one or more favorites.

16. The dental system of claim 1, wherein the plurality of user-selectable graphics includes category segments or buttons, configured and arranged to enable the at least one processor to modify attribute values, or to allow personification of a specific doctor's preference system.

17. The dental system of claim 1, wherein the plurality of user-selectable graphics includes at least one controller configured and arranged to enable the at least one processor to update or modify at least one of the pulse repetition rate, pulse duration, average output power, and volume and quality of the water, and air flow.

18. The dental system of claim 17, wherein the at least one controller is a master controller configured and arranged to enable a user to substantially simultaneously set or alter more than one parameter selected from pulse power, pulse repetition rate, pulse duration, average output power, and volume and quality of the water, and air flow.

19. The dental system of claim 1, further comprising program instructions sufficient to direct the processor to display a schematic view of at least a portion of the at least one dental station, and at least one icon displayed to enable user selection of at least one dental accessory.

* * * * *